United States Patent
Selnick et al.

(10) Patent No.: US 8,765,759 B2
(45) Date of Patent: Jul. 1, 2014

(54) MONOCYCLIC CGRP RECEPTOR ANTAGONISTS

(75) Inventors: Harold G. Selnick, Ambler, PA (US); Ian M. Bell, Harleysville, PA (US); Melody McWherter, Boyertown, PA (US); Donnette D. Staas, Harleysville, PA (US); Shawn J. Stachel, Perkasie, PA (US); Thomas Steele, Schwenksville, PA (US); Craig Stump, Pottstown, PA (US); Michael R. Wood, Brentwood, TN (US); C. Blair Zartman, Hatfield, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 445 days.

(21) Appl. No.: 12/934,208

(22) PCT Filed: Mar. 24, 2009

(86) PCT No.: PCT/US2009/038013
§ 371 (c)(1),
(2), (4) Date: Sep. 23, 2010

(87) PCT Pub. No.: WO2009/120652
PCT Pub. Date: Oct. 1, 2009

(65) Prior Publication Data
US 2011/0021516 A1    Jan. 27, 2011

Related U.S. Application Data

(60) Provisional application No. 61/072,236, filed on Mar. 28, 2008.

(51) Int. Cl.
*A61K 31/437* (2006.01)
*A61K 31/497* (2006.01)
*A61K 31/4985* (2006.01)

(52) U.S. Cl.
USPC ...... 514/249; 514/255.05; 514/300; 544/350; 544/405; 546/113

(58) Field of Classification Search
CPC ............................ C07D 401/10; C07D 209/54
USPC .................... 544/350, 405; 546/113
See application file for complete search history.

(56) References Cited

U.S. PATENT DOCUMENTS

| 7,625,901 B2 | 12/2009 | Wood et al. |
| 7,629,338 B2 | 12/2009 | Wood et al. |
| 7,659,300 B2 | 2/2010 | Bell et al. |
| 2007/0265226 A1 | 11/2007 | Lee et al. |
| 2008/0004261 A1 | 1/2008 | Gutierrez et al. |
| 2010/0056498 A1 | 3/2010 | Wood et al. |
| 2010/0152216 A1 | 6/2010 | Stump et al. |

FOREIGN PATENT DOCUMENTS

| WO | WO2008127584 | 10/2008 |
| WO | WO2009120652 | 10/2009 |
| WO | WO2011014383 | 2/2011 |

OTHER PUBLICATIONS

PCT International Search Report dated Sep. 2, 2010 for related International Application No. PCT/US2010/042509; 2 pages.
Written Opinion of the PCT International Search Report dated Sep. 2, 2010 for related International Application No. PCT/US2010/042509; 3 pages.
Co-pending U.S. Appl. No. 12/594,993, filed May 27, 2010; published US 2010-0292262 on Nov. 18, 2010.
Co-pending U.S. Appl. No. 13/386,955, filed Jul. 20, 2010; published US2012-0121508 on May 17, 2012.
PCT International Search Report dated Sep. 2, 2010 for related International Application No. PCT/US2008/004528; 1 pages.
Written Opinion of the PCT International Search Report dated Sep. 2, 2010 for related International Application No. PCT/US2008/04528; 2 pages.
PCT International Search Report dated Sep. 2, 2010 for related International Application No. PCT/US2009/038013; 2 pages.
Written Opinion of the PCT International Search Report dated Sep. 2, 2010 for related International Application No. PCT/US2009/038013; 3 pages.

*Primary Examiner* — Brian McDowell
(74) *Attorney, Agent, or Firm* — H. Eric Fischer; John C. Todaro

(57) ABSTRACT

The present invention is directed to compounds of the formula:

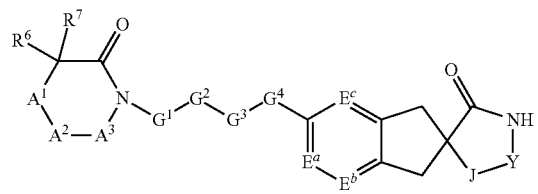

(wherein variables $A^1$, $A^2$, $A^3$, $G^1$, $G^2$, $G^3$, $G^4$, J, $E^a$, $E^b$, $E^c$, $R^6$, $R^7$, and Y are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

12 Claims, No Drawings

MONOCYCLIC CGRP RECEPTOR ANTAGONISTS

PRIORITY CLAIM

This application is a §371 National Stage Application of PCT/US09/38013, filed on Mar. 24, 2009, which claims priority from U.S. Provisional Application Ser. No. 61/072,236, filed on Mar. 28, 2008.

BACKGROUND OF THE INVENTION

CGRP (Calcitonin Gene-Related Peptide) is a naturally occurring 37-amino acid peptide that is generated by tissue-specific alternate processing of calcitonin messenger RNA and is widely distributed in the central and peripheral nervous system. CGRP is localized predominantly in sensory afferent and central neurons and mediates several biological actions, including vasodilation. CGRP is expressed in alpha- and beta-forms that vary by one and three amino acids in the rat and human, respectively. CGRP-alpha and CGRP-beta display similar biological properties. When released from the cell, CGRP initiates its biological responses by binding to specific cell surface receptors that are predominantly coupled to the activation of adenylyl cyclase. CGRP receptors have been identified and pharmacologically evaluated in several tissues and cells, including those of brain, cardiovascular, endothelial, and smooth muscle origin.

Based on pharmacological properties, these receptors are divided into at least two subtypes, denoted $CGRP_1$ and $CGRP_2$. Human $\alpha$-CGRP-(8-37), a fragment of CGRP that lacks seven N-terminal amino acid residues, is a selective antagonist of $CGRP_1$, whereas the linear analogue of CGRP, diacetoamido methyl cysteine CGRP ([Cys(ACM)2,7] CGRP), is a selective agonist of CGRP2. CGRP is a potent neuromodulator that has been implicated in the pathology of cerebrovascular disorders such as migraine and cluster headache. In clinical studies, elevated levels of CGRP in the jugular vein were found to occur during migraine attacks (Goadsby et al., Ann. Neurol., 1990, 28, 183-187), salivary levels of CGRP are elevated in migraine subjects between attacks (Bellamy et al., Headache, 2006, 46, 24-33), and CGRP itself has been shown to trigger migrainous headache (Lassen et al., Cephalalgia, 2002, 22, 54-61). In clinical trials, the CGRP antagonist BIBN4096BS has been shown to be effective in treating acute attacks of migraine (Olesen et al., New Engl. J. Med., 2004, 350, 1104-1110) and was able to prevent headache induced by CGRP infusion in a control group (Petersen et al., Clin. Pharmacol. Ther., 2005, 77, 202-213).

CGRP-mediated activation of the trigeminovascular system may play a key role in migraine pathogenesis. Additionally, CGRP activates receptors on the smooth muscle of intracranial vessels, leading to increased vasodilation, which is thought to contribute to headache pain during migraine attacks (Lance, Headache Pathogenesis: Monoamines, Neuropeptides, Purines and Nitric Oxide, Lippincott-Raven Publishers, 1997, 3-9). The middle meningeal artery, the principle artery in the dura mater, is innervated by sensory fibers from the trigeminal ganglion which contain several neuropeptides, including CGRP. Trigeminal ganglion stimulation in the cat resulted in increased levels of CGRP, and in humans, activation of the trigeminal system caused facial flushing and increased levels of CGRP in the external jugular vein (Goadsby et al., Ann. Neurol., 1988, 23, 193-196). Electrical stimulation of the dura mater in rats increased the diameter of the middle meningeal artery, an effect that was blocked by prior administration of CGRP(8-37), a peptide CGRP antagonist (Williamson et al., Cephalalgia, 1997, 17, 525-531). Trigeminal ganglion stimulation increased facial blood flow in the rat, which was inhibited by CGRP(8-37) (Escott et al., Brain Res. 1995, 669, 93-99). Electrical stimulation of the trigeminal ganglion in marmoset produced an increase in facial blood flow that could be blocked by the non-peptide CGRP antagonist BIBN4096BS (Doods et al., Br. J. Pharmacol., 2000, 129, 420-423). Thus the vascular effects of CGRP may be attenuated, prevented or reversed by a CGRP antagonist.

CGRP-mediated vasodilation of rat middle meningeal artery was shown to sensitize neurons of the trigeminal nucleus caudalis (Williamson et al., The CGRP Family: Calcitonin Gene-Related Peptide (CGRP), Amylin, and Adrenomedullin, Landes Bioscience, 2000, 245-247). Similarly, distention of dural blood vessels during migraine headache may sensitize trigeminal neurons. Some of the associated symptoms of migraine, including extra-cranial pain and facial allodynia, may be the result of sensitized trigeminal neurons (Burstein et al., Ann. Neurol. 2000, 47, 614-624). A CGRP antagonist may be beneficial in attenuating, preventing or reversing the effects of neuronal sensitization.

The ability of the compounds of the present invention to act as CGRP antagonists makes them useful pharmacological agents for disorders that involve CGRP in humans and animals, but particularly in humans. Such disorders include migraine and cluster headache (Doods, Curr Opin Inves Drugs, 2001, 2 (9), 1261-1268; Edvinsson et al., Cephalalgia, 1994, 14, 320-327); chronic tension type headache (Ashina et al., Neurology, 2000, 14, 1335-1340); pain (Yu et al., Eur. J. Pharm., 1998, 347, 275-282); chronic pain (Hulsebosch et al., Pain, 2000, 86, 163-175); neurogenic inflammation and inflammatory pain (Holzer, Neurosci., 1988, 24, 739-768; Delay-Goyet et al., Acta Physiol. Scanda. 1992, 146, 537-538; Salmon et al., Nature Neurosci., 2001, 4(4), 357-358); eye pain (May et al. Cephalalgia, 2002, 22, 195-196), tooth pain (Awawdeh et al., Int. Endocrin. J., 2002, 35, 30-36), non-insulin dependent diabetes mellitus (Molina et al., Diabetes, 1990, 39, 260-265); vascular disorders; inflammation (Zhang et al., Pain, 2001, 89, 265), arthritis, bronchial hyperreactivity, asthma, (Foster et al., Ann. NY Acad. Sci., 1992, 657, 397-404; Schini et al., Am. J. Physiol., 1994, 267, H2483-H2490; Zheng et al., J. Virol., 1993, 67, 5786-5791); shock, sepsis (Beer et al., Crit. Care Med., 2002, 30 (8), 1794-1798); opiate withdrawal syndrome (Salmon et al., Nature Neurosci., 2001, 4(4), 357-358); morphine tolerance (Menard et al., J. Neurosci., 1996, 16 (7), 2342-2351); hot flashes in men and women (Chen et al., Lancet, 1993, 342, 49; Spetz et al., J. Urology, 2001, 166, 1720-1723); allergic dermatitis (Wallengren, Contact Dermatitis, 2000, 43 (3), 137-143); psoriasis; encephalitis, brain trauma, ischaemia, stroke, epilepsy, and neurodegenerative diseases (Rohrenbeck et al., Neurobiol. of Disease 1999, 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al., J. Membrane Biology, 2002, 189(3), 225); inflammatory bowel disease, irritable bowel syndrome, (Hoffman et al. Scandinavian Journal of Gastroenterology, 2002, 37(4) 414-422) and cystitis. Of particular importance is the acute or prophylactic treatment of headache, including migraine and cluster headache.

The present invention relates to compounds that are useful as ligands for CGRP receptors, in particular antagonists for CGRP receptors, their use in therapy, pharmaceutical compositions comprising them and methods of therapy using them.

SUMMARY OF THE INVENTION

The present invention is directed to compounds of the formula I:

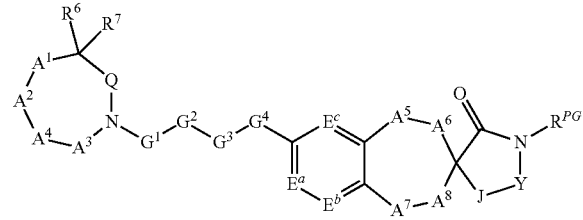

(wherein variables $A^1, A^2, A^3, A^4, A^5, A^6, A^7, A^8, G^1, G^2, G^3, G^4, J, Q, E^a, E^b, E^c, R^6, R^7, R^{PG}$ and Y are as described herein) which are antagonists of CGRP receptors and which are useful in the treatment or prevention of diseases in which CGRP is involved, such as migraine. The invention is also directed to pharmaceutical compositions comprising these compounds and the use of these compounds and compositions in the prevention or treatment of such diseases in which CGRP is involved.

DETAILED DESCRIPTION OF THE INVENTION

The present invention is directed to compounds of the formula I:

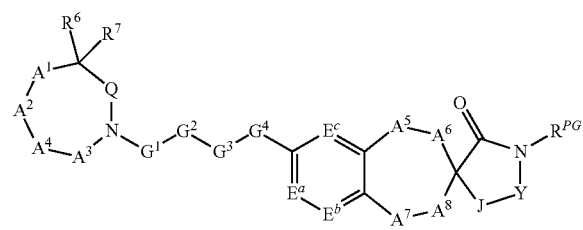

wherein:
$A^1$ is selected from:
 (1) —O—,
 (2) —S(O)$_v$—,
 (3) —Si(OR$^a$)(C$_{1-4}$alkyl)-, where alkyl is unsubstituted or substituted with 1-5 halo,
 (4) —Si(C$_{1-4}$alkyl)$_2$—, where each alkyl is independently unsubstituted or substituted with 1-5 halo-,
 (5) —CR$^6$R$^7$—,
 (6) —N(R$^8$)—,
 (7) —(C=O)—,
 (8) —C(R$^8$)(R$^a$)—,
 (9) —C(N(R$^b$)—SO$_2$R$^d$)(R$^a$)—,
 (10) —C(N(R$^b$)(C=O)R$^a$)(R$^a$)—,
 (11) —C(N(R$^b$)(C=O)OR$^a$)(R$^a$)—,
 (12) —CR$^{10}$R$^{11}$—, and
 (13) —N(R$^{11}$)—;

$A^2$ is selected from:
 (1) —CR$^6$R$^7$—,
 (2) —CR$^{10}$R$^{11}$—, and
 (3) —(C=O)—;
$A^3$ is selected from:
 (1) —CR$^6$R$^7$—,
 (2) —N(R$^8$)—,
 (3) —CR$^{10}$R$^{11}$—, and
 (4) —N(R$^{11}$)—;
$A^4$ is selected from:
 (1) —CR$^6$R$^7$—,
 (2) —(C=O)—,
 (3) —N(R$^8$)—,
 (4) —CR$^{10}$R$^{11}$—,
 (5) —N(R$^{11}$)—, and
 (6) a bond between $A^2$ and $A^3$;
$A^5$ and $A^7$ are independently selected from:
 (1) —O—,
 (2) —S(O)$_v$—,
 (3) —Si(OR$^a$)—C$_{1-4}$alkyl-, where alkyl is unsubstituted or substituted with 1-5 halo,
 (4) —Si(C$_{1-4}$alkyl)$_2$—, where each alkyl is independently unsubstituted or substituted with 1-5 halo-,
 (5) —CR$^e$R$^f$—,
 (6) —N(R$^8$)—,
 (7) —(C=O)—, and
 (8) a bond,
$A^6$ and $A^8$ are independently selected from:
 (1) —O—,
 (2) —S(O)$_v$—,
 (3) —Si(OR$^a$)—C$_{1-4}$alkyl-, where alkyl is unsubstituted or substituted with 1-5 halo,
 (4) —Si(C$_{1-4}$alkyl)$_2$—, where each alkyl is independently unsubstituted or substituted with 1-5 halo-,
 (5) —CR$^e$R$^f$—,
 (6) —N(R$^8$)—, and
 (7) —(C=O)—,
$E^a$ is selected from:
 (1) —C(R$^{5a}$)=,
 (2) —N=, and
 (3) —(N$^+$—O$^-$)=;
$E^b$ is selected from:
 (1) —C(R$^{5b}$)=,
 (2) —N=, and
 (3) —(N$^+$—O$^-$)=;
$E^c$ is selected from:
 (1) —C(R$^{5c}$)=,
 (2) —N=, and
 (3) —(N$^+$—O$^-$)=;
$G^1$ is selected from:
 (1) a bond,
 (2) —CR$^e$R$^f$—,
 (3) —CR$^e$R$^f$—CH$_2$—,
 (4) —CH$_2$—CR$^e$R$^f$—, and
 (5) —(C=O)—;
$G^2$ is selected from:
 (1) a bond,
 (2) —CR$^e$R$^f$—,
 (3) —CR$^e$R$^f$—CH$_2$—,
 (4) —CH$_2$—CR$^e$R$^f$—,
 (5) —(C=O)—,
 (6) —N(R$^8$)—,
 (7) —O—,
 (8) —S(O)$_v$—,
 (9) —SiR$^g$R$^h$—,
 (10) —C(R$^i$)=C(R$^j$)—, and
 (11) —C≡C—;

$G^3$ is selected from:
  (1) —$CR^eR^f$—,
  (2) —$N(R^8)$—,
  (3) —O—,
  (4) —$S(O)_v$—,
  (5) —$SiR^gR^h$—,
  (6) —(C=O)—,
  (7) —$C(R^i)$=$C(R^j)$—, and
  (8) —C≡C—,
  and $G^3$ is not —(C=O)— if $G^4$ is —$N(R^8)$—;
$G^4$ is selected from:
  (1) —$CR^eR^f$—,
  (2) —$N(R^8)$—,
  (3) —O—,
  (4) —$S(O)_v$—,
  (5) —$SiR^gR^h$—,
  (6) —(C=O)—,
  (7) —$C(R^i)$=$C(R^j)$—, and
  (8) —C≡C—;
Q is selected from:
  (1) —(C=O)—,
  (2) —$SO_2$—,
  (3) —SO—, and
  (4) —$C(R^a)_2$—;
$R^{5a}$, $R^{5b}$ and $R^{5c}$ are each independently selected from:
  (1) hydrogen,
  (2) —$C_{1-6}$alkyl, which is unsubstituted or substituted with 1-6 halo,
  (3) halo,
  (4) —$OR^a$, and
  (5) —CN;
$R^6$ and $R^7$ are each independently selected from:
  (1) hydrogen,
  (2) —$C_{1-6}$alkyl, which is unsubstituted or substituted with 1-5 substituents each independently selected from:
    (a) halo,
    (b) —$OR^a$,
    (c) —$C_{3-6}$cycloalkyl,
    (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl, indolyl, indazolyl, benzimidazolyl, and oxazolyl, which phenyl or heterocycle is unsubstituted or substituted with 1-5 substituents each independently selected from:
      (i) halo,
      (ii) —$C_{1-6}$alkyl, which is unsubstituted or substituted with 1-5 halo,
      (iii) —$OR^a$,
      (iv) —$NR^bR^c$,
      (v) —CN, and
      (vi) oxo;
    (e) —$CO_2R^a$,
    (f) —$C(=O)NR^bR^c$,
    (g) —$S(O)_vR^d$,
    (h) —CN,
    (i) —$NR^bR^c$,
    (j) —$N(R^b)C(=O)R^a$,
    (k) —$N(R^b)SO_2R^d$,
    (l) —$CF_3$,
    (m) —O—$CO_2R^d$,
    (n) —O—(C=O)—$NR^bR^c$,
    (o) —$NR^b$—(C=O)—$NR^bR^c$, and
    (p) —$C(=O)R^a$,
  (3) —$C_{3-8}$cycloalkyl, which is unsubstituted or substituted with 1-5 substituents each independently selected from:
    (a) halo,
    (b) —CN,
    (c) —$C_{1-4}$alkyl, which is unsubstituted or substituted with 1-3 halo, and
    (d) —$OR^a$,
  (4) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (a) halo,
    (b) —$OR^a$,
    (c) —$C_{3-6}$cycloalkyl,
    (d) phenyl, which is unsubstituted or substituted with 1-5 substituents each independently selected from:
      (i) halo,
      (ii) —$C_{1-6}$alkyl, which is unsubstituted or substituted with 1-6 halo, and
      (iii) —$OR^a$,
    (e) —$CO_2R^a$,
    (f) —$C(=O)NR^bR^c$,
    (g) —$S(O)_vR^d$,
    (h) —CN,
    (i) —$NR^bR^c$,
    (j) —$N(R^b)C(=O)R^a$,
    (k) —$N(R^b)SO_2R^d$,
    (l) —O—$CO_2R^d$,
    (m) —O—(C=O)—$NR^bR^c$,
    (n) —$NR^b$—(C=O)—$NR^bR^c$,
    (o) —$C(=O)R^a$,
    (p) —$C_{1-6}$alkyl, which is unsubstituted or substituted with 1-6 halo, and
    (q) oxo;
  (5) halo,
  (6) —$OR^a$,
  (7) —CN,
  (8) —$CO_2R^a$,
  (9) —$N(R^b)C(=O)R^a$,
  (10) —$NR^bR^c$,
  (11) —$C(=O)NR^bR^c$, and
  (12) —$O(C=O)R^a$;
or $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooctenyl, dioxolanyl, dioxanyl, aziridinyl, azetidinyl, pyrrolidinyl, piperidinyl, piperazinyl, morpholinyl, tetrahydrofuranyl, tetrahydropyranyl, tetrahydrothiapyranyl, oxetanyl, thietanyl and tetrahydrothienyl, wherein the sulfur is optionally oxidized to the sulfone or sulfoxide, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) —$CO_2R^a$,
    (v) —$NR^bR^c$,
    (vi) —$S(O)_vR^d$,
    (vii) —$C(=O)NR^bR^c$, and
    (viii) phenyl,
  (b) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from:
(i) halo,
(ii) —OR$^a$,
(iii) —C$_{3-6}$cycloalkyl,
(iv) —CO$_2$R$^a$,
(v) —NR$^b$R$^c$,
(vi) —S(O)$_v$R$^d$,
(vii) —C(=O)NR$^b$R$^c$, and
(viii) phenyl,
(c) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, imidazolyl, furanyl, tetrahydrofuranyl, thiazolyl and oxazolyl, wherein the phenyl or heterocycle is optionally fused to the ring, and which phenyl or heterocycle is unsubstituted or substituted with 1-5 substituents each independently selected from:
(i) halo,
(ii) —C$_{1-6}$alkyl, which is unsubstituted or substituted with 1-5 halo,
(iii) —OR$^a$,
(iv) —CO$_2$R$^a$,
(v) —O(C=O)R$^a$,
(vi) —CN,
(vii) —NR$^b$R$^c$,
(viii) oxo,
(ix) —C(=O)NR$^b$R$^c$,
(x) —N(R$^b$)C(=O)R$^a$,
(xi) —N(R$^b$)CO$_2$R$^a$,
(xii) —O(C=O)NR$^b$R$^c$, and
(xiii) —S(O)$_v$R$^d$,
(d) —OR$^a$,
(e) —CO$_2$R$^a$,
(f) —C(=O)NR$^b$R$^c$,
(g) —S(O)$_v$R$^d$,
(h) —CN,
(i) halo,
(j) —NR$^b$R$^c$,
(k) —N(R$^b$)C(=O)R$^a$,
(l) —N(R$^b$)SO$_2$R$^d$,
(m) —O—CO$_2$R$^d$,
(n) —O—(C=O)—NR$^b$R$^c$,
(o) —NR$^b$—(C=O)—NR$^b$R$^c$,
(p) —C(=O)R$^a$, and
(q) oxo;
R$^8$ is independently selected from:
(1) hydrogen,
(2) —C(=O)R$^a$,
(3) —CO$_2$R$^a$,
(4) —S(=O)R$^d$,
(5) —SO$_2$R$^d$,
(6) —C(=O)NR$^b$R$^c$,
(7) —C$_{1-6}$alkyl, which is unsubstituted or substituted with 1-5 substituents each independently selected from:
(a) halo,
(b) —OR$^a$,
(c) —C$_{3-6}$cycloalkyl,
(d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
(i) halo,
(ii) —C$_{1-6}$alkyl, which is unsubstituted or substituted with 1-5 halo, and
(iii) —OR$^a$,
(iv) —NR$^b$R$^c$,
(v) —C(=O)R$^a$,
(vi) —CO$_2$R$^a$, and
(vii) oxo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(R$^b$)C(=O)R$^a$,
(k) —N(R$^b$)SO$_2$R$^d$,
(l) —CF$_3$,
(m) —O—CO$_2$R$^d$,
(n) —O—(C=O)—NR$^b$R$^c$,
(o) —NR$^b$—(C=O)—NR$^b$R$^c$, and
(p) —C(=O)R$^a$,
(8) —C$_{3-6}$cycloalkyl, which is unsubstituted or substituted with 1-6 substituents each independently selected from:
(a) halo,
(b) —CN,
(c) —OR$^a$, and
(d) C$_{1-6}$alkyl, which is unsubstituted or substituted with 1-6 halo;
or R$^7$ and R$^8$ and the atoms to which they are attached join to form a 4-, 5-, 6- or 7-membered alkyl- or heteroalkyl- ring optionally containing an additional heteroatom selected from N, O, and S, wherein the sulfur is optionally oxidized to the sulfone or sulfoxide, which ring is unsubstituted or substituted with 1-4 substituents each independently selected from:
(a) halo,
(b) phenyl, which is unsubstituted or substituted with 1-3 substituents each independently selected from: halo, OR$^a$, CN, and —C(=O)OR$^a$,
(c) —OR$^a$, and
(d) —C$_{1-6}$alkyl, which is unsubstituted or substituted with 1-6 halo;
R$^{10}$ is independently selected from:
(1) hydrogen,
(2) —C$_{1-6}$alkyl, which is unsubstituted or substituted with 1-5 substituents each independently selected from:
(a) halo,
(b) —OR$^a$,
(c) —CN,
(d) phenyl, and
(e) —C$_{3-6}$cycloalkyl, which is unsubstituted or substituted with 1-6 halo,
(3) —C$_{3-6}$cycloalkyl, which is unsubstituted or substituted with 1-6 halo;
R$^{11}$ is independently selected from the group consisting of:
phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, 1,3-benzodioxolyl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, where $R^{11}$ is unsubstituted or substituted with 1-5 substituents each independently selected from $R^{12}$, $R^{13}$, $R^{14}$, $R^{15a}$ and $R^{15b}$;

$R^{12}$, $R^{13}$, $R^{14}$, $R^{15a}$ and $R^{15b}$ are each independently selected from:
(1) —$C_{1-6}$alkyl, which is unsubstituted or substituted with 1-5 substituents each independently selected from:
  (a) halo,
  (b) —$OR^a$,
  (c) —$C_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —$C_{1-6}$alkyl, which is unsubstituted or substituted with 1-5 halo, and
    (iii) —$OR^a$,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —$CF_3$,
  (m) —O—$CO_2R^d$,
  (n) —O—(C=O)—$NR^bR^c$,
  (o) —$NR^b$—(C=O)—$NR^bR^c$, and
  (p) —$C(=O)R^a$,
(2) —$C_{1-6}$cycloalkyl, which is unsubstituted or substituted with 1-5 substituents each independently selected from:
  (a) halo,
  (b) —CN,
  (c) —$C_{1-6}$alkyl, which is unsubstituted or substituted with 1-5 halo,
  (d) —$OR^a$, and
  (e) phenyl, which is unsubstituted or substituted with 1-5 substituents where the substituents are each independently selected from:
    (i) —$OR^a$,
    (ii) halo,
    (iii) —CN, and
    (iv) —$C_{1-6}$alkyl, which is unsubstituted or substituted with 1-5 halo,
(3) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
  (a) halo,
  (b) —$OR^a$,
  (c) —$C_{3-6}$cycloalkyl,
  (d) phenyl, which is unsubstituted or substituted with 1-5 substituents each independently selected from:
    (i) halo,
    (ii) —$C_{1-6}$alkyl, which is unsubstituted or substituted with 1-6 halo, and
    (iii) —$OR^a$,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(R^b)C(=O)R^a$,
  (k) —$N(R^b)SO_2R^d$,
  (l) —O—$CO_2R^d$,
  (m) —O—(C=O)—$NR^bR^c$,
  (n) —$NR^b$—(C=O)—$NR^bR^c$,
  (o) —$C(=O)R^a$, and
  (p) —$C_{1-6}$alkyl, which is unsubstituted or substituted with 1-6 halo,
(4) halo,
(5) oxo,
(6) —$OR^a$,
(7) —CN,
(8) —$CO_2R^a$,
(9) —$C(=O)R^a$,
(10) —$NR^bR^c$,
(11) —$S(O)_vR^d$,
(12) —$C(=O)NR^bR^c$,
(13) —O—$CO_2R^d$,
(14) —$N(R^b)CO_2R^d$,
(15) —O—(C=O)—$NR^bR^c$,
(16) —$NR^b$—(C=O)—$NR^bR^c$,
(17) —$SO_2NR^bR^c$,
(18) —$N(R^b)SO_2R^d$,
or $R^{15a}$ and $R^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is unsubstituted or substituted with 1-5 substituents each independently selected from:
  (a) —$C_{1-6}$alkyl, which is unsubstituted or substituted with 1-3 substituents each independently selected from:
    (i) halo,
    (ii) —$OR^a$,
    (iii) —$C_{3-6}$cycloalkyl,
    (iv) —$CO_2R^a$,
    (v) —$NR^bR^c$,
    (vi) —$S(O)_vR^d$,
    (vii) —$C(=O)NR^bR^c$, and
    (viii) phenyl,
  (b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from:
    (i) halo,
    (ii) —$C_{1-6}$alkyl, which is unsubstituted or substituted with 1-5 halo, and
    (iii) —$OR^a$,
  (c) —$OR^a$,
  (d) halo, (e) —CO$_2$R$^a$,
(f) —C(=O)NR$^b$R$^c$,
(g) —S(O)$_x$R$^d$,
(h) —CN,
(i) —NR$^b$R$^c$,
(j) —N(R$^b$)C(=O)R$^a$,
(k) —N(R$^b$)SO$_2$R$^d$,
(l) —O—CO$_2$R$^d$,
(m) —O—(C=O)—NR$^b$R$^c$,
(n) —NR$^b$—(C=O)—NR$^b$R$^c$, and
(o) —C(=O)R$^a$;

R$^{PG}$ is independently selected from:
(1) hydrogen,
(2) —C$_{1-6}$alkyl which is unsubstituted or substituted with 1-5 halo,
(3) —CH$_2$OR$^a$,
(4) —CH$_2$—O—CH$_2$CH$_2$Si(CH$_3$)$_3$,
(5) —CH$_2$OP(=O)(OR$^c$)$_2$,
(6) —(CH$_2$)$_k$-phenyl, which is unsubstituted or substituted with 1-3 substituents each independently selected from:
 (a) halo,
 (b) —OR$^a$,
 (c) —CN, and
 (d) —C$_{1-6}$alkyl, which is unsubstituted or substituted with 1-6 halo;

J is independently selected from:
(1) =C(R$^{16a}$)—,
(2) —CR$^{17}$R$^{18}$—,
(3) —C(=O)—, and
(4) —N(R$^b$)—;

Y is independently selected from:
(1) =C(R$^{16b}$)—,
(2) —CR$^{17}$R$^{18}$—,
(3) —C(=O)—,
(4) =N—, and
(5) —N(R$^{16b}$)—;

R$^{17}$ and R$^{18}$ are each independently selected from:
(1) hydrogen,
(2) halo,
(3) —OR$^a$,
(4) —C$_{1-6}$alkyl, which is unsubstituted or substituted with 1-4 substituents each independently selected from:
 (a) halo,
 (b) —OR$^a$,
 (c) —CN,
 (d) phenyl or heterocycle, wherein said heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
  (i) —OR$^a$,
  (ii) halo,
  (iii) —CN,
  (iv) —C$_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from:
 (a) halo,
 (b) —CN,
 (c) —OR$^a$,
 (d) nitro,
 (e) —C$_{1-6}$alkyl which is unsubstituted or substituted with 1-6 halo;

or R$^{17}$ and R$^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —OR$^a$,
(c) —C$_{1-6}$alkyl, which is unsubstituted or substituted with 1-6 halo, and
(d) phenyl;

R$^{16a}$ and R$^{16b}$ are each independently selected from:
(1) hydrogen,
(2) —C$_{1-4}$alkyl, which is unsubstituted or substituted with 1-5 substituents each independently selected from:
 (a) halo,
 (b) —OR$^a$,
 (c) —C$_{3-6}$cycloalkyl,
 (d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from:
  (i) halo,
  (ii) —OR$^a$,
  (iii) —CN, and
  (iv) C$_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from:
 (a) halo,
 (b) —OR$^a$,
 (c) —C$_{3-6}$cycloalkyl,
 (d) —C$_{1-4}$alkyl which is unsubstituted or substituted with 1-6 halo, and
 (e) phenyl, which is unsubstituted or substituted with 1-5 substituents each independently selected from:
  (i) halo,
  (ii) —C$_{1-6}$alkyl, which is unsubstituted or substituted with 1-6 halo, and
  (iii) —OR$^a$,
(4) halo,
(5) —OR$^a$,
(6) —CN,
(7) —CO$_2$R$^a$,
(8) —NR$^b$R$^c$, and
(9) —C(=O)NR$^b$R$^c$;

or R$^{16a}$ and R$^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from:

(a) —C$_{1-6}$alkyl, which is unsubstituted or substituted with 1-3 substituents each independently selected from:
  (i) halo,
  (ii) —OR$^a$,
  (iii) —C$_{3-6}$cycloalkyl,
  (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from:
    (I) —OR$^a$,
    (II) halo,
    (III) —CN, and
    (IV) —C$_{1-6}$alkyl which is unsubstituted or substituted with 1-6 halo,
  (v) —CO$_2$R$^a$,
  (vi) —NR$^b$R$^c$,
  (vii) —S(O)$_v$R$^d$,
  (viii) —C(=O)NR$^b$R$^c$,
  (ix) —N(R$^b$)CO$_2$R$^a$, and
  (x) —N(R$^b$)SO$_2$R$^d$,
(b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from:
  (i) halo,
  (ii) —OR$^a$,
  (iii) —CN, and
  (iv) —C$_{1-6}$alkyl which is unsubstituted or substituted with 1-6 halo,
(c) halo,
(d) —S(O)$_v$R$^d$,
(e) —OR$^a$,
(f) —CN,
(g) —C(=O)R$^a$,
(h) —NR$^b$R$^c$,
(i) —C(=O)NR$^b$R$^c$,
(j) —CO$_2$R$^a$,
(k) —(NR$^b$)CO$_2$R$^a$,
(l) —O—(C=O)—NR$^b$R$^c$,
(m) —(NR$^b$)—(C=O)—NR$^b$R$^c$,
(n) oxido,
(o) oxo, and
(p) —(NR$^b$)SO$_2$R$^d$;
R$^a$ is independently selected from:
(1) hydrogen,
(2) C$_{1-6}$alkyl, which is unsubstituted or substituted with 1-7 substituents each independently selected from:
  (a) halo,
  (b) —O—C$_{1-6}$alkyl, which is unsubstituted or substituted with 1-6 halo,
  (c) hydroxyl,
  (d) —CN, and
  (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —O—C$_{1-6}$alkyl, which is unsubstituted or substituted with 1-6 halo,
    (iii) —CN,
    (iv) nitro,
    (v) hydroxyl, and
    (vi) —C$_{1-6}$alkyl, which is unsubstituted or substituted with 1-6 halo,
  (3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —CN,
    (c) —O—C$_{1-6}$alkyl, which is unsubstituted or substituted with 1-6 halo,
    (d) nitro,
    (e) hydroxyl, and
    (f) —C$_{1-6}$alkyl, which is unsubstituted or substituted with 1-6 halo, and
  (4) —C$_{3-6}$cycloalkyl, which is unsubstituted or substituted with 1-6 halo;
R$^b$ and R$^c$ are independently selected from:
(1) hydrogen,
(2) C$_{1-6}$alkyl, which is unsubstituted or substituted with 1-7 substituents each independently selected from:
  (a) halo,
  (b) —OR$^a$,
  (c) —CN,
  (d) —CO$_2$R$^a$,
  (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (i) halo,
    (ii) —OR$^a$,
    (iii) —C$_{1-6}$alkyl, which is unsubstituted or substituted with 1-6 halo, and
    (iv) nitro,
  (3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
    (a) halo,
    (b) —OR$^a$,
    (c) —C$_{1-6}$alkyl, which is unsubstituted or substituted with 1-6 halo,
    (d) —C$_{3-6}$cycloalkyl, which is unsubstituted or substituted with 1-6 halo,
    (e) —CN, and
    (f) —CO$_2$R$^a$,
(4) —C$_{3-6}$cycloalkyl, which is unsubstituted or substituted with 1-6 halo; or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from:
  (a) halo,
  (b)—OR$^a$, and (c) —$C_{1-6}$alkyl, which is unsubstituted or substituted with 1-6 halo, and
(d) phenyl;
$R^d$ is independently selected from:
(1) $C_{1-6}$alkyl, which is unsubstituted or substituted with 1-4 substituents each independently selected from:
(a) halo,
(b) —$OR^a$,
(c) —$CO_2R^a$,
(d) —CN, and
(e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(i) halo,
(ii) —$OR^a$,
(iii) —$C_{1-6}$alkyl, which is unsubstituted or substituted with 1-6 halo, and
(iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from:
(a) halo,
(b) —$OR^a$,
(c) —$C_{1-6}$alkyl, which is unsubstituted or substituted with 1-6 halo,
(d) —$C_{3-6}$cycloalkyl, which is unsubstituted or substituted with 1-6 halo
(e) —CN, and
(f) —$CO_2R^a$, and
(3) —$C_{3-6}$cycloalkyl, which is unsubstituted or substituted with 1-6 halo;
$R^e$ and $R^f$ are independently selected from:
(1) hydrogen,
(2) —$C_{1-4}$alkyl, which is unsubstituted or substituted with 1-6 halo,
(3) —$OR^a$,
(4) —CN,
(5) halo,
(6) phenyl, and
(7) benzyl;
or where $R^e$ and $R^f$ and the carbon atom or atoms to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^a$,
(c) —$C_{1-6}$alkyl, which is unsubstituted or substituted with 1-6 halo, and
(d) phenyl;
$R^g$ and $R^h$ are independently selected from:
(1) —$C_{1-4}$alkyl, which is unsubstituted or substituted with 1-6 halo,
(2) —$OR^a$,
(3) —$C_{3-6}$cycloalkyl, which is unsubstituted or substituted with 1-6 halo,
(4) phenyl, and
(5) benzyl;
or where $R^g$ and $R^h$ and the silicon atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from:
(a) halo,
(b) —$OR^a$,
(c) —$C_{1-4}$alkyl, which is unsubstituted or substituted with 1-3 halo, and
(d) phenyl;
$R^i$ and $R^j$ are independently selected from:
(1) hydrogen,
(2) —$C_{1-4}$alkyl, which is unsubstituted or substituted with 1-6 halo,
(3) halo,
(4) phenyl, and
(5) benzyl;
v is 0, 1, or 2;
k is 0, 1, or 2;
and pharmaceutically acceptable salts thereof and individual enantiomers and diastereomers thereof.

An embodiment of the invention includes compounds of formula Ia:

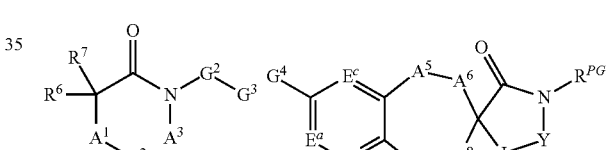

Ia wherein $A^1, A^2, A^3, A^5, A^6, A^7, A^8, J, Y, G^2, G^3, G^4, E^a, E^b, E^c$, $R^6, R^7$, and $R^{PG}$ are defined herein;

and pharmaceutically acceptable salts thereof and individual enantiomers and diastereomers thereof.

Another embodiment of the invention includes compounds of formula Ib:

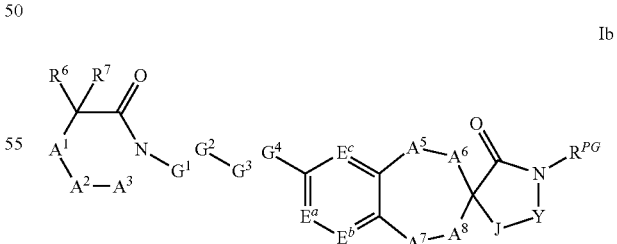

Ib wherein $A^1, A^2, A^3, A^5, A^6, A^7, A^8, J, Y, G^1, G^2, G^3, G^4, E^a, E^b$, $E^c, R^6, R^7$, and $R^{PG}$ are defined herein;

and pharmaceutically acceptable salts thereof and individual enantiomers and diastereomers thereof.

Another embodiment of the invention includes compounds of formula Ic:

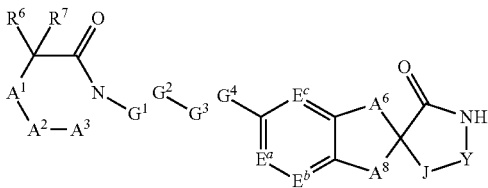

Ic wherein $A^1, A^2, A^3, A^6, A^8, J, Y, G^1, G^2, G^3, G^4, E^a, E^b, E^c, R^6$, and $R^7$ are defined herein;
and pharmaceutically acceptable salts thereof and individual enantiomers and diastereomers thereof.

Another embodiment of the invention includes compounds of formula Id:

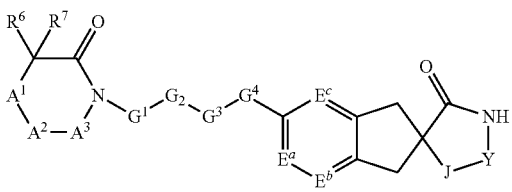

Id wherein $A^1, A^2, A^3, J, Y, G^1, G^2, G^3, G^4, E^a, E^b, E^c, R^6$, and $R^7$ are defined herein;
and pharmaceutically acceptable salts thereof and individual enantiomers and diastereomers thereof.

Another embodiment of the invention includes compounds of formula Ie:

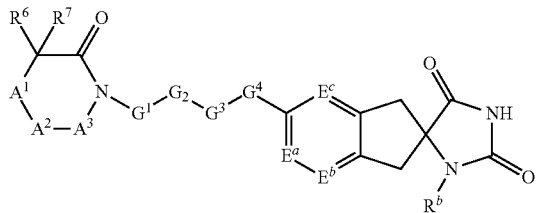

Ie wherein $A^1, A^2, A^3, G^1, G^2, G^3, G^4, E^a, E^b, E^c, R^b, R^6$, and $R^7$ are defined herein;
and pharmaceutically acceptable salts thereof and individual enantiomers and diastereomers thereof.

Another embodiment of the invention includes compounds of formula If:

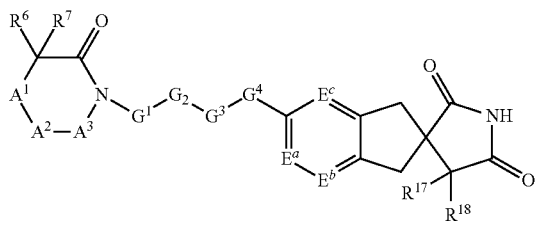

If wherein $A^1, A^2, A^3, G^1, G^2, G^3, G^4, E^a, E^b, E^c, R^6, R^7, R^{17}$ and $R^{18}$ are defined herein;
and pharmaceutically acceptable salts thereof and individual enantiomers and diastereomers thereof.

Another embodiment of the invention includes compounds of formula Ig:

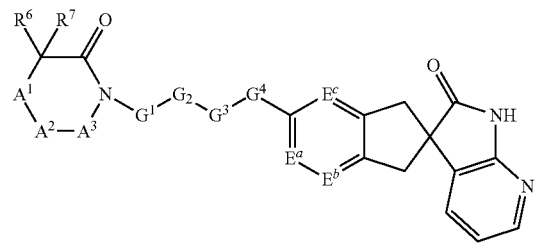

Ig wherein $A^1, A^2, A^3, G^1, G^2, G^3, G^4, E^a, E^b, E^c, R^6$ and $R^7$ are defined herein;
and pharmaceutically acceptable salts thereof and individual enantiomers and diastereomers thereof.

Another embodiment of the invention includes compounds of formula Ih:

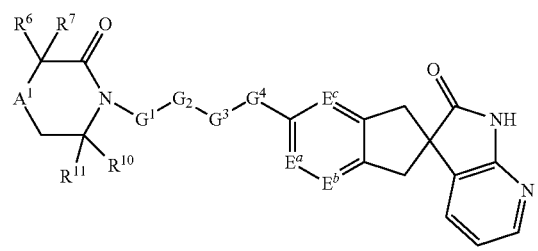

Ih wherein $A^1, G^1, G^2, G^3, G^4, E^a, E^b, E^c, R^6, R^7, R^{10}$ and $R^{11}$ are defined herein;
and pharmaceutically acceptable salts thereof and individual enantiomers and diastereomers thereof.

In an embodiment of the present invention $A^1$ is independently selected from:
(1) —O—,
(2) —S(O)$_v$—,
(3) —CR$^6$R$^7$—,
(4) —N(R$^8$)—,
(5) —(C=O)—,
(6) —C(R$^8$)(R$^a$)—,
(7) —C(N(R$^b$)—SO$_2$R$^d$)(R$^a$)—,
(8) —C(N(R$^b$)(C=O)R$^a$)(R$^a$)—,
(9) —C(N(R$^b$)(C=O)OR$^a$)(R$^a$)—,
(10) —CR$^{10}$R$^{11}$—, and
(11) —N(R$^{11}$)—, wherein v, $R^6, R^7, R^8, R^a, R^b, R^c, R^d, R^{10}$ and $R^{11}$ are defined herein.

In an embodiment of the present invention $A^1$ is independently selected from:
(1) —O—,
(2) —S(O)$_v$—,
(3) —CR$^6$R$^7$—,
(4) —N(R$^8$)—,
(5) —C(N(R$^b$)(C=O)OR$^a$)(R$^a$)—,
(6) —(C=O)—, and (7) —N($R^{11}$)—, wherein v, $R^6$, $R^7$, $R^8$, $R^a$, $R^b$, $R^c$ and $R^{11}$ are defined herein.

In an embodiment of the present invention $A^1$ is —O—.

In an embodiment of the present invention $A^1$ is —S(O)$_v$—, wherein v is defined herein.

In an embodiment of the present invention $A^1$ is —$CR^6R^7$—, wherein $R^6$ and $R^7$ are defined herein.

In an embodiment of the present invention $A^1$ is $CH_2$.

In an embodiment of the present invention $A^1$ is —N($R^8$)—, wherein $R^8$ is defined herein.

In an embodiment of the present invention $A^1$ is —NH—.

In an embodiment of the present invention $A^1$ is —C(O$R^a$)H—, wherein $R^a$ is defined herein.

In an embodiment of the present invention $A^1$ is —C(=O)—.

In an embodiment of the present invention $A^1$ is —C(N$R^b R^c$)H—, wherein $R^b$ and $R^c$ are defined herein.

In an embodiment of the present invention $A^1$ is —C(N($R^b$))(C=O)O$R^a$)H—, wherein $R^a$ and $R^b$ are defined herein.

In an embodiment of the present invention $A^2$ is independently selected from:
(1) —$CR^6R^7$—, and
(2) —$CR^{10}R^{11}$—, wherein $R^6$, $R^7$, $R^{10}$ and $R^{11}$ are defined herein.

In an embodiment of the present invention $A^2$ is —$CR^6R^7$—, wherein $R^6$ and $R^7$ are defined herein.

In an embodiment of the present invention $A^2$ is —$CH_2$—.

In an embodiment of the present invention $A^2$ is —(C=O)—.

In an embodiment of the present invention $A^3$ is independently selected from:
(1) —$CR^6R^7$—,
(2) —$CR^{10}R^{11}$—, and
(3) —N($R^{11}$)—, wherein $R^6$, $R^7$, $R^{10}$ and $R^{11}$ are defined herein.

In an embodiment of the present invention $A^3$ is —$CR^6R^7$—, wherein $R^6$ and $R^7$ are defined herein.

In an embodiment of the present invention $A^3$ is —$CR^{10}R^{11}$—, wherein $R^{10}$ and $R^{11}$ are defined herein.

In an embodiment of the present invention $A^4$ is independently selected from:
(1) —$CR^6R^7$—,
(2) —$CR^{10}R^{11}$—,
(3) —N($R^{11}$)—,
(4) —N($R^8$)—, and
(4) a bond between $A^2$ and $A^3$, wherein $R^6$, $R^7$, $R^8$, $R^{10}$ and $R^{11}$ are defined herein.

In an embodiment of the present invention $A^4$ is $CH_2$.

In an embodiment of the present invention $A^4$ is a bond between $A^2$ and $A^3$.

In an embodiment of the present invention $A^5$ is a bond.

In an embodiment of the present invention $A^6$ is —$CR^e R^f$—.

In an embodiment of the present invention $A^6$ is $CH_2$.

In an embodiment of the present invention $A^7$ is a bond.

In an embodiment of the present invention $A^8$ is —$CR^e R^f$—.

In an embodiment of the present invention $A^8$ is $CH_2$.

In an embodiment of the present invention $G^1$ is a bond.

In an embodiment of the present invention $G^2$ is a bond.

In an embodiment of the present invention $G^2$ is $CH_2$.

In an embodiment of the present invention -$G^2$-$G^3$-$G^4$- is selected from the group consisting of:
—$CH_2$—$CH_2$—$CH_2$—,
$CH_2$—CH=CH—,
—$CH_2$—C≡C—,
—$CH_2$—$CH_2$—S—,
—$CH_2$—$CH_2$—S(=O)—,
—$CH_2$—$CH_2$—(C=O)—,
—$CH_2$—(C=O)—O—, and
—$CH_2$—$CH_2$—O—.

In an embodiment of the present invention Ea is independently selected from:
(1) —C($R^{5a}$)=, and
(2) —N=, wherein $R^{5a}$ is defined herein.

In an embodiment of the present invention $E^a$ is —C($R^{5a}$)=, wherein $R^{5a}$ is defined herein.

In an embodiment of the present invention $E^a$ is —C(H)=.

In an embodiment of the present invention $E^a$ is —N=.

In an embodiment of the present invention $E^b$ is independently selected from:
(1) —C($R^{5b}$)=, and
(2) —N=, wherein $R^{5b}$ is defined herein.

In an embodiment of the present invention $E^b$ is —C($R^{5b}$)=, wherein $R^{5b}$ is defined herein.

In an embodiment of the present invention $E^b$ is —C(H)=.

In an embodiment of the present invention $E^b$ is —N=.

In an embodiment of the present invention $E^c$ is independently selected from:
(1) —C($R^{5c}$)=, and
(2) —N=, wherein $R^{5c}$ is defined herein.

In an embodiment of the present invention $E^c$ is —C($R^{5c}$)=, wherein $R^{5c}$ is defined herein.

In an embodiment of the present invention $E^c$ is —C(H)=.

In an embodiment of the present invention $E^c$ is —N=.

In an embodiment of the present invention Q is —(C=O)—.

In an embodiment of the present invention $R^{5a}$, $R^{5b}$ and $R^{5c}$ are independently selected from hydrogen, halo, and —$C_{1-6}$alkyl, which is unsubstituted or substituted with 1-5 fluoro.

In an embodiment of the present invention $R^{5a}$, $R^{5b}$ and $R^{5c}$ are independently selected from hydrogen, —CN, and halo.

In an embodiment of the present invention $R^{5a}$, $R^{5b}$ and $R^{5c}$ are hydrogen.

In an embodiment of the present invention $R^6$ and $R^7$ are independently selected from:
(1) hydrogen,
(2) —$C_{1-6}$alkyl, which is unsubstituted or substituted with 1-5 substituents where the substituents are each independently selected from: halo, phenyl, and —O$R^a$,
(3) —$C_{3-6}$cycloalkyl, which is unsubstituted or substituted with 1-5 fluoro,
(4) phenyl or heterocycle, which is unsubstituted or substituted with 1-5 halo, wherein heterocycle is defined herein,
(5) halo,
(6) —O$R^a$,
(7) —N$R^b R^c$, and
(8) —O(C=O)$R^a$, wherein $R^a$, $R^b$ and $R^c$ are defined herein.

In an embodiment of the present invention $R^6$ and $R^7$ are independently selected from:
(1) hydrogen,
(2) —$C_{1-6}$alkyl, which is unsubstituted or substituted with 1-5 fluoro,
(3) phenyl, which is unsubstituted or substituted with 1-5 halo, and
(4) halo,
(5) —O$R^a$, and
(6) —N$R^b R^c$, wherein $R^a$, $R^b$ and $R^c$ are defined herein.

In an embodiment of the present invention $R^6$ and $R^7$ are independently selected from hydrogen, OH and —$C_{1-6}$alkyl, which is unsubstituted or substituted with 1-5 fluoro.

In an embodiment of the present invention $R^6$ and $R^7$ are independently selected from hydrogen, —$NR^bR^c$ and —$C_{1-6}$alkyl, which is unsubstituted or substituted with 1-5 fluoro, wherein $R^b$ and $R^c$ are defined herein.

In an embodiment of the present invention $R^6$ and $R^7$ are independently selected from hydrogen, —$NH_2$ and —$C_{1-6}$alkyl, which is unsubstituted or substituted with 1-5 fluoro.

In an embodiment of the present invention $R^6$ and $R^7$ are independently selected from hydrogen and —$C_{1-6}$alkyl, which is unsubstituted or substituted with 1-5 fluoro.

In an embodiment of the present invention $R^6$ and $R^7$ are ethyl, which are unsubstituted or substituted with 1-5 fluoro.

In an embodiment of the present invention $R^6$ and $R^7$ are methyl, which are unsubstituted or substituted with 1-3 fluoro.

In an embodiment of the present invention $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclopentenyl, cyclohexenyl, cycloheptenyl, dioxolanyl, dioxanyl, tetrahydrofuranyl, tetrahydropyranyl, pyrrolidinyl, and piperidinyl, which ring is unsubstituted or substituted with 1-6 substituents each independently selected from:
(1) —$C_{1-6}$alkyl, which is unsubstituted or substituted with 1-3 substituents where the substituents are each independently selected from: halo, —$OR^a$, and phenyl,
(2) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from: halo, —$OR^a$, and phenyl,
(3) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-3 substituents each independently selected from: halo, —$OR^a$, and —$C_{1-4}$alkyl, which is unsubstituted or substituted with 1-5 fluoro,
(4) halo,
(5) oxo,
(6) —$CO_2R^a$, and
(7) —$C(=O)R^a$,
wherein $R^a$ is defined herein.

In an embodiment of the present invention $R^6$ and $R^7$ and the carbon atom or atoms to which they are attached join to form a ring selected from cyclopropyl, cyclobutyl, cyclopentyl, dioxolanyl, cyclohexyl, cycloheptyl, cyclopentenyl, cyclohexenyl, tetrahydropyranyl, pyrrolidinyl, and piperidinyl, which ring is unsubstituted or substituted with 1-6 substituents each independently selected from:
(1) —$C_{1-6}$ alkyl, which is unsubstituted or substituted with 1-3 substituents where the substituents are each independently selected from: halo, and —$OR^a$,
(2) phenyl or pyridyl, wherein the phenyl or pyridyl is optionally fused to the ring, and which phenyl or pyridyl is unsubstituted or substituted with 1-3 substituents each independently selected from: halo, —$OR^a$, and —$C_{1-4}$alkyl, which is unsubstituted or substituted with 1-5 fluoro,
(3) halo, and
(4) —$CO_2R^a$,
wherein $R^a$ is defined herein.

In an embodiment of the present invention $R^6$ and $R^7$ and the carbon atom or atoms to which they are attached join to form a ring selected from cyclopropyl, cyclobutyl, cyclopentyl, cyclohexyl, cycloheptyl, tetrahydropyranyl, pyrrolidinyl, and piperidinyl, which ring is unsubstituted or substituted with 1-6 substituents each independently selected from:
(1) —$C_{1-6}$ alkyl, which is unsubstituted or substituted with 1-3 halo,
(2) phenyl, wherein the phenyl is optionally fused to the ring, and which phenyl is unsubstituted or substituted with 1-3 substituents each independently selected from: halo, —$OR^a$, and —$C_{1-4}$alkyl, which is unsubstituted or substituted with 1-3 fluoro, and
(3) halo,
wherein $R^a$ is defined herein.

In an embodiment of the present invention $R^8$ is selected from: hydrogen, —$C(=O)R^a$, —$CO_2R^a$, —$SO_2R^d$, and —$C_{1-6}$alkyl, which is unsubstituted or substituted with 1-5 fluoro, wherein $R^a$ and $R^d$ are defined herein.

In an embodiment of the present invention $R^8$ is selected from: hydrogen, and —$C_{1-6}$alkyl, which is unsubstituted or substituted with 1-5 fluoro.

In an embodiment of the present invention $R^8$ is hydrogen.

In an embodiment of the present invention $R^8$ is methyl.

In an embodiment of the present invention $R^8$ and $R^7$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from:
(1) halo,
(2) phenyl, which is unsubstituted or substituted with 1-3 substituents each independently selected from: halo, $OR^a$, CN, and —$C(=O)OR^a$,
(3) —$OR^a$, and
(4) —$C_{1-6}$alkyl, which is unsubstituted or substituted with 1-6 halo, wherein $R^a$ is defined herein.

In an embodiment of the present invention $R^{10}$ is selected from: hydrogen, and —$C_{1-6}$alkyl, which is unsubstituted or substituted with fluoro.

In an embodiment of the present invention $R^{10}$ is hydrogen.

In an embodiment of the present invention $R^{11}$ is independently selected from the group consisting of:
phenyl, furanyl, pyrazinyl, pyridinyl, pyridyl, pyrimidinyl, pyrimidyl, tetrazolyl, thienyl, triazolyl, and isoxazolyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is independently selected from the group consisting of:
phenyl, pyridyl, and thienyl, where $R^{11}$ is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{11}$ is phenyl, which is unsubstituted or substituted with 1-5 substituents each independently selected from $R^{12}$, $R^{13}$, $R^{14}$, $R^{15a}$ and $R^{15b}$, wherein $R^{12}$, $R^{13}$, $R^{14}$, $R^{15a}$ and $R^{15b}$ are defined herein.

In an embodiment of the present invention $R^{PG}$ is selected from:
(1) hydrogen,
(2) —$C_{1-6}$ alkyl, which is unsubstituted or substituted with 1-3 halo,
(3) —$CH_2OR^a$, and
(4) —$CH_2$—O—$CH_2CH_2Si(CH_3)_3$,
(5) —$CH_2OP(=O)(OR^c)_2$,
wherein $R^a$ and $R^c$ are defined herein.

In an embodiment of the present invention $R^{PG}$ is selected from: hydrogen and —$C_{1-6}$alkyl, which is unsubstituted or substituted with 1-3 halo.

In an embodiment of the present invention $R^{PG}$ is methyl.

In an embodiment of the present invention $R^{PG}$ is hydrogen.

In an embodiment of the present invention J is =C($R^{16a}$)—, N($R^b$)—, wherein $R^{16a}$, $R^{17}$, $R^{18}$ and $R^b$ are defined herein.

In an embodiment of the present invention J is =C($R^{16a}$)—, wherein $R^{16a}$ is defined herein.

In an embodiment of the present invention J is —C$R^{17}R^{18}$—, wherein $R^{17}$ and $R^{18}$ are defined herein.

In an embodiment of the present invention J is —CH$_2$—.

In an embodiment of the present invention J is —N($R^b$)—, wherein $R^b$ is defined herein.

In an embodiment of the present invention J is —N(CH$_3$)—.

In an embodiment of the present invention Y is =C($R^{16b}$)—, —C$R^{17}R^{18}$— or —C(=O)—, wherein $R^{16b}$, $R^{17}$ and $R^{18}$ are defined herein.

In an embodiment of the present invention Y is =C($R^{16b}$)—, wherein $R^{16b}$ is defined herein.

In an embodiment of the present invention Y is —C(=O)—.

In an embodiment of the present invention $R^{16a}$ and $R^{16b}$ are independently selected from:
(1) hydrogen,
(2) —$C_{1-4}$alkyl, which is unsubstituted or substituted with 1-3 substituents each independently selected from: halo, —OR$^a$, —$C_{3-6}$cycloalkyl, and phenyl,
(3) phenyl or heterocycle, wherein heterocycle is selected from: pyridyl, pyrimidinyl, pyrazinyl, thiazolyl, thienyl, triazolyl, isoxazolyl and morpholinyl, which phenyl or heterocycle is unsubstituted or substituted with 1-3 substituents each independently selected from: —$C_{1-4}$alkyl which is unsubstituted or substituted with 1-3 halo, —OR$^a$, and halo,
(4) halo,
(5) OR$^a$, and
(6) —N$R^bR^c$, wherein $R^a$, $R^b$ and $R^c$ are defined herein.

In an embodiment of the present invention $R^{16a}$ and $R^{16b}$ are independently selected from:
(1) hydrogen,
(2) —$C_{1-4}$alkyl, which is unsubstituted or substituted with 1-3 fluoro, and
(3) phenyl or heterocycle, wherein heterocycle is selected from: pyridyl, pyrimidinyl, pyrazinyl, thiazolyl, thienyl, triazolyl, isoxazolyl and morpholinyl.

In an embodiment of the present invention $R^{16a}$ and $R^{16b}$ and the atom(s) to which they are attached join to form a ring selected from cyclohexenyl, phenyl, pyridyl, pyrimidinyl, pyrazinyl, pyridazinyl, furanyl, oxazolyl, isoxazolyl, imidazolyl, and thienyl, which ring is unsubstituted or substituted with 1-3 substituents each independently selected from:
(1) —$C_{1-6}$alkyl, which is unsubstituted or substituted with 1-3 substituents each independently selected from: halo, OR$^a$, —CO$_2$R$^a$, —N$R^bR^c$, and CON$R^bR^c$,
(2) phenyl or heterocycle, wherein heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-3 substituents each independently selected from: halo, OR$^a$ and —$C_{1-4}$ alkyl, which is unsubstituted or substituted with 1-3 fluoro,
(3) halo,
(4) OR$^a$,
(5) —CN,
(6) —N$R^bR^c$,
(7) CON$R^bR^c$, and
(8) oxo, wherein $R^a$, $R^b$ and $R^c$ are defined herein.

In an embodiment of the present invention $R^{16a}$ and $R^{16b}$ and the atom(s) to which they are attached join to form a ring selected from phenyl, pyridyl, and pyrimidinyl, which ring is unsubstituted or substituted with 1-3 substituents each independently selected from: halo, OR$^a$ and —$C_{1-4}$alkyl, which is unsubstituted or substituted with 1-3 fluoro, wherein $R^a$ is defined herein.

In an embodiment of the present invention $R^{16a}$ and $R^{16b}$ and the atom(s) to which they are attached join to form a ring selected from pyridyl, and pyrimidinyl.

It is to be understood that where one or more of the above recited structures or substructures recite multiple substituents having the same designation each such variable may be the same or different from each similarly designated variable. For example, if $R^8$ is recited multiple times in an embodiment of formula I, each instance of $R^8$ in formula I may independently be any of the substructures defined under $R^8$. The invention is not limited to structures and substructures wherein each $R^8$ must be the same for a given structure. The same is true with respect to any variable appearing multiple times in a structure or substructure.

In an embodiment, the invention encompasses compounds of Formula Ii

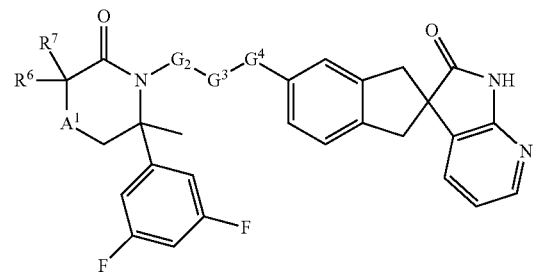

wherein $R^6$ and $R^7$ are each methyl or $R^6$ and $R^7$ are joined together with the atom to which they are attached to form a cyclopentyl ring;

$A^1$ is selected from the group consisting of:
(1) —CH$_2$—, and
(2) —N($R^8$)—, wherein $R^8$ is selected from H and $C_{1-6}$alkyl; and -G$^2$-G$^3$-G$^4$- is selected from the group consisting of:
—CH$_2$—CH$_2$—CH$_2$—,
—CH$_2$—CH=CH—,
—CH$_2$—C≡C— and
—CH$_2$—CH$_2$—O—;

and pharmaceutically acceptable salts thereof and individual enantiomers and diastereomers thereof.

In an embodiment, the invention encompasses compounds of Formula Ij

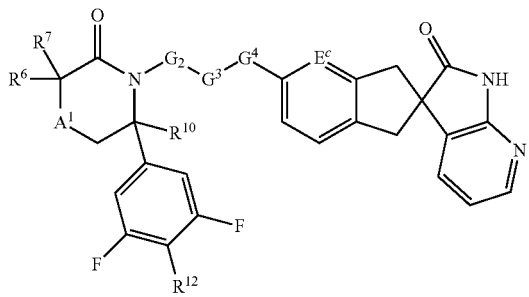

wherein $R^6$ and $R^7$ are each $C_{1-4}$alkyl, which may be unsubstituted or substituted with 1-3 fluoro, or $R^6$ and $R^7$ are joined together with the atom to which they are attached to form a ring selected from: cyclopentyl, cyclohexyl, cycloheptyl, and tetrahydropyranyl;

$R^{10}$ is selected from the group consisting of:
 (1) hydrogen, and
 (2) methyl;

$R^{12}$ is optionally not present or is halo;

$A^1$ is selected from the group consisting of:
 (1) —CH$_2$—, and
 (2) —N($R^8$)—, wherein $R^8$ is selected from H and $C_{1-6}$alkyl, which is unsubstituted or substituted with 1-3 fluoro;

$E^c$ is —CH═ or —N═; and

-$G^2$-$G^3$-$G^4$- is selected from the group consisting of:
 —CH$_2$—CH$_2$—CH$_2$—,
 —CH$_2$—CH═CH—,
 —CH$_2$—C≡C—,
 —CH$_2$—CH$_2$—S—,
 —CH$_2$—CH$_2$—S(═O)—,
 —CH$_2$—CH$_2$—(C═O)—,
 —CH$_2$—(C═O)—O—, and
 —CH$_2$—CH$_2$—O—;

and pharmaceutically acceptable salts thereof and individual enantiomers and diastereomers thereof.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

The present invention includes compounds of formula I wherein one or more hydrogen atoms are replaced by deuterium.

Tautomers of compounds defined in Formula I are also included within the scope of the present invention. For example, compounds including carbonyl —CH$_2$C(═O)— groups (keto forms) may undergo tautomerism to form hydroxyl —CH═C(OH)— groups (enol forms). Both keto and enol forms are included within the scope of the present invention.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

As will be appreciated by those of skill in the art, not all of the $R^6$ and $R^7$ substituents are capable of forming a ring structure. Moreover, even those substituents capable of ring formation may or may not form a ring structure.

Also as appreciated by those of skill in the art, halo or halogen as used herein are intended to include chloro, fluoro, bromo and iodo.

As used herein, "alkyl" is intended to mean linear, branched and cyclic structures having no carbon-to-carbon double or triple bonds. Thus $C_{1-6}$alkyl is defined to identify the group as having 1, 2, 3, 4, 5 or 6 carbons in a linear or branched arrangement, such that $C_{1-6}$alkyl specifically includes, but is not limited to, methyl, ethyl, n-propyl, iso-propyl, n-butyl, iso-butyl, tert-butyl, pentyl and hexyl. "Cycloalkyl" is an alkyl, part or all of which forms a ring of three or more atoms. $C_0$ or $C_0$alkyl is defined to identify the presence of a direct covalent bond.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof, of the indicated number of carbon atoms, having at least one carbon-to-carbon triple bond. Thus $C_{2-6}$ alkynyl is defined to identify the group as having 2, 3, 4, 5 or 6 carbons in a linear or branched arrangement, such that $C_{2-6}$ alkynyl specifically includes 2-hexynyl and 2-pentynyl.

As used herein, "aryl" is intended to mean any stable monocyclic or bicyclic carbon ring of up to 7 members in each ring, wherein at least one ring is aromatic. Examples of such aryl elements include phenyl, napthyl, tetrahydronapthyl, indanyl, or biphenyl.

The term "heterocycle" or "heterocyclic", as used herein except where noted, represents a stable 4- to 8-membered monocyclic- or stable 8- to 12-membered bicyclic heterocyclic ring system which is either saturated or unsaturated, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic groups include, but are not limited to, azetidine, chroman, dihydrofuran, dihydropyran, dioxane, dioxolane, hexahydroazepine, imidazolidine, imidazolidinone, imidazoline, imidazolinone, indoline, isochroman, isoindoline, isothiazoline, isothiazolidine, isoxazoline, isoxazolidine, morpholine, morpholinone, oxazoline, oxazolidine, oxazolidinone, oxetane, 2-oxohexahydroazepin, 2-oxopiperazine, 2-oxopiperidine, 2-oxopyrrolidine, piperazine, piperidine, pyran, pyrazolidine, pyrazoline, pyrrolidine, pyrroline, quinuclidine, tetrahydrofuran, tetrahydropyran, thiamorpholine, thiazoline, thiazolidine, thiomorpholine and N-oxides thereof.

The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to six heteroatoms selected from the group consisting of N, O, S, P and Si, and wherein the nitrogen, sulfur and phosphorus heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heteroaryl groups include, but are not limited to, benzimidazole, benzisothiazole, benzisoxazole, benzofuran, benzothiazole, benzothiophene, benzotriazole, benzoxazole, carboline, cinnoline, furan, furazan, imidazole, indazole, indole, indolizine, isoquinoline, isothiazole, isoxazole, naphthyridine, oxadiazole, oxazole, phthalazine, pteridine, purine, pyran, pyrazine, pyrazole, pyridazine, pyridine, pyrimidine, pyrrole, quinazoline, quinoline, quinoxaline, tetrazole, thiadiazole, thiazole, thiophene, triazine, triazole, and N-oxides thereof.

The term "alkoxy," as in $C_1$-$C_6$alkoxy, is intended to refer to include alkoxy groups of from 1 to 6 carbon atoms of a straight, branched and cyclic configuration. Examples include methoxy, ethoxy, propoxy, isopropoxy, cyclopropyloxy, cyclohexyloxy and the like.

The variables set forth in the generic descriptions that appear multiple times are independently selected from the indicated groups. For example, $A^1$ and $A^5$ both include —$S(O)_v$— in their definitions and v is defined as 0, 1 or 2. Thus, $A^1$ can be —$S(O)_1$— and $A^5$ can be —$S(O)_2$—. The variable v is not required to be the same in both instances.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which is selected from the group consisting of the compounds disclosed in the following Examples and pharmaceutically acceptable salts thereof and individual diastereomers thereof.

The subject compounds are useful in a method of antagonism of CGRP receptors in a patient such as a mammal in need of such antagonism comprising the administration of an effective amount of the compound. The present invention is directed to the use of the compounds disclosed herein as antagonists of CGRP receptors. In addition to primates, especially humans, a variety of other mammals can be treated according to the method of the present invention.

Another embodiment of the present invention is directed to a method for the treatment, control, amelioration, or reduction of risk of a disease or disorder in which the CGRP receptor is involved in a patient that comprises administering to the patient a therapeutically effective amount of a compound that is an antagonist of CGRP receptors.

The present invention is further directed to a method for the manufacture of a medicament for antagonism of CGRP receptors activity in humans and animals comprising combining a compound of the present invention with a pharmaceutical carrier or diluent.

The subject treated in the present methods is generally a mammal, for example a human being, male or female, in whom antagonism of CGRP receptor activity is desired. The term "therapeutically effective amount" means the amount of the subject compound that will elicit the biological or medical response of a tissue, system, animal or human that is being sought by the researcher, veterinarian, medical doctor or other clinician. As used herein, the term "treatment" refers both to the treatment and to the prevention or prophylactic therapy of the mentioned conditions, particularly in a patient who is predisposed to such disease or disorder.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The utility of the compounds in accordance with the present invention as antagonists of CGRP receptor activity may be demonstrated by methodology known in the art. Inhibition of the binding of $^{125}$I-CGRP to receptors and functional antagonism of CGRP receptors were determined as follows:

NATIVE RECEPTOR BINDING ASSAY: The binding of $^{125}$I-CGRP to receptors in SK-N-MC cell membranes was carried out essentially as described (Edvinsson et al. (2001) *Eur. J. Pharmacol.* 415, 39-44). Briefly, membranes (25 µg) were incubated in 1 mL of binding buffer [10 mM HEPES, pH 7.4, 5 mM MgCl$_2$ and 0.2% bovine serum albumin (BSA)] containing 10 µM $^{125}$I-CGRP and antagonist. After incubation at room temperature for 3 h, the assay was terminated by filtration through GFB glass fibre filter plates (PerkinElmer) that had been blocked with 0.5% polyethyleneimine for 3 h. The filters were washed three times with ice-cold assay buffer (10 mM HEPES, pH 7.4 and 5 mM MgCl$_2$), then the plates were air dried. Scintillation fluid (50 µL) was added and the radioactivity was counted on a Topcount (Packard Instrument). Data analysis was carried out by using Prism and the K$_i$ was determined by using the Cheng-Prusoff equation (Cheng & Prusoff (1973) *Biochem. Pharmacol.* 22, 3099-3108).

RECOMBINANT RECEPTOR: Human CL receptor (Genbank accession number L76380) was subcloned into the expression vector pIREShyg2 (BD Biosciences Clontech) as a 5'NheI and 3' PmeI fragment. Human RAMP1 (Genbank accession number AJ001014) was subcloned into the expression vector pIRESpuro2 (BD Biosciences Clontech) as a 5'NheI and 3'NotI fragment. HEK 293 cells (human embryonic kidney cells; ATCC #CRL-1573) were cultured in DMEM with 4.5 g/L glucose, 1 mM sodium pyruvate and 2 mM glutamine supplemented with 10% fetal bovine serum (FBS), 100 units/mL penicillin and 100 µg/mL streptomycin, and maintained at 37° C. and 95% humidity. Cells were subcultured by treatment with 0.25% trypsin with 0.1% EDTA in HBSS. Stable cell line generation was accomplished by co-transfecting 10 µg of DNA with 30 µg Lipofectamine 2000 (Invitrogen) in 75 cm$^2$ flasks. CL receptor and RAMP1 expression constructs were co-transfected in equal amounts. Twenty-four hours after transfection the cells were diluted and selective medium (growth medium+300 µg/mL hygromycin and 1 µg/mL puromycin) was added the following day. A clonal cell line was generated by single cell deposition utilizing a FACS Vantage SE (Becton Dickinson). Growth medium was adjusted to 150 µg/mL hygromycin and 0.5 µg/mL puromycin for cell propagation.

RECOMBINANT RECEPTOR BINDING ASSAY: Cells expressing recombinant human CL receptor/RAMP1 were washed with PBS and harvested in harvest buffer containing 50 mM HEPES, 1 mM EDTA and Complete protease inhibitors (Roche). The cell suspension was disrupted with a laboratory homogenizer and centrifuged at 48,000 g to isolate membranes. The pellets were resuspended in harvest buffer plus 250 mM sucrose and stored at −70° C. For binding assays, 20 µg of membranes were incubated in 1 ml binding buffer (10 mM HEPES, pH 7.4, 5 mM MgCl$_2$, and 0.2% BSA) for 3 hours at room temperature containing 10 µM $^{125}$I-hCGRP (GE Healthcare) and antagonist. The assay was terminated by filtration through 96-well GFB glass fiber filter plates (PerkinElmer) that had been blocked with 0.05% polyethyleneimine. The filters were washed 3 times with ice-cold assay buffer (10 mM HEPES, pH 7.4 and 5 mM MgCl$_2$). Scintillation fluid was added and the plates were counted on a Topcount (Packard). Non-specific binding was determined and the data analysis was carried out with the apparent dissociation constant (K$_i$) determined by using a non-linear least squares fitting the bound CPM data to the equation below:

$$Y_{obsd} = \frac{(Y_{max} - Y_{min})(\% \, I_{max} - \% \, I_{min}/100) + Y_{min} + (Y_{max} - Y_{min})(100 - \% \, I_{max}/100)}{1 + ([Drug]/K_i(1 + [Radiolabel]/K_d)nH}$$

Where Y is observed CPM bound, Y$_{max}$ is total bound counts, Y$_{min}$ is non specific bound counts, (Y$_{max}$−Y$_{min}$) is specific bound counts, % I$_{max}$ is the maximum percent inhibition, % I min is the minimum percent inhibition, radiolabel is the probe, and the K$_d$ is the apparent dissociation constant for the radioligand for the receptor as determined by Hot saturation experiments.

RECOMBINANT RECEPTOR FUNCTIONAL ASSAY: Cells were plated in complete growth medium at 85,000 cells/well in 96-well poly-D-lysine coated plates (Corning) and cultured for ~19 h before assay. Cells were washed with PBS and then incubated with inhibitor for 30 min at 37° C. and 95% humidity in Cellgro Complete Serum-Free/Low-Protein medium (Mediatech, Inc.) with L-glutamine and 1 g/L BSA. Isobutyl-methylxanthine was added to the cells at a concentration of 300 µM and incubated for 30 min at 37° C. Human α-CGRP was added to the cells at a concentration of 0.3 nM and allowed to incubate at 37° C. for 5 min. After α-CGRP stimulation the cells were washed with PBS and processed for cAMP determination utilizing the two-stage assay procedure according to the manufacturer's recommended protocol (cAMP SPA direct screening assay system; RPA 559; GE Healthcare). Dose response curves were plotted and IC$_{50}$ values determined from a 4-parameter logistic fit as defined by the equation $y=((a-d)/(1+(x/c)^b)+d$, where y=response, x=dose, a=max response, d=min response, c=inflection point and b=slope.

Examples 1 to 6, 8, 9, 13, 15, and 18 to 55 were tested and had activity in the aforementioned RECOMBINANT RECEPTOR BINDING ASSAY, generally with a $K_i$ value of less than about 50 µM.

The ability of the compounds of the present invention to act as CGRP antagonists makes them useful pharmacological agents for disorders that involve CGRP in humans and animals, but particularly in humans.

The compounds of the present invention have utility in treating, preventing, ameliorating, controlling or reducing the risk of one or more of the following conditions or diseases: headache; migraine; cluster headache; chronic tension type headache; pain; chronic pain; neurogenic inflammation and inflammatory pain; neuropathic pain; eye pain; tooth pain; diabetes; non-insulin dependent diabetes mellitus; vascular disorders; inflammation; arthritis; bronchial hyperreactivity, asthma; shock; sepsis; opiate withdrawal syndrome; morphine tolerance; hot flashes in men and women; allergic dermatitis; psoriasis; encephalitis; brain trauma; epilepsy; neurodegenerative diseases; skin diseases; neurogenic cutaneous redness, skin rosaceousness and erythema; inflammatory bowel disease, irritable bowel syndrome, cystitis; and other conditions that may be treated or prevented by antagonism of CGRP receptors. Of particular importance is the acute or prophylactic treatment of headache, including migraine and cluster headache.

The subject compounds are further useful in a method for the prevention, treatment, control, amelioration, or reduction of risk of the diseases, disorders and conditions noted herein.

The subject compounds are further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with an anti-migraine agent, such as ergotamine and dihydroergotamine, or other serotonin agonists, especially a 5-HT$_{1B/1D}$ agonist, for example sumatriptan, naratriptan, zolmitriptan, eletriptan, almotriptan, frovatriptan, donitriptan, and rizatriptan, a 5-HT$_{1D}$ agonist such as PNU-142633 and a 5-HT$_{1F}$ agonist such as LY334370; a cyclooxygenase inhibitor, such as a selective cyclooxygenase-2 inhibitor, for example rofecoxib, etoricoxib, celecoxib, valdecoxib or paracoxib; a non-steroidal anti-inflammatory agent or a cytokine-suppressing anti-inflammatory agent, for example with a compound such as ibuprofen, ketoprofen, fenoprofen, naproxen, indomethacin, sulindac, meloxicam, piroxicam, tenoxicam, lornoxicam, ketorolac, etodolac, mefenamic acid, meclofenamic acid, flufenamic acid, tolfenamic acid, diclofenac, oxaprozin, apazone, nimesulide, nabumetone, tenidap, etanercept, tolmetin, phenylbutazone, oxyphenbutazone, diflunisal, salsalate, olsalazine or sulfasalazine and the like; or glucocorticoids. Similarly, the instant compounds may be administered with an analgesic such as aspirin, acetaminophen, phenacetin, fentanyl, sufentanil, methadone, acetyl methadol, buprenorphine or morphine.

Additionally, the present compounds may be used in conjunction with an interleukin inhibitor, such as an interleukin-1 inhibitor; an NK-1 receptor antagonist, for example aprepitant and fosaprepitant; an NMDA antagonist; an NR2B antagonist; a bradykinin-1 receptor antagonist; an adenosine A1 receptor agonist; a sodium channel blocker, for example lamotrigine; an opiate agonist such as levomethadyl acetate or methadyl acetate; a lipoxygenase inhibitor, such as an inhibitor of 5-lipoxygenase; an alpha receptor antagonist, for example indoramin; an alpha receptor agonist; a vanilloid receptor antagonist; a renin inhibitor; a granzyme B inhibitor; an endothelin antagonist; a norepinephrin precursor; anti-anxiety agents such as diazepam, alprazolam, chlordiazepoxide and chlorazepate; serotonin 5HT$_2$ receptor antagonists; opiod agonists such as codeine, hydrocodone, tramadol, dextropropoxyphene and febtanyl; an mGluR5 agonist, antagonist or potentiator; a GABA A receptor modulator, for example acamprosate calcium; nicotinic antagonists or agonists including nicotine; muscarinic agonists or antagonists; a selective serotonin reuptake inhibitor, for example fluoxetine, paroxetine, sertraline, duloxetine, escitalopram, or citalopram; an antidepressant, for example amitriptyline, nortriptyline, clomipramine, imipramine, venlafaxine, doxepin, protriptyline, desipramine, trimipramine, or imipramine; a leukotriene antagonist, for example montelukast or zafirlukast; an inhibitor of nitric oxide or an inhibitor of the synthesis of nitric oxide.

Also, the present compounds may be used in conjunction with gap junction inhibitors; neuronal calcium channel blockers such as civamide; AMPA/KA antagonists such as LY293558; sigma receptor agonists; and vitamin B2.

Also, the present compounds may be used in conjunction with ergot alkaloids other than ergotamine and dihydroergotamine, for example ergonovine, ergonovine, methylergonovine, metergoline, ergoloid mesylates, dihydroergocornine, dihydroergocristine, dihydroergocryptine, dihydro-α-ergocryptine, dihydro-β-ergocryptine, ergotoxine, ergocornine, ergocristine, ergocryptine, α-ergocryptine, β-ergocryptine, ergosine, ergostane, bromocriptine, or methysergide.

Additionally, the present compounds may be used in conjunction with a beta-adrenergic antagonist such as timolol, propanolol, atenolol, metoprolol or nadolol, and the like; a MAO inhibitor, for example phenelzine; a calcium channel blocker, for example flunarizine, diltiazem, amlodipine, felodipine, nisolipine, isradipine, nimodipine, lomerizine, verapamil, nifedipine, or prochlorperazine; neuroleptics such as olanzapine, droperidol, prochlorperazine, chlorpromazine and quetiapine; an anticonvulsant such as topiramate, zonisamide, tonabersat, carabersat, levetiracetam, lamotrigine, tiagabine, gabapentin, pregabalin or divalproex sodium; an anti-hypertensive such as an angiotensin II antagonist, for example losartan, irbesartin, valsartan, eprosartan, telmisartan, olmesartan, medoxomil, candesartan and candesartan cilexetil, an angiotensin I antagonist, an angiotensin converting enzyme inhibitor such as lisinopril, enalapril, captopril, benazepril, quinapril, perindopril, ramipril and trandolapril; or botulinum toxin type A or B.

The present compounds may be used in conjunction with a potentiator such as caffeine, an H2-antagonist, simethicone, aluminum or magnesium hydroxide; a decongestant such as oxymetazoline, epinephrine, naphazoline, xylometazoline, propylhexedrine, or levo-desoxy-ephedrine; an antitussive such as caramiphen, carbetapentane, or dextromethorphan; a diuretic; a prokinetic agent such as metoclopramide or domperidone; a sedating or non-sedating antihistamine such as acrivastine, azatadine, bromodiphenhydramine, brompheniramine, carbinoxamine, chlorpheniramine, clemastine, dexbrompheniramine, dexchlorpheniramine, diphenhydramine, doxylamine, loratadine, phenindamine, pheniramine, phenyltoloxamine, promethazine, pyrilamine, terfenadine, triprolidine, phenylephrine, phenylpropanolamine, or pseudoephedrine. The present compounds also may be used in conjunction with anti-emetics.

In a particular embodiment the present compounds are used in conjunction with an anti-migraine agent, such as: ergotamine or dihydroergotamine; a 5-HT$_1$ agonist, especially a 5-HT$_{1B/1D}$ agonist, in particular, sumatriptan, naratriptan, zolmitriptan, eletriptan, almotriptan, frovatriptan, donitriptan, avitriptan and rizatriptan, and other serotonin agonists; and a cyclooxygenase inhibitor, such as a selective cyclooxygenase-2 inhibitor, in particular, rofecoxib, etoricoxib, celecoxib, valdecoxib or paracoxib.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require antagonism of CGRP receptor activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

When treating, preventing, controlling, ameliorating, or reducing the risk of headache, migraine, cluster headache, or other diseases for which compounds of the present invention are indicated, generally satisfactory results are obtained when the compounds of the present invention are administered at a daily dosage of from about 0.1 milligram to about 100 milligram per kilogram of animal body weight, given as a single daily dose or in divided doses two to six times a day, or in sustained release form. For most large mammals, the total daily dosage is from about 1.0 milligrams to about 1000 milligrams, or from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Several methods for preparing the compounds of this invention are illustrated in the following Schemes and Examples. Starting materials are made according to procedures known in the art or as illustrated herein.

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

Heck substrate 2 (Scheme 1). Palladium-catalyzed Heck coupling of 2 with halide intermediate 3 (for example, compounds where X=Br or I) then affords alkene compound 4, where $R^{PG}$ may be hydrogen or other substituents as defined herein.

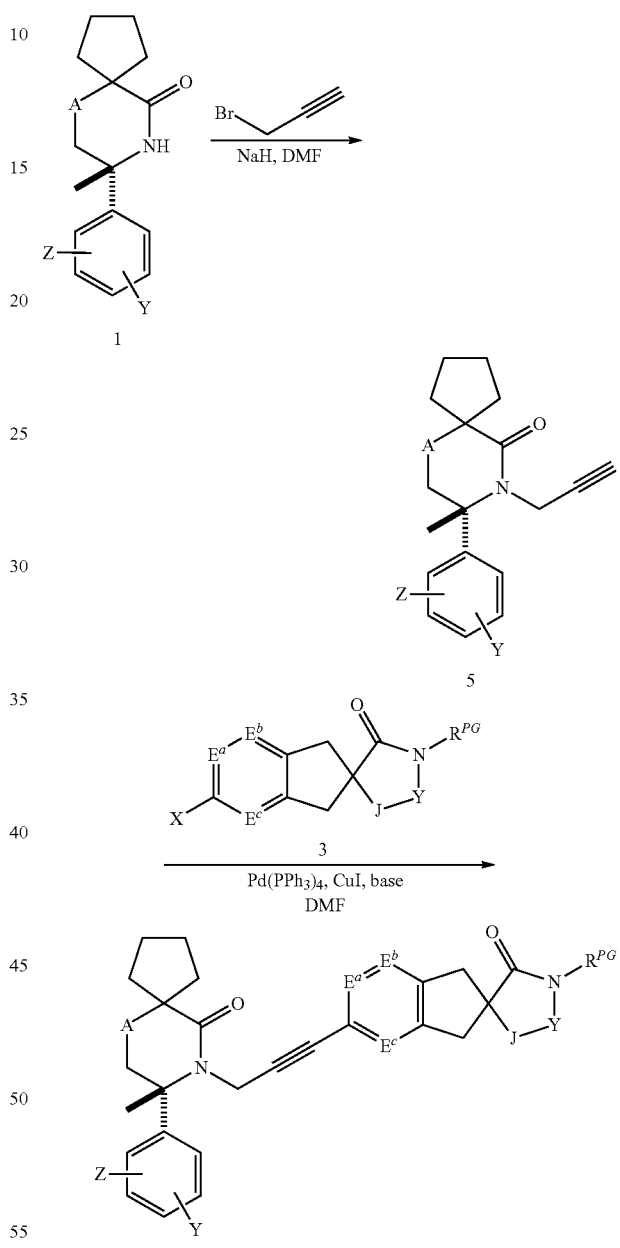

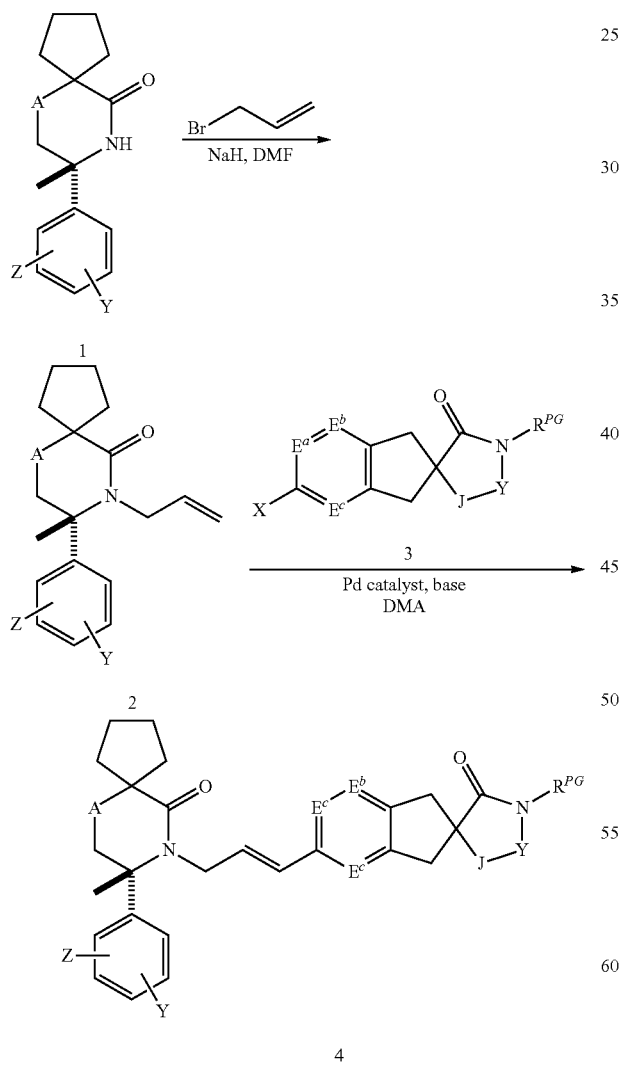

Intermediate 1 (for e.g., compounds described in Wood et al US 20070265225) is alkylated with allyl bromide to yield Similarly, intermediate 1 is alkylated with propargyl bromide to afford alkyne 5, which then undergoes Sonogashira coupling with halide 3 to afford the alkyne derivative 6 (Scheme 2). As shown in Scheme 3, either alkene 4 or alkyne 6 may be further reduced to the alkane analog 7 under standard hydrogenation conditions.

SCHEME 3

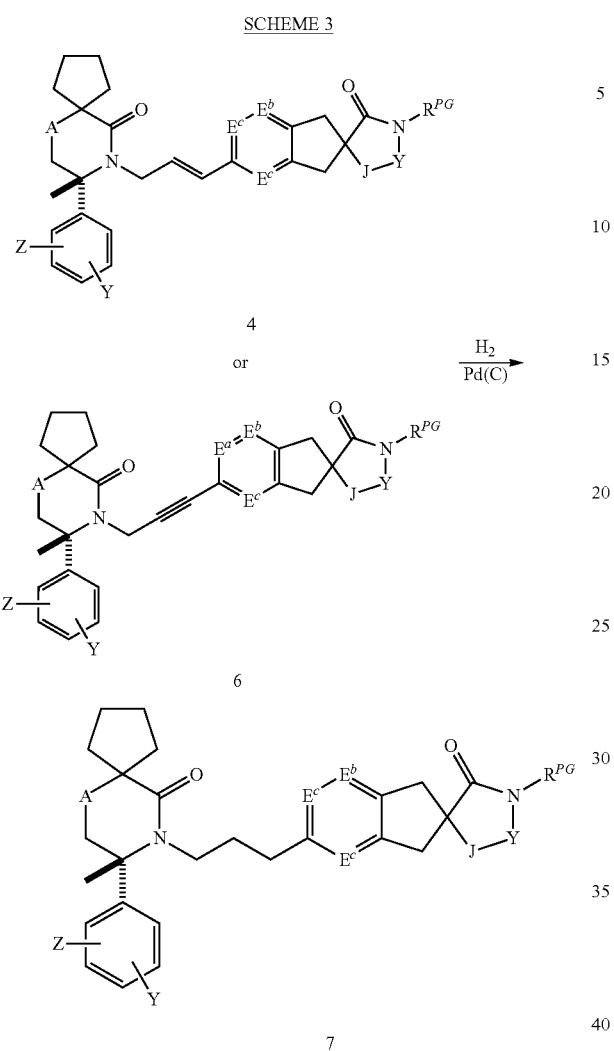

A route to piperazinone-containing Heck substrates such as 12 is illustrated in Scheme 4.

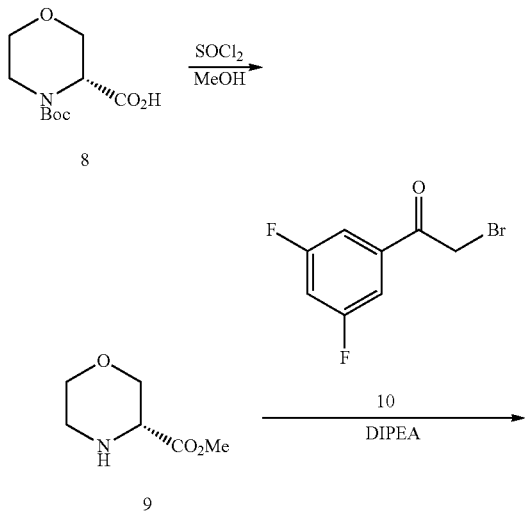

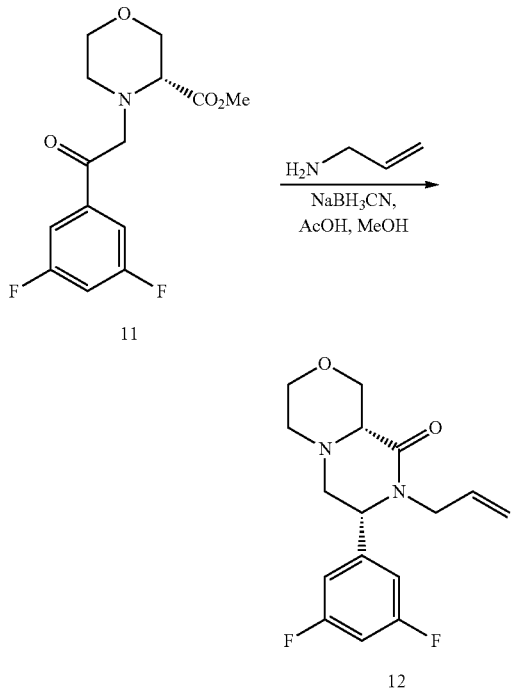

Starting from an amino acid such as 2-carboxymorpholine 8, esterification and alkylation with commercially available bromoacetophenone 10 affords keto-ester 11, which on treatment with allylamine in the presence of sodium cyanoborohydride undergoes a tandem reductive alkylation-cyclization reaction to give allylated piperazinone 12. Other amino acids and bromoacetophenone analogs may be substituted to give rise to additional allyl piperazinone derivatives using similar procedures.

SCHEME 5

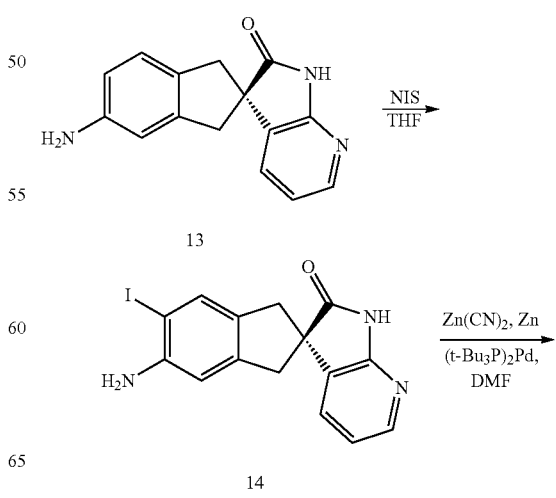

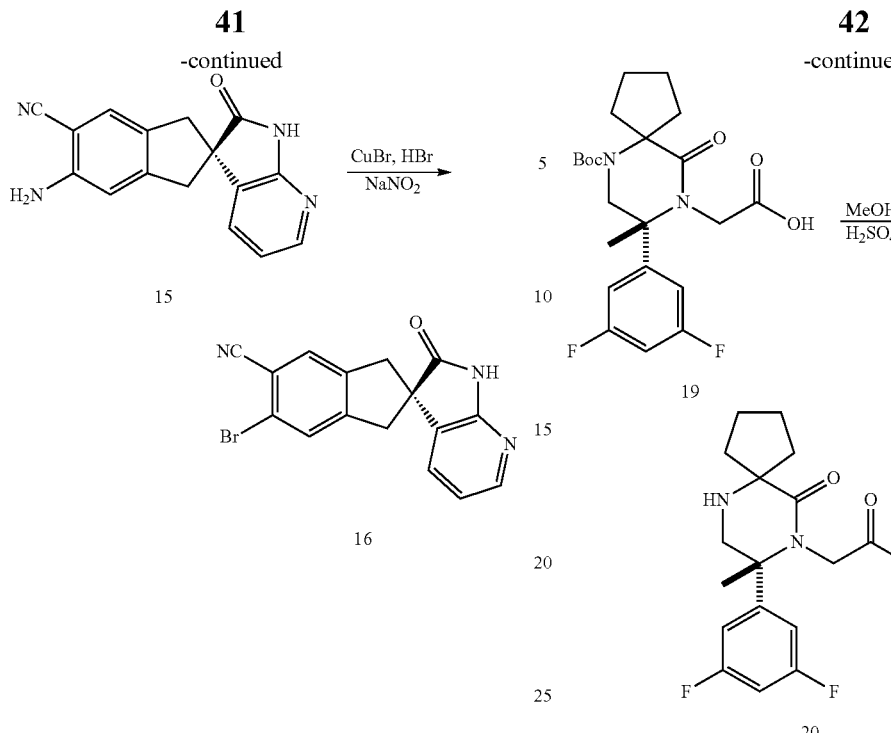

A representative synthesis of a substituted version of halide 3 (i.e., bromocyanophenyl derivative 16) for use in the Heck or Sonogashira coupling reactions described above is depicted in Scheme 5. Aniline 13 is treated with N-iodosuccinimide to give iodide 14, which is then coupled with zinc cyanide to give the cyano aniline 15. Standard Sandmeyer chemistry then affords the requisite cyano bromide 16, for coupling as depicted in Schemes 1 and 2 above.

SCHEME 6

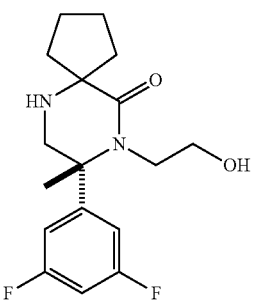

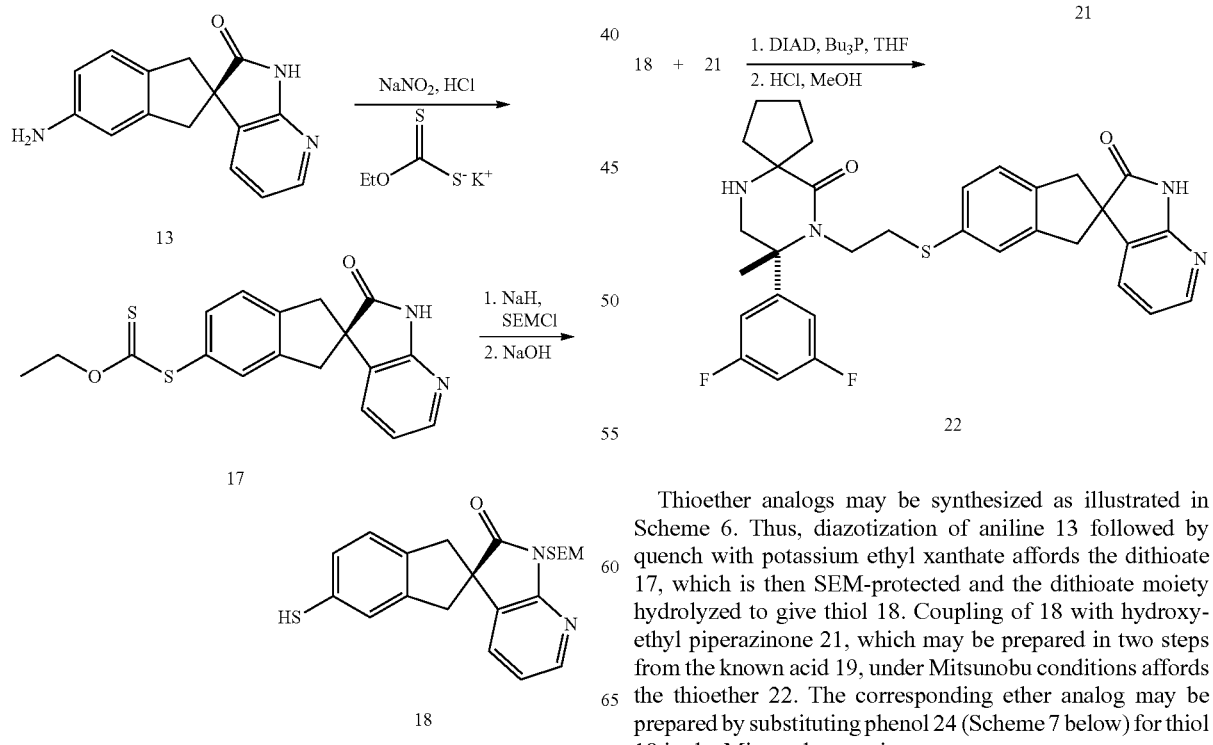

Thioether analogs may be synthesized as illustrated in Scheme 6. Thus, diazotization of aniline 13 followed by quench with potassium ethyl xanthate affords the dithioate 17, which is then SEM-protected and the dithioate moiety hydrolyzed to give thiol 18. Coupling of 18 with hydroxyethyl piperazinone 21, which may be prepared in two steps from the known acid 19, under Mitsunobu conditions affords the thioether 22. The corresponding ether analog may be prepared by substituting phenol 24 (Scheme 7 below) for thiol 18 in the Mitsunobu reaction.

SCHEME 7

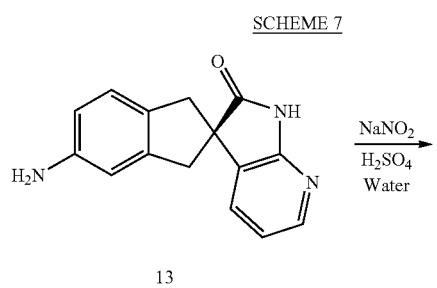

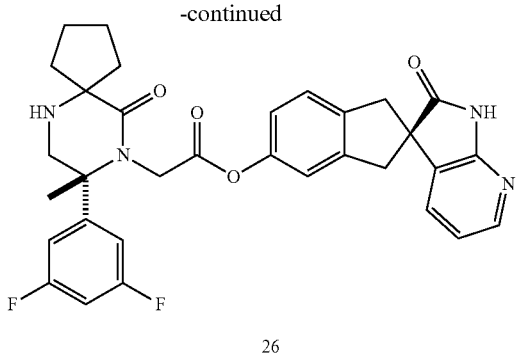

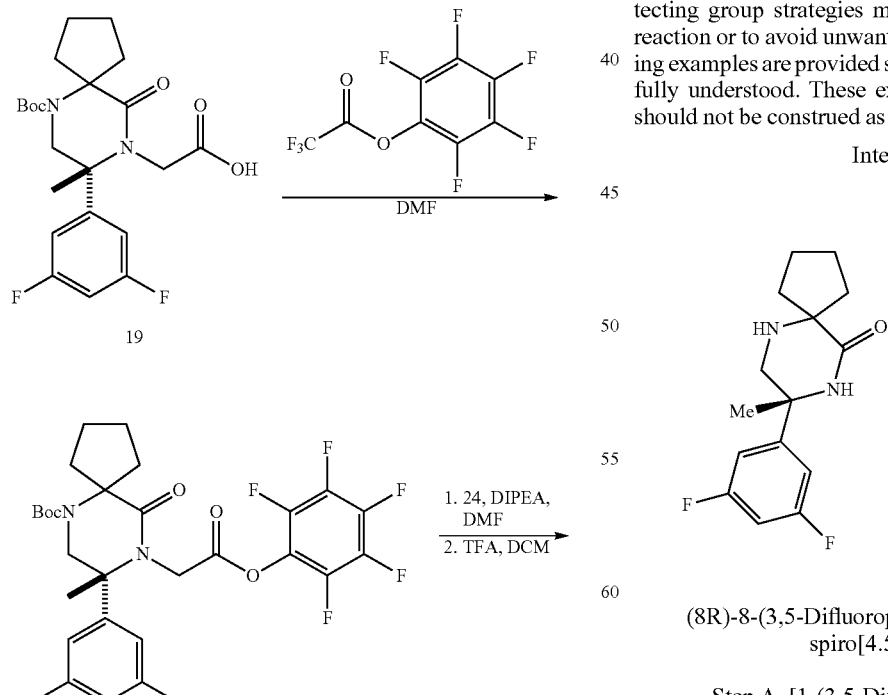

Ester analogs such as compound 26 may be prepared according to Scheme 7. Thus, conversion of aniline 13 to phenol 23 under Sandmeyer conditions followed by SEM-protection affords intermediate 24. Activation of acid 19 as the pentafluorophenyl ester followed by coupling to 24 and deprotection affords the ester 26.

It is understood that alternative methodologies may also be employed in the synthesis of these key intermediates. For instance, racemic reaction sequences may be utilized, followed by chiral separations at appropriate steps to provide compounds of the present invention. The exact choice of reagents, solvents, temperatures, and other reaction conditions, depends upon the nature of the intended product. In some cases, appropriate protecting group strategies may be used.

In some cases the final product may be further modified, for example, by manipulation of substituents. These manipulations may include, but are not limited to, reduction, oxidation, alkylation, acylation, and hydrolysis reactions which are commonly known to those skilled in the art.

In some cases the order of carrying out the foregoing reaction schemes may be varied to facilitate the reaction or to avoid unwanted reaction products. Additionally, various protecting group strategies may be employed to facilitate the reaction or to avoid unwanted reaction products. The following examples are provided so that the invention might be more fully understood. These examples are illustrative only and should not be construed as limiting the invention in any way.

Intermediate 1

(8R)-8-(3,5-Difluorophenyl)-8-methyl-6,9-diaza-spiro[4.5]decan-10-one

Step A. [1-(3,5-Difluorophenyl)ethyl]amine

To a stirred mixture of 3',5'-difluoroacetophenone (86.8 g, 0.556 mol) and 2 M NH₃ in EtOH (1.4 L, 2.8 mol) was added titanium(IV) isopropoxide (326 mL, 1.11 mol) dropwise over 15 min stirring was continued at ambient temperature for 20 h. The mixture was cooled in an ice-water bath and sodium borohydride (31.5 g, 0.834 mol) was added in portions over 60 min. The reaction mixture was stirred for an additional 1 h, and then quenched with aqueous $NH_4OH$ (2 M, 1.3 L) followed by EtOAc (1 L). The resulting mixture was aged for 18 h and filtered through a pad of celite, washing with EtOAc (1 L). To the filtrate was added EtOAc (2 L) and $H_2O$ (1 L) containing NaCl (ca. 100 g). The mixture was shaken and allowed to separate. The organic layer was concentrated in vacuo to a volume of about 500 mL and partitioned between EtOAc (2 L) and saturated aqueous $Na_2CO_3$ (300 mL). The organic layer was dried ($Na_2SO_4$), filtered, and concentrated in vacuo to give the title compound. MS: m/z=182 (M+$CH_3CN$−$NH_2$).

Step B. Di-tert-butyl[1-(3,5-difluorophenyl)ethyl]imidodicarbonate

To a solution of [1-(3,5-difluorophenyl)ethyl]amine (76 g, 481 mmol) in $CH_2Cl_2$ (1 L) at 0° C. was added di-tert-butyl dicarbonate (134 mL, 577 mmol) and the resulting mixture was stirred at ambient temperature for 2 h. The solvent was removed under reduced pressure. To the residue was added di-tert-butyl dicarbonate (336 mL, 1.44 mol) and DMAP (58.8 g, 481 mmol) and the reaction mixture was heated at 60° C. for 18 h. The resulting mixture was heated at 70° C. and additional di-tert-butyl dicarbonate (896 mL, 3.85 mol) was added dropwise, intermittently, over a period of 4 days. The reaction mixture was allowed to cool, and was concentrated in vacuo. The crude product was purified by silica gel chromatography, eluting with a gradient of hexane:EtOAc—100:0 to 85:15, to give the title compound. MS: m/z=421 (M+Na+$CH_3CN$).

Step C. tert-Butyl 2-[(tert-butoxycarbonyl)amino]-2-(3,5-difluorophenyl)propanoate To a stirred suspension of potassium tert-butoxide (64 g, 570 mmol) in THF (800 mL) at −78° C. was added a solution of di-tert-butyl[1-(3,5-difluorophenyl)ethyl]imidodicarbonate (68 g, 190 mmol) in THF (480 mL), dropwise, over 45 min. The reaction mixture was allowed to warm to ambient temperature and stirring was continued for 1 h. The reaction mixture was cooled to −78° C. and quenched with 1 N aqueous HCl (600 mL), warmed to 0° C., and poured into $Et_2O$ (750 mL). The organic layer was extracted and the aqueous layer was extracted further with $Et_2O$ (750 mL). The combined organic extracts were dried over $Na_2SO_4$, filtered, and concentrated in vacuo. The crude product was purified by silica gel chromatography, eluting with hexane:EtOAc—100:0 to 80:20, to give the title compound. MS: m/z=295 (M+1).

Step D. tert-Butyl[1-(3,5-difluorophenyl)-1-methyl-2-oxoethyl]carbamate

To a stirred solution of tert-butyl 2-[(tert-butoxycarbonyl)amino]-2-(3,5-difluorophenyl)propanoate (27.0 g, 76 mmol) in THF (350 mL) at −78° C. was added $LiAlH_4$ (76 mL of a 1 M solution in THF, 76 mmol), dropwise. The reaction mixture was stirred at −78° C. for 3 h, then quenched with EtOAc (76 mL), then $H_2O$ (228 mL), then 1 N aqueous NaOH (76 mL), then EtOAc (228 mL). The reaction mixture was warmed to ambient temperature, stirred for 1 h, filtered, and extracted with EtOAc (2×450 mL). The organic extracts were dried over $Na_2SO_4$, filtered, and concentrated in vacuo. The crude product was purified by silica gel chromatography, eluting with hexane:EtOAc—100:0 to 70:30, to give the title compound. MS: m/z=186 (M−$CO_2C_4H_7$).

Step E. Methyl 1-aminocyclopentanecarboxylate hydrochloride

A solution of 1-aminocyclopentanecarboxylic acid (20.0 g, 155 mmol) in MeOH (300 mL) was saturated with HCl (g), aged for 30 min, and saturated again with HCl (g). The mixture was aged at ambient temperature for 2 h and concentrated to dryness in vacuo. To the white solid was added saturated aqueous $NaHCO_3$ (350 mL), carefully, with ice cooling, and the resulting mixture was extracted with EtOAc (4×250 mL). The combined organic extracts were dried over $Na_2SO_4$, filtered, and concentrated in vacuo to give the title compound. MS: m/z=144 (M+1).

Step F. Methyl 1-{[2-[(tert-butoxycarbonyl)amino]-2-(3,5-difluorophenyl)propyl]amino}cyclopentanecarboxylate To tert-butyl[1-(3,5-difluorophenyl)-1-methyl-2-oxoethyl]carbamate (28.9 g, 101 mmol) were added methyl 1-aminocyclopentanecarboxylate (43.4 g, 303 mmol) followed by titanium(IV) isopropoxide (44.5 mL, 152 mmol) and the reaction mixture was stirred at ambient temperature for 90 min, diluted with MeOH (130 mL), and cooled in an ice-water bath. To this stirred mixture were added AcOH (29 mL, 507 mmol) followed by $NaCNBH_3$ (7.64 g, 122 mmol), portionwise, over 5 min. Stirring was continued for 5 min, then the ice-water bath was removed, and stirring was continued for 30 min. The reaction mixture was quenched with saturated aqueous $NaHCO_3$ (1 L) and extracted with EtOAc (3×1.5 L). The combined organic extracts were washed with brine, dried over $Na_2SO_4$, filtered, and concentrated in vacuo. The crude product was purified by silica gel chromatography, eluting with hexane:EtOAc—100:0 to 50:50, to give a mixture of the title compound and the corresponding isopropyl ester. MS: m/z=413 (M+1).

Step G. (8R)-8-(3,5-Difluorophenyl)-8-methyl-6,9-diazaspiro[4.5]decan-10-one

To a solution of methyl 1-{[2-amino-2-(3,5-difluorophenyl)propyl]amino}cyclopentanecarboxylate and the corresponding isopropyl ester (20.1 g, 48.7 mmol) in n-BuOH (1 L) was added c. $H_2SO_4$ (29 mL, 544 mmol) and the reaction mixture was heated at reflux for 40 h. The cooled mixture was concentrated under reduced pressure to a volume of about 500 mL and then poured into ice-cooled saturated aqueous $NaHCO_3$ (1 L). The resulting mixture was extracted with EtOAc (2×1 L). The combined organic extracts were dried over $Na_2SO_4$, filtered, and concentrated under reduced pressure. The crude product was filtered to remove the white precipitate and purified by silica gel chromatography, eluting with a gradient of $CHCl_3$:MeOH:$NH_4OH$—100:0:0 to 90:10:0.5, to give some pure fractions of racemic product and some that were contaminated with n-butyl 1-{[2-amino-2-(3,5-difluorophenyl)propyl]amino}cyclopentanecarboxylate. The product from the mixed fractions was recrystallized from EtOAc/$Et_2O$ to give additional racemic product. The enantiomers were separated by SFC, using a Chiralcel OD-H column and eluting with $CO_2$:MeOH—85:15. The first major peak to elute was (8S)-8-(3,5-difluorophenyl)-8-methyl-6,9-diazaspiro[4.5]decan-10-one and the second major peak to elute was (8R)-8-(3,5-difluorophenyl)-8-methyl-6,9-diazaspiro[4.5]decan-10-one, the title compound. MS: m/z=281 (M+1).

Intermediate 2

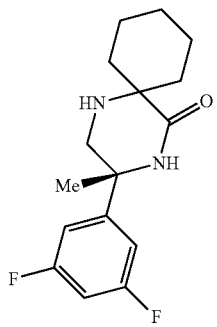 [SMILES: C[C@@]1(c2cc(F)cc(F)c2)CNC2(CCCCC2)C(=O)N1]

(3R)-3-(3,5-Difluorophenyl)-3-methyl-1,4-diazaspiro[5.5]undecan-5-one

Step A. Di-tert-butyl[1-(3,5-difluorophenyl)ethyl]imidodicarbonate

To a solution of [1-(3,5-difluorophenyl)ethyl]amine (10.0 g, 63.6 mmol, described in Intermediate 1) in $CH_2Cl_2$ (200 mL) at 0° C. was added di-tert-butyl dicarbonate (13.9 g, 63.6 mmol) and the resulting mixture was stirred at ambient temperature for 18 h. The solvent was removed under reduced pressure. To the residue was added di-tert-butyl dicarbonate (20.8 g, 95.4 mmol) and DMAP (7.78 g, 63.6 mmol) and the reaction mixture was heated at 80° C. for 2 h. The mixture was allowed to cool and additional di-tert-butyl dicarbonate (69.4 g, 318 mmol) was added. The reaction mixture was heated at 80° C. for 2 h, allowed to cool, and concentrated in vacuo. The crude product was purified by silica gel chromatography, eluting with a gradient of hexane:EtOAc—98:2 to 90:10, to give the title compound. MS: m/z=421 (M+Na+$CH_3CN$).

Step B. tert-Butyl 2-[(tert-butoxycarbonyl)amino]-2-(3,5-difluorophenyl)propanoate To a stirred suspension of potassium tert-butoxide in THF (300 mL) at −78° C. was added a solution of di-tert-butyl[1-(3,5-difluorophenyl)ethyl]imidodicarbonate from Step A (22.0 g, 61.6 mmol) in THF (200 mL), dropwise, over 45 min. The reaction mixture was allowed to warm to ambient temperature and stirring was continued for 3 h. The reaction mixture was cooled to −78° C. and quenched with 1 N aqueous HCl (300 mL), warmed to 0° C., and poured into $Et_2O$ (300 mL). The organic layer was extracted and the aqueous layer was extracted further with $Et_2O$ (300 mL). The combined organic extracts were dried over $Na_2SO_4$, filtered, and concentrated in vacuo. The crude product was purified by silica gel chromatography, eluting with hexane:EtOAc—95:5 to 80:20, to give the title compound. MS: m/z=421 (M+Na+$CH_3CN$).

Step C. tert-Butyl[1-(3,5-difluorophenyl)-1-methyl-2-oxoethyl]carbamate

To a stirred solution of tert-butyl 2-[(tert-butoxycarbonyl)amino]-2-(3,5-difluorophenyl)propanoate from Step B (2.00 g, 5.60 mmol) in THF (20 mL) at −78° C. was added $LiAlH_4$ (5.60 mL of a 1 M solution in THF, 5.60 mmol), dropwise. The reaction mixture was stirred at −78° C. for 6 h, then quenched with EtOAc (5.6 mL), then $H_2O$ (15.6 mL), then 1 N aqueous NaOH (5.6 mL), then EtOAc (17 mL). The reaction mixture was warmed to ambient temperature, stirred for 1 h, filtered, and extracted with EtOAc (2×40 mL). The organic extracts were dried over $Na_2SO_4$, filtered, and concentrated in vacuo to afford the title compound in sufficient purity for use in the next step. MS: m/z=186 (M−$CO_2C_4H_7$).

Step D. Methyl 1-aminocyclohexanecarboxylate hydrochloride

Essentially following the procedures described in Intermediate 1 for methyl 1-aminocyclopentanecarboxylate hydrochloride, but using 1-aminocyclohexanecarboxylic acid in place of 1-aminocyclopentanecarboxylic acid, the title compound was obtained. MS: m/z=158 (M+1).

Step E. Methyl 1-{[2-[(tert-butoxycarbonyl)amino]-2-(3,5-difluorophenyl)propyl]amino}cyclohexanecarboxylate A mixture of tert-butyl[1-(3,5-difluorophenyl)-1-methyl-2-oxoethyl]carbamate from Step C (500 mg, 1.75 mmol), methyl 1-aminocyclohexanecarboxylate hydrochloride from Step D (1.38 g, 8.76 mmol), and AcOH (0.301 mL, 5.26 mmol) in MeOH (15 mL) was stirred at ambient temperature for 30 min. $NaCNBH_3$ (165 mg, 2.63 mmol) was added and the pH of the mixture was checked and adjusted to pH ~5 as necessary by addition of AcOH. The reaction mixture was stirred at ambient temperature for 1 h, then quenched with saturated aqueous $NaHCO_3$ (10 mL) and extracted with $CH_2Cl_2$ (2×50 mL). The combined organic extracts were dried over $Na_2SO_4$, filtered, and concentrated in vacuo. The crude product was purified by silica gel chromatography, eluting with hexane:EtOAc—100:0 to 80:20, to give the title compound. MS: m/z=427 (M+1).

Step F. Methyl 1-{[2-amino-2-(3,5-difluorophenyl)propyl]amino}cyclohexanecarboxylate A solution of methyl 1-{[2-[(tert-butoxycarbonyl)amino]-2-(3,5-difluorophenyl)propyl]amino}cyclohexanecarboxylate from Step E (280 mg, 0.657 mmol) in EtOAc (5 mL) at 0° C. was saturated with HCl (g). The reaction mixture was aged at 0° C. for 30 min, then poured carefully into saturated aqueous $NaHCO_3$ (10 mL). The resulting mixture was extracted with EtOAc (2×15 mL). The combined organic extracts were dried over $Na_2SO_4$, filtered, and concentrated in vacuo to give the title compound. MS: m/z=327 (M+1).

Step G. (3R)-3-(3,5-Difluorophenyl)-3-methyl-1,4-diazaspiro[5.5]undecan-5-one

A solution of methyl 1-{[2-amino-2-(3,5-difluorophenyl)propyl]amino}cyclohexane carboxylate from Step F (205 mg, 0.628 mmol), and AcOH (0.36 mL, 6.28 mmol) in xylenes (5 mL) was heated at 80° C. for 3 h, allowed to cool, then poured into saturated aqueous $NaHCO_3$ (5 mL). The resulting mixture was extracted with EtOAc (2×10 mL). The combined organic extracts were dried over $Na_2SO_4$, filtered, and concentrated under reduced pressure. The crude product was purified by silica gel chromatography, eluting with a gradient of EtOAc:MeOH—100:0 to 92:8, to give the racemic product. The enantiomers were separated by HPLC, using a ChiralPak AD column and eluting with hexane:EtOH: Et₂NH—40:60:0.1. The first major peak to elute was (3R)-3-(3,5-difluorophenyl)-3-methyl-1,4-diazaspiro[5.5]undecan-5-one, the title compound, and the second major peak to elute was (3S)-3-(3,5-difluorophenyl)-3-methyl-1,4-diazaspiro[5.5]undecan-5-one. MS: m/z=295 (M+1).

Intermediate 3

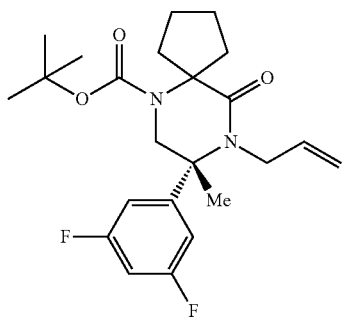 [SMILES: C=CCN1C(=O)C2(CCCC2)N(C(=O)OC(C)(C)C)C[C@@]1(C)c1cc(F)cc(F)c1]

tert-Butyl (8R)-9-allyl-8-(3,5-difluorophenyl)-8-methyl-10-oxo-6,9-diazaspiro[4.5]decane-6-carboxylate Step A. tert-Butyl (8R)-8-(3,5-difluorophenyl)-8-methyl-10-oxo-6,9-diazaspiro[4.5]decane-6-carboxylate A mixture of (8R)-8-(3,5-difluorophenyl)-8-methyl-6,9-diazaspiro[4.5]decan-10-one (5.50 g, 19.6 mmol), N,N-diisopropylethylamine (3.43 mL, 19.6 mmol), and di-tert-butyl dicarbonate (21.4 g, 98 mmol) in acetonitrile (150 mL) was stirred at 60° C. for 18 h, then cooled and concentrated under reduced pressure. The crude product was purified by silica gel chromatography, eluting with a gradient of hexane:EtOAc—95:5 to 50:50, to give the title compound.

Step B. tert-Butyl (8R)-9-allyl-8-(3,5-difluorophenyl)-8-methyl-10-oxo-6,9-diazaspiro[4.5]decane-6-carboxylate A solution of tert-butyl (8R)-8-(3,5-difluorophenyl)-8-methyl-10-oxo-6,9-diazaspiro[4.5]decane-6-carboxylate (500 mg, 1.314 mmol) in 2 ml of DMF was added to a suspension of sodium hydride (49.8 mg, 1.971 mmol). When the gas evolution had ceased, allyl bromide (0.171 mL, 1.971 mmol) was added to the ice cooled solution. After 18 hours, the reaction was quenched with brine and extracted with ethyl acetate (3×30 mL). The combined organic layers were washed with brine, dried over Na₂SO₄, filtered and concentrated in vacuo. The oily residue was purified on silica gel, eluting with a gradient of ethyl acetate:hexanes—0:100 to 50:50. The clean fractions were concentrated in vacuo to yield the title compound. MS: m/z=421 (M+1).

Intermediate 4

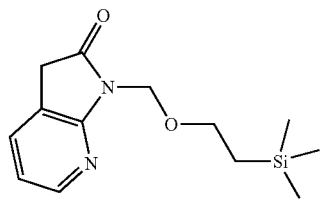 [SMILES: C[Si](C)(C)CCOCN1C(=O)Cc2cccnc21]

1-{[2-(Trimethylsilyl)ethoxy]methyl}-1,3-dihydro-2H-pyrrolo[2,3-b]pyridin-2-one

Step A. 1-{[2-(Trimethylsilyl)ethoxy]methyl}-1H-pyrrolo[2,3-b]pyridine

Sodium hydride (60% dispersion in mineral oil; 16.2 g, 0.404 mol) was added in portions over 25 min to a solution of 7-azaindole (39.8 g, 0.337 mol) in DMF (200 mL) at 0° C. and the mixture was stirred for 1 h. 2-(Trimethylsilyl)ethoxymethyl chloride (71.8 mL, 0.404 mol) was then added slowly over 15 min, keeping the temperature of the reaction mixture below 10° C. After 1 h, the reaction was quenched with water (500 mL) and the mixture was extracted with CH₂Cl₂ (5×300 mL). The combined organic layers were washed with saturated brine, dried over MgSO₄, filtered, concentrated and dried under high vacuum to give the title compound. MS: m/z=249 (M+1).

Step B. 3,3-Dibromo-1-{[2-(trimethylsilyl)ethoxy]methyl}-1,3-dihydro-2H-pyrrolo[2,3-b]pyridin-2-one A solution of 1-{[2-(trimethylsilyl)ethoxy]methyl}-1H-pyrrolo[2,3-b]pyridine from Step A (43.1 g, 0.1735 mol) in dioxane (300 mL) was added dropwise over 30 min to a suspension of pyridine hydrobromide perbromide (277 g, 0.8677 mol) in dioxane (300 mL). The reaction was stirred at ambient temperature using an overhead mechanical stirrer to produce two layers. After 60 min, the reaction was quenched with water (300 mL) and extracted with EtOAc (500 mL). The aqueous layer was extracted further with EtOAc (2×300 mL) and the combined organic layers were washed with H₂O (4×300 mL; the final wash was pH 5-6), then brine (300 mL), dried over MgSO₄, filtered and concentrated in vacuo. The crude product was immediately dissolved in CH₂Cl₂ and the solution filtered through a plug of silica, eluting with CH₂Cl₂ until the dark red color had completely eluted from the plug. The filtrate was washed with saturated aqueous NaHCO₃ (400 mL), then brine (400 mL), dried over MgSO₄ filtered, and concentrated in vacuo to give the title compound. MS: m/z=423 (M+1).

Step C. 1-{[2-(Trimethylsilyl)ethoxy]methyl}-1,3-dihydro-2H-pyrrolo[2,3-b]pyridin-2-one Zinc (100 g, 1.54 mol) was added to a solution of 3,3-dibromo-1-{[2-(trimethylsilyl)ethoxy]methyl}-1,3-dihydro-2H-pyrrolo[2,3-b]pyridin-2-one (65 g, 0.154 mol) in THF (880 mL) and saturated aqueous NH₄Cl (220 mL). After 3 h, the reaction mixture was filtered and concentrated in vacuo.

The residue was partitioned between EtOAc and H₂O which resulted in the formation of a white precipitate. Both layers were filtered through a Celite pad and the layers were separated. The aqueous layer was washed with EtOAc (2×500 mL) and the combined organic layers were washed with H₂O, dried over MgSO₄, filtered, and concentrated under reduced pressure. The crude product was purified by silica gel chromatography, eluting with CH₂Cl₂:EtOAc—90:10, to give the title compound. MS: m/z=265 (M+1).

Intermediate 5

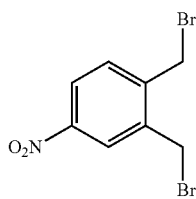 [SMILES: O=[N+]([O-])c1ccc(CBr)c(CBr)c1]

1,2-Bis(bromomethyl)-4-nitrobenzene

Step A. (4-Nitro-1,2-phenylene)dimethanol

A solution of 4-nitrophthalic acid (40 g, 189.5 mmol) in THF (500 mL) was added dropwise over 1.5 h to a solution of borane-THF complex (1 M, 490 mL, 490 mmol), keeping the reaction temperature between 0° C. and 5° C. After the addition, the reaction mixture was allowed to warm slowly to ambient temperature and stirred for 18 h. MeOH (100 mL) was added carefully and the precipitated solid dissolved. The mixture was concentrated in vacuo to about 500 mL, cooled to 0° C., and 10 N NaOH was added to adjust the pH to 10-11. This mixture was extracted with EtOAc (3×600 mL) and the combined organic layers were washed with brine, dried over Na₂SO₄, filtered, and concentrated in vacuo to give the title compound. MS: m/z=207 (M−OH+CH₃CN).

Step B. 1,2-Bis(bromomethyl)-4-nitrobenzene

Phosphorus tribromide (20.1 mL, 212 mmol) in Et₂O (250 mL) was added dropwise over 1.5 h to a solution of (4-nitro-1,2-phenylene)dimethanol from Step A (35.3 g, 193 mmol) in Et₂O (750 mL). After 18 h, the reaction mixture was cooled to 0° C. and quenched with H₂O (100 mL). The layers were separated and the organic layer was washed with H₂O (2×200 mL), then saturated aqueous NaHCO₃, dried over Na₂SO₄, filtered, and concentrated in vacuo to give the title compound. MS: m/z=309 (M+1).

Intermediate 6

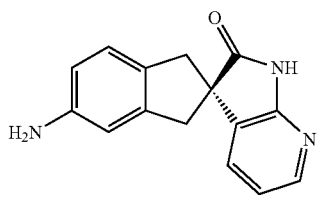 [SMILES: Nc1ccc2c(c1)C[C@@]1(C2)C(=O)Nc2ncccc21]

(R)-5-Amino-1,3-dihydrospiro[indene-2,3'-pyrrolo[2,3-b]pyridin]-2'(1'H)-one

Step A. (±)-5-Nitro-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-nitrobenzene (40.9 g, 132 mmol, described in Intermediate 5) and 1-{[2-(trimethylsilyl)ethoxy]methyl}-1,3-dihydro-2H-pyrrolo[2,3-b]pyridin-2-one (31.5 g, 119 mmol, described in Intermediate 4) in DMF (2 L) was added cesium carbonate (129 g, 397 mmol), portionwise, over 5 min. After 18 h, acetic acid (7.6 mL) was added and the mixture was concentrated to a volume of about 500 mL, then partitioned between EtOAc (1.5 L) and H₂O (1 L). The organic layer was washed with H₂O (1 L), then brine (500 mL), then dried over Na₂SO₄, filtered, and concentrated in vacuo. The crude product was purified by silica gel chromatography, eluting with a gradient of hexane:EtOAc—100:0 to 0:100, to give the title compound. MS: m/z=412 (M+1).

Step B. (±)-5-Amino-1'-{[2-(trimethylsilyl)ethoxy]methyl}-1,3-dihydrospiro[indene-2,3'-pyrrolo[2,3-b]pyridin]-2'(1'H)-one A mixture of 10% Pd/C (3 g) and (±)-5-nitro-1'-{[2-(trimethylsilyl)ethoxy]methyl}-1,3-dihydrospiro[indene-2,3'-pyrrolo[2,3-b]pyridin]-2'(1'H)-one from Step A (19.1 g, 46.4 mmol) was stirred vigorously in EtOH (400 mL) under an atmosphere of hydrogen (ca. 1 atm). After 18 h, the mixture was filtered through a pad of Celite, washing extensively with MeOH, and the filtrate was concentrated in vacuo to give the title compound. MS: m/z=382 (M+1).

Step C. tert-Butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate A solution of (±)-5-amino-1'-{[2-(trimethylsilyl)ethoxy]methyl}-1,3-dihydrospiro[indene-2,3'-pyrrolo[2,3-b]pyridin]-2'(1'H)-one from Step B (104 g, 273 mmol) and di-tert-butyl dicarbonate (71.5 g, 328 mmol) in CHCl₃ (1 L) was heated to reflux for 17 h. The cooled mixture was concentrated in vacuo and the residue was purified by silica gel chromatography, eluting with hexane:EtOAc—100:0 to 50:50, to give the racemic product. The enantiomers were resolved by HPLC, utilizing a ChiralPak AD column and eluting with EtOH. The first major peak to elute was tert-butyl (S)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, and the second major peak to elute was tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate, the title compound. MS: m/z=482 (M+1).

Step D. (R)-5-Amino-1,3-dihydrospiro[indene-2,3'-pyrrolo[2,3-b]pyridin]-2'(1'H)-one A solution of tert-butyl(R)-(2'-oxo-1'-{[2-(trimethylsilyl)ethoxy]methyl}-1,1',2',3-tetrahydrospiro[indene-2,3'-pyrrolo[2,3-b]pyridin]-5-yl)carbamate from Step C (13.4 g, 27.8 mmol) in MeOH (300 mL) was saturated with HCl (g). The mixture was resaturated with HCl (g) every 30 min until the starting material was consumed, and then concentrated in vacuo. The residue was dissolved in MeOH (150 mL) and treated with ethylenediamine (1.9 mL, 27.8 mmol) and 10 N sodium hydroxide (6 mL, 60 mmol) to adjust the mixture to pH 10. After 30 min, the mixture was diluted with H₂O (400 mL) and extracted with CHCl₃ (1 L). The organic layer was dried over Na₂SO₄, filtered, and concentrated in vacuo. The crude material was triturated with MeOH (35 mL) to give the title compound. MS: m/z=252 (M+1).

Intermediate 7

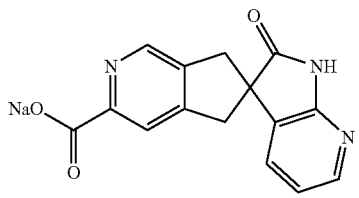

(±)-Sodium 2'-oxo-1',2',5,7-tetrahydrospiro[cyclopenta[c]pyridine-6,3'-pyrrolo[2,3-b]pyridine]-3-carboxylate Step A.
4,5-Bis(hydroxymethyl)pyridine-2-carbonitrile To a solution of dimethyl 6-cyanopyridine-3,4-dicarboxylate (2.00 g, 9.08 mmol) [Hashimoto et al. (1997) Heterocycles 46, 581] in EtOH (50 mL) was added lithium borohydride (4.54 mL of a 2 M solution in THF, 9.08 mmol) dropwise. The reaction mixture was stirred at ambient temperature for 3 h, and then cooled to 0° C. Saturated aqueous NaHCO₃ (20 mL) was added slowly and the quenched mixture was extracted with EtOAc (9×100 mL). The combined organic extracts were dried over Na₂SO₄, filtered, and concentrated in vacuo. The crude product was purified by silica gel chromatography, eluting with a gradient of CH₂Cl₂:MeOH—100:0 to 85:15, to give the title compound. MS: m/z=165 (M+1).

Step B. 4,5-Bis(bromomethyl)pyridine-2-carbonitrile

To a solution of 4,5-bis(hydroxymethyl)pyridine-2-carbonitrile from Step A (750 mg, 4.57 mmol) in THF (15 mL) was added phosphorus tribromide (1.61 g, 5.94 mmol) in THF (5 mL) dropwise. The reaction mixture was stirred at ambient temperature for 2 h, and then cooled to 0° C. Saturated aqueous NaHCO₃ (5 mL) was added slowly and the quenched mixture was extracted with CHCl₃ (2×30 mL). The combined organic extracts were dried over Na₂SO₄, filtered, and concentrated in vacuo. The crude product was purified by silica gel chromatography, eluting with a gradient of hexane:EtOAc—100:0 to 25:75, to give the title compound. MS: m/z=291 (M+1).

Step C. (±)-2'-Oxo-1',2',5,7-tetrahydrospiro[cyclopenta[c]pyridine-6,3'-pyrrolo[2,3-b]pyridine]-3-carbonitrile To a solution of 4,5-bis(bromomethyl)pyridine-2-carbonitrile from Step B (2.56 g, 8.83 mmol) and 1,3-dihydro-2H-pyrrolo[2,3-b]pyridin-2-one [Marfat & Carta (1987) Tetrahedron Lett. 28, 4027] (1.18 g, 8.83 mmol) in THF (120 mL) and H₂O (60 mL) was added lithium hydroxide monohydrate (1.11 g, 26.5 mmol). After 20 min, the reaction mixture was poured onto water (100 mL) and extracted with EtOAc (3×100 mL). The combined organic extracts were dried over Na₂SO₄, filtered, and concentrated in vacuo. The crude product was purified by silica gel chromatography, eluting with a gradient of CH₂Cl₂:MeOH: NH₄OH—100:0:0 to 95:5:1, to give the title compound. MS: m/z=263 (M+1).

Step D. (±)-Sodium 2'-oxo-1',2',5,7-tetrahydrospiro[cyclopenta[c]pyridine-6,3'-pyrrolo[2,3-b]pyridine]-3-carboxylate To a solution of (±)-2'-oxo-1',2',5,7-tetrahydrospiro[cyclopenta[c]pyridine-6,3'-pyrrolo[2,3-b]pyridine]-3-carbonitrile from Step C (1.53 g, 5.83 mmol) in EtOH (20 mL) was added 5 M aqueous NaOH (3.50 mL). The mixture was heated at reflux for 72 h, with additional 5 M aqueous NaOH (2.00 mL) added at 6 h. The reaction mixture was allowed to cool and was concentrated to dryness in vacuo to afford the title compound in sufficient purity for use in subsequent steps. MS: m/z=282 (M+1).

Intermediate 8

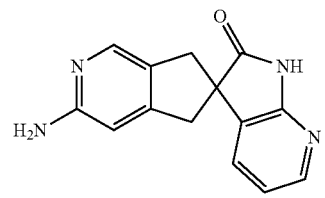 [SMILES: Nc1cc2c(cn1)CC1(C2)C(=O)Nc2ncccc21]

(±)-3-Amino-5,7-dihydrospiro[cyclopenta[c]pyridine-6,3'-pyrrolo[2,3-b]pyridin]-2'(1'H)-one Step A. (±)-tert-Butyl (2'-oxo-1',2',5,7-tetrahydrospiro[cyclopenta[c]pyridine-6,3'-pyrrolo[2,3-b]pyridin]-3-yl)carbamate To a suspension of (±)-sodium 2'-oxo-1',2',5,7-tetrahydrospiro[cyclopenta[c]pyridine-6,3'-pyrrolo[2,3-b]pyridine]-3-carboxylate (1.64 g, 5.83 mmol, described in Intermediate 7) and triethylamine (1.62 mL, 11.7 mmol) in tert-butanol (50 mL) was added diphenylphosphoryl azide (1.89 mL, 8.75 mmol) and the mixture was heated at reflux for 72 h. Additional diphenylphosphoryl azide (1.89 mL, 8.75 mmol) was added after 24 h and 56 h. The reaction mixture was concentrated in vacuo and then partitioned between CH₂Cl₂ (75 mL) and saturated NaHCO₃ (100 mL). The organic layer was separated and the aqueous layer was further extracted with CH₂Cl₂ (2×50 mL). The combined organic layers were dried over Na₂SO₄, filtered, and concentrated in vacuo. The crude product was purified by silica gel chromatography, eluting with a gradient of CH₂Cl₂:MeOH: NH₄OH—100:0:0 to 95:5:1, to give the title compound. MS: m/z=353 (M+1).

Step B. (±)-3-Amino-5,7-dihydrospiro[cyclopenta[c]pyridine-6,3'-pyrrolo[2,3-b]pyridin]-2'(1'H)-one trifluoroacetate A solution of (±)-tert-butyl (2'-oxo-1',2',5,7-tetrahydrospiro[cyclopenta[c]pyridine-6,3'-pyrrolo[2,3-b]pyridin]-3-yl)carbamate from Step A (131 mg, 0.372 mmol) was stirred in CH$_2$Cl$_2$ (10 mL) and TFA (3 mL) for 18 h and then concentrated in vacuo to provide the title compound. MS: m/z=253 (M+1).

Intermediate 9

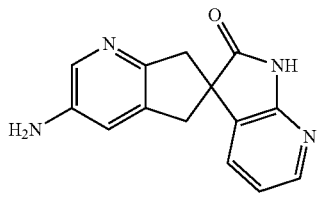 [SMILES: Nc1cnc2c(c1)CC1(C2)C(=O)Nc2ncccc21]

(±)-3-Amino-5,7-dihydrospiro[cyclopenta[b]pyridine-6,3'-pyrrolo[2,3-b]pyridin]-2'(1'H)-one trifluoroacetate Step A. (±)-1'-{[2-(Trimethylsilyl)ethoxy]methyl}-3H-spiro[cyclopentane-1,3'-pyrrolo[2,3-b]pyridine]-2',3(1'H)-dione To a solution of 1-{[2-(trimethylsilyl)ethoxy]methyl}-1,3-dihydro-2H-pyrrolo[2,3-b]pyridin-2-one (2.50 g, 9.46 mmol, described in Intermediate 4) and cesium carbonate (6.78 g, 20.8 mmol) in DMF (45 mL) was added dropwise a solution of 1,4-dibromobutan-2-one (1.59 mL, 12.3 mmol) [de Meijere et al. (2001) Eur. J. Org. Chem. 3789] in DMF (45 mL). After 68 h, the mixture was partitioned between Et$_2$O (200 mL) and H$_2$O (200 mL). The organic layer was separated and the aqueous layer was further extracted with Et$_2$O (2×100 mL). The combined organic layers were dried over Na$_2$SO$_4$, filtered, and concentrated in vacuo. The crude product was purified by silica gel chromatography, eluting with a gradient of hexane:EtOAc—100:0 to 75:25, to give the title compound. MS: m/z=333 (M+1).

Step B. (±)-3-Nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of (±)-1'-{[2-(trimethylsilyl)ethoxy]methyl}-3H-spiro[cyclopentane-1,3'-pyrrolo[2,3-b]pyridine]-2',3(1'H)-dione from Step A (230 mg, 0.692 mmol) and 1-methyl-3,5-dinitropyridin-2(1H)-one (173 mg, 0.869 mmol) [Tohda et al. (1990) Bull. Chem. Soc. Japan 63, 2820] in 2 M ammonia in MeOH (3.5 mL) was heated to reflux for 18 h. The mixture was concentrated in vacuo and purified by silica gel chromatography, eluting with a gradient of hexane:EtOAc—100:0 to 50:50, to give the title compound. MS: m/z=413 (M+1).

Step C. (±)-3-Amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one A mixture of 10% Pd/C (20 mg) and (±)-3-nitro-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step B (117 mg, 0.284 mmol) was stirred vigorously in MeOH (5 mL) under an atmosphere of hydrogen (ca. 1 atm). After 4.5 h, the mixture was filtered through a pad of Celite, washing extensively with MeOH, and the filtrate was concentrated in vacuo to give the title compound. MS: m/z=383 (M+1).

Step D. (±)-3-Amino-5,7-dihydrospiro[cyclopenta[b]pyridine-6,3'-pyrrolo[2,3-b]pyridin]-2'(1'H)-one trifluoroacetate A solution of (±)-3-amino-1'-{[2-(trimethylsilyl)ethoxy]methyl}-5,7-dihydrospiro[cyclopenta[b]pyridine-6,3'-pyrrolo[2,3-b]pyridin]-2'(1'H)-one from Step C (117 mg, 0.306 mmol) in MeOH (5 mL) was saturated with HCl (g). The mixture was stirred for 30 min and then concentrated in vacuo. The residue was dissolved in MeOH (3 mL), treated with ethylenediamine (0.020 mL, 0.306 mmol), and 10 N sodium hydroxide was added to adjust the mixture to pH 10. After 1 h, the reaction mixture was purified directly by HPLC using a reversed phase C18 column and eluting with a gradient of H$_2$O:CH$_3$CN:CF$_3$CO$_2$H—90:10:0.1 to 5:95:0.1. MS: m/z=253 (M+1).

Intermediate 10

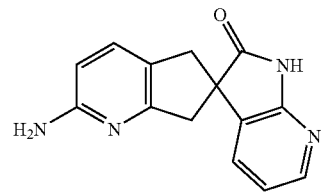 [SMILES: Nc1ccc2c(n1)CC1(C2)C(=O)Nc2ncccc21]

(±)-2-Amino-5,7-dihydrospiro[cyclopenta[b]pyridine-6,3'-pyrrolo[2,3-b]pyridin]-2'(1'H)-one Step A. Dimethyl 6-cyanopyridine-2,3-dicarboxylate To a solution of dimethylpyridine-2,3-dicarboxylate 1-oxide [Niiyami et al. (2002) Bioorg. Med. Chem. Lett. 12, 3041] (15.3 g, 72.5 mmol) and trimethylsilyl cyanide (15.7 mL, 117 mmol) in DME (161 mL) was added dimethylcarbamoyl chloride (10.5 mL, 114 mmol). The reaction mixture was heated at reflux for 72 h, and then cooled to 0° C. Saturated aqueous NaHCO$_3$ (800 mL) was added slowly and the quenched mixture was extracted with EtOAc (2×1 L). The combined organic extracts were washed with brine (200 mL), dried over Na$_2$SO$_4$, filtered, and concentrated in vacuo. The crude product was purified by silica gel chromatography, eluting with a gradient of hexane:EtOAc—100:0 to 50:50, to give the title compound. MS: m/z=221 (M+1).

Step B. 5,6-Bis(hydroxymethyl)pyridine-2-carbonitrile

To a solution of dimethyl 6-cyanopyridine-2,3-dicarboxylate from Step A (13.0 g, 59.0 mmol) in EtOH (295 mL) was added lithium borohydride (29.5 mL of a 2 M solution in THF, 59.0 mmol) dropwise. The reaction mixture was stirred at ambient temperature for 4 h, and then cooled to 0° C. Saturated aqueous NaHCO$_3$ (200 mL) was added slowly and the quenched mixture was extracted with EtOAc (9×100 mL). The combined organic extracts were dried over Na$_2$SO$_4$, filtered, and concentrated in vacuo. The crude product was purified by silica gel chromatography, eluting with a gradient of CH₂Cl₂:MeOH—100:0 to 85:15, to give the title compound. MS: m/z=165 (M+1).

Step C. 5,6-Bis(bromomethyl)pyridine-2-carbonitrile

To a solution of 5,6-bis(hydroxymethyl)pyridine-2-carbonitrile from Step B (2.50 g, 15.2 mmol) in THF (76 mL) was added phosphorus tribromide (5.36 g, 19.8 mmol) in THF (20 mL) dropwise. The reaction mixture was stirred at ambient temperature for 2 h, and then cooled to 0° C. Saturated aqueous NaHCO₃ (20 mL) was added slowly and the quenched mixture was extracted with CH₂Cl₂ (2×200 mL). The combined organic extracts were dried over Na₂SO₄, filtered, and concentrated in vacuo. The crude product was purified by silica gel chromatography, eluting with a gradient of hexane:EtOAc—100:0 to 30:70, to give the title compound. MS: m/z=291 (M+1).

Step D. (±)-2'-Oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile To a solution of 5,6-bis(bromomethyl)pyridine-2-carbonitrile from Step C (1.80 g, 6.21 mmol) and 1-{[2-(trimethylsilyl)ethoxy]methyl}-1,3-dihydro-2H-pyrrolo[2,3-b]pyridin-2-one (1.64 g, 6.21 mmol, described in Intermediate 2) in DMF (207 mL) was added cesium carbonate (6.07 g, 18.6 mmol), portionwise, over 5 min. After 18 h, the mixture was partitioned between CH₂Cl₂ (100 mL), saturated aqueous NaHCO₃ (100 mL) and brine (200 mL). The organic layer was removed and the aqueous layer was extracted further with CH₂Cl₂ (2×100 mL). The combined organic extracts were dried over Na₂SO₄, filtered, and concentrated in vacuo. The crude product was purified by silica gel chromatography, eluting with a gradient of hexane:EtOAc—100:0 to 10:90, to give the title compound. MS: m/z=393 (M+1).

Step E. (±)-2'-Oxo-1',2',5,7-tetrahydrospiro[cyclopenta[b]pyridine-6,3'-pyrrolo[2,3-b]pyridine]-2-carboxylic acid To a solution of (±)-2'-oxo-1'-{[2-(trimethylsilyl)ethoxy]methyl}-1',2',5,7-tetrahydrospiro[cyclopenta[b]pyridine-6,3'-pyrrolo[2,3-b]pyridine]-2-carbonitrile from Step D (690 mg, 1.76 mmol) in THF (5 mL) was added 3 N aqueous HCl (36 mL). The mixture was heated at reflux for 18 h, allowed to cool and concentrated to dryness in vacuo. The reaction mixture was dissolved in water (12 mL) and purified directly by HPLC using a reversed phase C18 column and eluting with a gradient of H₂O:CH₃CN:CF₃CO₂H—95:5:0.1 to 5:95:0.1. Lyophilization of the product-containing fractions provided the title compound. MS: m/z=282 (M+1).

Step F. (±)-tert-Butyl (2'-oxo-1',2',5,7-tetrahydrospiro[cyclopenta[b]pyridine-6,3'-pyrrolo[2,3-b]pyridin]-2-yl)carbamate To a suspension of (±)-2'-oxo-1',2',5,7-tetrahydrospiro[cyclopenta[b]pyridine-6,3'-pyrrolo[2,3-b]pyridine]-2-carboxylic acid from Step E (224 mg, 0.796 mmol) and triethylamine (0.333 mL, 2.39 mmol) in tert-butanol (5 mL) was added diphenylphosphoryl azide (0.258 mL, 1.20 mmol) and the mixture was heated at reflux for 1 h. The reaction mixture was concentrated in vacuo and then partitioned between CH₂Cl₂ (20 mL) and saturated NaHCO₃ (20 mL). The organic layer was separated and the aqueous layer was further extracted with CH₂Cl₂ (2×20 mL). The combined organic layers were dried over Na₂SO₄, filtered, and concentrated in vacuo. The crude product was purified by silica gel chromatography, eluting with a gradient of CH₂Cl₂:MeOH:NH₄OH—100:0:0 to 95:5:1, to give the title compound. MS: m/z=353 (M+1).

Step G. (±)-2-Amino-5,7-dihydrospiro[cyclopenta[b]pyridine-6,3'-pyrrolo[2,3-b]pyridin]-2'(1'H)-one A solution of (±)-tert-butyl (2'-oxo-1',2',5,7-tetrahydrospiro-[cyclopenta[b]pyridine-6,3'-pyrrolo[2,3-b]pyridin]-2-yl)carbamate from Step F (147 mg, 0.417 mmol) was stirred in CH₂Cl₂ (6 mL) and TFA (1 mL) for 3 h and then concentrated in vacuo to provide the title compound as the TFA salt. MS: m/z=253 (M+1).

Intermediate 11

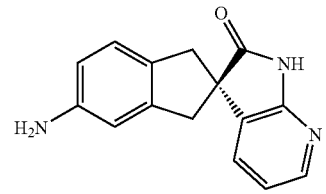 [SMILES: Nc1ccc2c(c1)C[C@@]1(C2)C(=O)Nc2ncccc21]

(R)-5-Hydroxy-1,3-dihydrospiro[indene-2,3'-pyrrolo[2,3-b]pyridin]-2'(1'H)-one

A solution of sodium nitrite (275 mg, 3.98 mmol) in water (1.6 mL) was slowly added to a cooled mixture of (R)-5-amino-1,3-dihydrospiro[indene-2,3'-pyrrolo[2,3-b]pyridin]-2'(1'H)-one (1 g, 3.98 mmol, described in Intermediate 3) in of 10% aqueous H₂SO₄ (8 mL) at 0° C. The ice bath was removed and the reaction allowed to stir at ambient temperature. The reaction mixture was then placed into a 70° C. oil bath and the bath was heated to 100° C. Bubbling was observed and heating was continued until LCMS indicated that the reaction was complete. The reaction was slowly neutralized by addition of 30% NH₄OH (ca. 2 mL) and the precipitate was collected by filtration and washed with water. The solid was then air dried and chromatographed by first mixing with silica and dry loading on a silica gel column. The product was eluted. with (10% MeOH/CH₂Cl₂). Concentration of the product containing fractions gave the title compound. MS: m/z=253 (M+1).

Intermediate 12

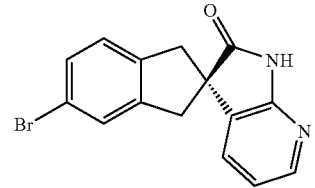 [SMILES: O=C1Nc2ncccc2[C@]12Cc1ccc(Br)cc1C2]

(R)-5-Bromo-1,3-dihydrospiro[indene-2,3'-pyrrolo[2,3-b]pyridin]-2'(1'H)-one

To a solution of (R)-5-amino-1,3-dihydrospiro[indene-2,3'-pyrrolo[2,3-b]pyridin]-2'(1'H)-one (500 mg, 1.99 mmol, described in Intermediate 3) in 48% HBr (4 mL) at 0° C. was added slowly over 10 min a solution of sodium nitrite (137 mg, 1.99 mmol) in water (0.8 mL). After 5 minutes CuBr (285 mg, 1.99 mmol) was added and the reaction mixture was placed into a 100° C. oil bath and heated at 100° C. for 20 min. The reaction mixture was then diluted with water followed by 2.5 mL of 30% $NH_4OH$ (2.5 mL) and the resulting solid was collected by filtration and washed with water. The solid was air dried and chromatographed by first mixing with silica and dry loading on a silica gel column. The product was eluted. with (10% $MeOH/CH_2Cl_2$). Concentration of the product containing fractions gave the title compound. to 740 mg and ~2 g of silica gel was added. The mixture was dry-loaded on to a silica gel column and the product was eluted with a gradient of $EtOAc:hexanes:CH_2Cl_2$—10:80:10 to 70:20:10. The product containing fractions were combined and concentrated at reduced pressure to give the title compound. MS: m/z=315 (M+1).

Intermediate 13

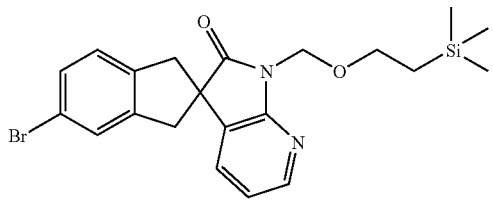

(±)-5-Bromo-1'-{[2-(trimethylsilyl)ethoxy]methyl}-1,3-dihydrospiro[indene-2,3'-pyrrolo[2,3-b]pyridin]-2'(1'H)-one To a solution of 1,2-bis(bromomethyl)-4-bromobenzene (40.9 g, 132 mmol) and 1-{[2-(trimethylsilyl)ethoxy]methyl}-1,3-dihydro-2H-pyrrolo[2,3-b]pyridin-2-one (31.5 g, 119 mmol, described in Intermediate 4) in MeOH (2 L) was added cesium carbonate (129 g, 397 mmol), portionwise, over 5 min. After 18 h, the mixture was concentrated to a volume of about 500 mL, then partitioned between EtOAc (1.5 L) and $H_2O$ (1 L). The organic layer was washed with $H_2O$ (1 L), then brine (500 mL), then dried over $Na_2SO_4$, filtered, and concentrated in vacuo. The crude product was purified by silica gel chromatography, eluting with a gradient of hexane:EtOAc—100:0 to 0:100, to give the title compound. MS: m/z=445 (M+1).

Intermediate 14

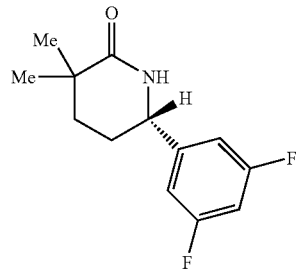 [SMILES: CC1(C)CC[C@@H](c2cc(F)cc(F)c2)NC1=O]

(6S)-6-(3,5-Difluorophenyl)-3,3-dimethylpiperidin-2-one

Step A. Dimethyl 2,2-dimethylpentanedioate

To a solution of 3,3-dimethyldihydro-2H-pyran-2,6(3H)-dione (20.0 g, 141 mmol) in MeOH (140 mL), at ambient temperature and under a constant stream of nitrogen, was added TMSCl (7.64 g, 70.3 mmol). The reaction mixture was then heated to 60° C. for 3.25 h, before being cooled to ambient temperature. The reaction mixture was then concentrated in vacuo before being diluted with diethyl ether (200 mL) and water (100 mL). The organics were then washed with 100 mL, individually, of each of the following aqueous solutions: 1 M NaOH, 1 M HCl, water, half-saturated brine and saturated brine. The organics were then dried over sodium sulfate, filtered and concentrated in vacuo to give the title compound, which was used without further purification. MS: m/z=189 (M+1).

Step B. 5-Methoxy-4,4-dimethyl-5-oxopentanoic acid

To a solution of dimethyl 2,2-dimethylpentanedioate from Step A (25.4 g, 135 mol) in MeOH (150 mL), THF (100 mL) and water (100 mL), was added potassium carbonate (36.2 g, 262 mmol). This biphasic solution was allowed to stir for 68 h, at ambient temperature, after which time the reaction was about 50% complete. Solvents were carefully removed in vacuo such that the starting materials did not vaporize. The aqueous layer was diluted with water (266 mL) and then extracted exhaustively with diethyl ether. The aqueous layer was made acidic by the addition of 6 M HCl (95 mL), saturated with NaCl, and extracted with diethyl ether (250 mL). This ethereal layer was washed with brine, dried over sodium sulfate, filtered and concentrated in vacuo to give the title compound. MS: m/z=175 (M+1).

Step C. Methyl 5-[methoxy(methyl)amino]-2,2-dimethyl-5-oxopentanoate

To a solution of 5-methoxy-4,4-dimethyl-5-oxopentanoic acid from Step B (7.00 g, 40.2 mmol), in $CH_2Cl_2$, was added DMF (0.1 mL), followed by the slow addition of oxalyl chloride (5.00 g, 39.4 mmol) over 30 min, during which time the reaction flask was maintained under a constant stream of dry nitrogen. Stirring was continued under a light stream of dry nitrogen for an additional hour, during which time the rate of carbon dioxide evolution diminished. This freshly formed acid chloride was then transferred via canula into a 500 mL round bottom flask, cooled to 0° C., which contained N-methoxymethanamine hydrochloride (5.76 g, 59.1 mmol) and triethylamine (15.9 g, 158 mmol). The ice bath was removed after 15 min and the reaction was allowed to warm to ambient temperature. After 1 h at ambient temperature, diethyl ether (100 mL) was added to precipitate some of the triethylamine hydrochloride, which was filtered and washed with more diethyl ether. The combined organics were then washed with 1 N HCl (2×100 mL), 1 N NaOH (100 mL), water (100 mL), half-saturated brine (100 mL) and saturated brine (100 mL). The organic layer was dried over sodium sulfate, filtered and concentrated in vacuo to provide the title compound which was used without further purification. MS: m/z=218 (M+1).

Step D. Methyl 5-(3,5-difluorophenyl)-2,2-dimethyl-5-oxopentanoate

To a solution of methyl 5-[methoxy(methyl)amino]-2,2-dimethyl-5-oxopentanoate from Step C (4.68 g, 21.6 mmol) in THF (47 mL), cooled to 0° C., was added 3,5-difluorophenylmagnesium bromide (65 mL, 0.5 M in THF, 32.3 mmol) over 30 min. The reaction mixture was allowed to stir at ambient temperature for 2 h, then re-cooled to 0° C. Additional 3,5-difluorophenylmagnesium bromide (50 mL, 0.5 M in THF, 25.0 mmol) was added over 30 min. After a further 3 h at 0° C., the reaction was quenched by the rapid addition of a cold (0° C.) solution of EtOH (71 mL) and conc. HCl (5.0 mL). The resulting mixture was then diluted with water (200 mL) and diethyl ether (400 mL). The organics were washed with water (3×200 mL) and brine (100 mL), then dried over sodium sulfate, filtered, and concentrated in vacuo to give a residue. This residue was purified by silica gel chromatography, eluting with a gradient of CH$_2$Cl$_2$:hexanes—50:50 to 100:0, to give the title compound. MS: m/z=239 (M−OCH$_3$).

Step E. Methyl (5S)-5-{[(S)-tert-butylsulfinyl]amino}-5-(3,5-difluorophenyl)-2,2-dimethylpentanoate To a solution of methyl 5-(3,5-difluorophenyl)-2,2-dimethyl-5-oxopentanoate from Step D (500. mg, 1.85 mmol) and (S)-2-methylpropane-2-sulfinamide (336 mg, 2.78 mmol) in THF (6.5 mL), was added titanium tetraethoxide (616 mg, 2.52 mmol). The reaction vessel was quickly sealed and heated at 60° C. for 3 h. After cooling to ambient temperature a septum and nitrogen inlet were attached prior to cooling to 0° C. Sodium borohydride (191 mg, 5.05 mmol) was then added, and a complete reaction was observed after 15 min. MeOH was slowly added until gas evolution stopped. The reaction mixture was diluted with saturated brine (6.5 mL) while experiencing rapid stirring. The resultant slurry was filtered through celite, washing with EtOAc as needed. The filtrate was washed with brine, dried over sodium sulfate, filtered and concentrated in vacuo to give an oil. This oil was purified by silica gel chromatography, eluting with a gradient of EtOAc:Hexanes—10:90 to 70:30, to give the title compound containing about 12% of the corresponding ethyl ester. MS: m/z=376 (M+1).

Step F. (6S)-6-(3,5-Difluorophenyl)-3,3-dimethylpiperidin-2-one

A solution of methyl (5S)-5-{[(S)-tert-butylsulfinyl]amino}-5-(3,5-difluorophenyl)-2,2-dimethylpentanoate from Step E (300 mg, 0.800 mmol) in MeOH (16 mL) was cooled to 0° C. Hydrogen chloride gas (anhydrous) was bubbled through this cold solution for about 30 seconds, after which time the reaction vessel was sealed and allowed to sit in the ice bath for 15 minutes. Dry nitrogen was then bubbled through the solution for 30 minutes, prior to removal of solvent in vacuo. More MeOH (~50 mL) was added, and then removed in vacuo. After dissolving in a third volume of MeOH (16 mL), triethylamine (323 mg, 3.2 mmol) was introduced and the mixture was heated to 65° C. for 16 hours. After cooling to ambient temperature, the solvent was removed in vacuo and the residue was partitioned between diethyl ether (50 mL) and 1 N HCl (50 mL). The organics were washed with additional 1 N HCl (50 mL), water (50 mL) and saturated brine (50 mL). The ethereal solution was dried over sodium sulfate, filtered and then concentrated in vacuo to provide the title compound, which could be used without further purification. MS: m/z=240 (M+1).

Intermediate 15

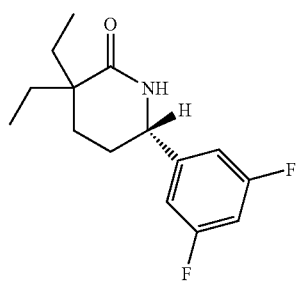 [SMILES: CCC1(CC)CC[C@@H](c2cc(F)cc(F)c2)NC1=O]

[(6S)-6-(3,5-Difluorophenyl)-3,3-diethyl-2-oxopiperidin-1-yl]acetic acid

Step A. Ethyl (5S)-5-{[(S)-tert-butylsulfinyl]amino}-5-(3,5-difluorophenyl)pentanoate To a solution of ethyl 5-(3,5-difluorophenyl)-5-oxovalerate (5.00 g, 19.5 mmol) and (S)-2-methylpropane-2-sulfinamide (2.88 g, 23.8 mmol) in THF (123 mL) was added titanium tetraethoxide (8.18 mL, 39.0 mmol). The reaction vessel was quickly sealed and placed into a 60° C. bath for 16 h. After cooling to ambient temperature a septum and nitrogen inlet were attached prior to cooling to 0° C. Sodium borohydride (1.48 g, 39.0 mmol) was then added, and a complete reaction was observed after 1 h. Methyl alcohol was then slowly added until gas evolution had stopped. The reaction mixture was then diluted with brine (60 mL) while experiencing rapid stirring. The resultant slurry was filtered through celite, washing with EtOAc as needed. The combined organics were then washed with brine, dried over sodium sulfate, filtered and concentrated in vacuo to give an oil, which was purified by silica gel chromatography, eluting with a gradient of EtOAc:hexanes—10:90 to 50:50, to give the title compound. MS: m/z=362 (M+1).

Step B. (6S)-6-(3,5-Difluorophenyl)-piperidin-2-one

A solution of ethyl (5S)-5-{[(S)-tert-butylsulfinyl]amino}-5-(3,5-difluorophenyl)pentanoate from Step A (4.42 g, 12.2 mmol) in MeOH (200 mL) was cooled to 0° C. Hydrogen chloride gas (anhydrous) was bubbled through this cold solution for about 1 minute, after which time the reaction vessel was sealed and allowed to sit in the ice bath for 15 minutes. Dry nitrogen was then bubbled through the solution for 30 minutes, prior to removal of solvent in vacuo. More MeOH (~50 mL) was added, and then removed in vacuo. After dissolving in a third volume of MeOH (100 mL), triethylamine (6.78 mL, 48.9 mmol) was introduced and the mixture was heated to 65° C. for 3 hours. After cooling to ambient temperature, the solvent was removed in vacuo and the residue was partitioned between diethyl ether (100 mL) and 1 M HCl (50 mL). The organics were washed with additional 1 M HCl (50 mL), water (50 mL) and saturated brine (50 mL). The ethereal solution was dried over sodium sulfate, filtered and then concentrated in vacuo to provide the title compound, which could be used without further purification. MS: m/z=212 (M+1).

Step C. tert-Butyl (2S)-2-(3,5-difluorophenyl)-6-oxopiperidine-1-carboxylate A solution of (6S)-6-(3,5-difluorophenyl)-piperidin-2-one from Step B (2.08 g, 9.85 mmol), di-tert-butyl dicarbonate (4.30 g, 19.7 mmol), and 4-dimethylaminopyridine (1.20 g, 9.85 mmol) in $CH_2Cl_2$ (50 mL) was stirred at ambient temperature for 20 h. An additional portion of di-tert-butyl dicarbonate (1.25 g, 5.73 mmol) was added and the solution stirred for a further 16 h. The solvent was removed under reduced pressure and the residue was purified by silica gel chromatography, eluting with a gradient of hexane:EtOAc—100:0 to 0:100, to give the title compound. MS: m/z=256 (M−$C_4H_7$).

Step D. tert-Butyl (6S)-6-(3,5-difluorophenyl)-3,3-diethylpiperidin-2-one-1-carboxylate To a solution of tert-butyl (2S)-2-(3,5-difluorophenyl)-6-oxopiperidine-1-carboxylate from Step C (1.53 g, 4.91 mmol) and iodoethane (0.993 mL, 12.3 mmol) in THF (15 mL) at −78° C. was added a 1 M solution of sodium bis(trimethylsilyl)amide in THF (10.8 mL, 10.8 mmol) dropwise over 15 min. The resulting mixture was stirred at −78° C. for 10 min and at 0° C. for 2 h, then quenched with saturated aqueous $NH_4Cl$ (50 mL) and extracted with EtOAc (3×50 mL). The combined organic layers were dried over $Na_2SO_4$, filtered, and concentrated in vacuo. The crude product was purified by silica gel chromatography, eluting with a gradient of hexane:EtOAc—100:0 to 50:50, to give the title compound. MS: m/z=312 (M−$C_4H_7$).

Step E. (6S)-6-(3,5-Difluorophenyl)-3,3-diethylpiperidin-2-one

To a solution of tert-butyl (6S)-6-(3,5-difluorophenyl)-3,3-diethylpiperidin-2-one-1-carboxylate from Step D (1.22 g, 3.32 mmol) in $CH_2Cl_2$ (7 mL) at ambient temperature was added TFA (3 mL). After stirring for 1.5 h, the reaction mixture was concentrated in vacuo. The residue was partitioned between $CH_2Cl_2$ (30 mL) and saturated $NaHCO_3$ (30 mL). The layers were separated and the aqueous layer was further extracted with $CH_2Cl_2$ (2×30 mL). The combined organics were dried over sodium sulfate, filtered and then concentrated in vacuo to provide the title compound, which could be used without further purification. MS: m/z=268 (M+1).

Intermediate 16

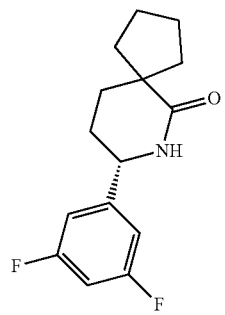 [SMILES: O=C1N[C@H](c2cc(F)cc(F)c2)CCC12CCCC2]

(8S)-8-(3,5-Difluorophenyl)-7-azaspiro[4.5]decan-6-one

Prepared in two steps from tert-butyl (2S)-2-(3,5-difluorophenyl)-6-oxopiperidine-1-carboxylate (Intermediate 15 Step C) by a procedure substantially as described above for Intermediate 15 but replacing 1,4-diiodobutane for iodoethane in Step D. MS: m/z=266 (M+1).

Intermediate 17

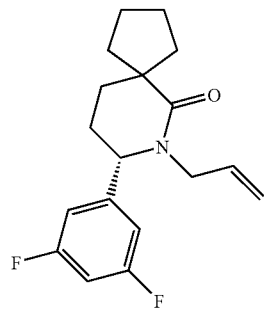 [SMILES: C=CCN1C(=O)C2(CCCC2)CC[C@H]1c1cc(F)cc(F)c1]

(8S)-7-Allyl-8-(3,5-difluorophenyl)-7-azaspiro[4.5]decan-6-one

Prepared from (8S)-8-(3,5-difluorophenyl)-7-azaspiro[4.5]decan-6-one (Intermediate 16) by a procedure identical to that described in Intermediate 3 Step B. MS: m/z=306 (M+1).

Intermediate 18

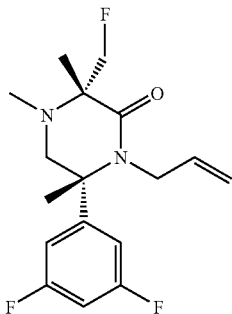 [SMILES: C=CCN1C(=O)[C@@](C)(CF)N(C)C[C@@]1(C)c1cc(F)cc(F)c1]

(±)-cis-6-(3,5-Difluorophenyl)-3-(fluoromethyl)-3,4,6-trimethyl-1-(prop-2-en-1-yl)piperazin-2-one

Step A. (±)-Methyl 2-methylserinate hydrochloride

Thionyl chloride (12.8 mL, 175 mmol) was added dropwise to a stirred suspension of DL-2-methylserine hydrate, (10.4 g, 88.0 mmol) in anhydrous methanol (67 mL) at 0° C. The solids gradually dissolved during the addition. Upon complete addition the bath was removed and the mixture stirred at room temperature overnight. The solvent was then removed in vacuo to give an oil which was azeotroped twice with ether and further dried under vacuum to give the title compound.

Step B. (±)-Methyl O-[tert-butyl(dimethyl)silyl]-2-methylserinate

A mixture of (±)-methyl 2-methylserinate hydrochloride from Step A (14.4 g, 85.0 mmol) and imidazole (19.1 g, 280 mmol) in dry DMF (77 mL) was cooled to 0° C. and treated with tert-butyldimethylsilyl chloride (14.1 g, 93.0 mmol). The mixture was stirred at 0° C. for 25 min, and was then allowed to warm to ambient temperature and stirred for 18 h. Water (500 mL) was added and the mixture extracted with ether (4×150 mL). The combined organic extracts were washed successively with water and brine, dried (anhydrous Na$_2$SO$_4$), filtered and concentrated in vacuo. Purification of the residue by silica gel chromatography, eluting with a gradient of EtOAc:CH$_2$Cl$_2$—0:100 to 100:0, afforded the title compound. MS: m/z=248 (M+1).

Step C. Methyl N-{2-[(tert-butoxycarbonyl)amino]-2-(3,5-difluorophenyl)propyl}-O-[tert-butyl(dimethyl)silyl]-2-methylserinate and propan-2-yl N-{2-[(tert-butoxycarbonyl)amino]-2-(3,5-difluorophenyl)propyl}-O-[tert-butyl(dimethyl)silyl]-2-methylserinate (±)-Methyl O-[tert-butyl(dimethyl)silyl]-2-methylserinate from Step B (13.75 g, 55.6 mmol) and tert-butyl[1-(3,5-difluorophenyl)-1-methyl-2-oxoethyl]carbamate (6.34 g, 22.2 mmol, described in Intermediate 1) were combined in titanium(IV) isopropoxide (9.77 mL, 33.3 mmol) and EtOAc (2 mL) at room temperature. The EtOAc was carefully removed in vacuo to give a thick mixture which was then stirred at ambient temperature for 2 h. The mixture was diluted with MeOH (38 mL), cooled in an ice bath and treated successively with acetic acid (12.7 mL, 222 mmol) and sodium cyanoborohydride (1.68 g, 26.7 mmol). After 2 min, the ice bath was removed and the mixture was allowed to warm to ambient temperature. After 30 min the reaction mixture was poured into saturated aqueous NaHCO$_3$ solution (500 mL) and EtOAc (800 mL) with vigorous stirring. The mixture was filtered to remove the precipitated solids and the residue rinsed thoroughly with EtOAc. The layers of the filtrate were separated and the organic layer washed with water and brine, dried over Na$_2$SO$_4$, filtered and concentrated in vacuo. Purification of the residue by silica gel chromatography, eluting with a gradient of EtOAc:hexanes—0:100 to 100:0, afforded a mixture of the title compounds (~1:1 ratio of isopropyl:methyl esters by LCMS analysis) as an oil which was used directly in the next step. MS: m/z=545 (M+1, isopropyl ester), 517 (M+1, methyl ester).

Step D. 6-(3,5-Difluorophenyl)-3-(hydroxymethyl)-3,6-dimethylpiperazin-2-one A 1:1 mixture of methyl N-{2-[(tert-butoxycarbonyl)amino]-2-(3,5-difluorophenyl)propyl}-O-[tert-butyl(dimethyl)silyl]-2-methylserinate and propan-2-yl N-{2-[(tert-butoxycarbonyl)amino]-2-(3,5-difluorophenyl)propyl}-O-[tert-butyl(dimethyl)silyl]-2-methylserinate from Step C (10.98 g, 20.65 mmol) and sulfuric acid (15.0 mL, 281 mmol) in n-BuOH (516 mL) was heated at reflux for 2 days. Most of the n-BuOH was removed in vacuo and the residual solution was cooled in an ice bath, diluted with EtOAc (200 mL) and quenched by portionwise addition of saturated aqueous NaHCO$_3$ solution (to pH ~8) with stirring. The layers were separated and the aqueous layer further extracted with EtOAc (200 mL). The combined organic extracts were washed successively with water and brine, and the combined aqueous layers were then saturated with NaCl (s) and further extracted with EtOAc (2×100 mL). The combined organic extracts were dried over Na$_2$SO$_4$, filtered and concentrated in vacuo. Purification of the residue by silica gel chromatography, eluting with a gradient of MeOH:CH$_2$Cl$_2$—0:100 to 10:90 afforded the title compound. MS: m/z=271 (M+1).

Step E. (±)-cis- and (±)-trans-6-(3,5-Difluorophenyl)-3-(hydroxymethyl)-3,4,6-trimethylpiperazin-2-one 6-(3,5-Difluorophenyl)-3-(hydroxymethyl)-3,6-dimethylpiperazin-2-one from Step D (135 mg, 0.50 mmol) was dissolved in MeOH (5.9 mL). Acetic acid (86 µL, 1.50 mmol) was added to adjust the pH to ~5, and the stirred mixture was then treated with aqueous formaldehyde (74 µL, 1.0 mmol). The mixture was stirred at room temperature for 5 min and was then treated with sodium cyanoborohydride (38 mg, 0.60 mmol). After 2 h the reaction was quenched by addition of saturated aqueous NaHCO$_3$ solution and the mixture extracted twice with EtOAc. The combined organic extracts were dried over Na$_2$SO$_4$, filtered and concentrated in vacuo. Purification of the residue was achieved by silica gel chromatography, eluting with a gradient of EtOAc:hexanes—40:60 to 100:0, to elute (±)-cis-6-(3,5-difluorophenyl)-3-(hydroxymethyl)-3,4,6-trimethylpiperazin-2-one, and then flushing with MeOH:CH$_2$Cl$_2$—10:90 to elute (±)-trans-6-(3,5-difluorophenyl)-3-(hydroxymethyl)-3,4,6-trimethylpiperazin-2-one. MS: m/z 285 (M+1).

Step F. (±)-cis-3-({[tert-Butyl(dimethyl)silyl]oxy}methyl)-6-(3,5-difluorophenyl)-3,4,6-trimethylpiperazin-2-one Imidazole (42 mg, 0.62 mmol) was added to a stirred solution of (±)-cis-6-(3,5-difluorophenyl)-3-(hydroxymethyl)-3,4,6-trimethylpiperazin-2-one from Step E (71 mg, 0.25 mmol) and tert-butyldimethylsilyl chloride (45 mg, 0.30 mmol) in dry DMF (1.3 mL) at 0° C. The ice bath was removed and the mixture stirred at ambient temperature for 18 h, and then at 40° C. for 1 h. The reaction mixture was partitioned between EtOAc and brine, diluted with a small volume of water, and the layers separated. The aqueous layer was further extracted with EtOAc (2×), and the combined organics were dried (anhydrous $Na_2SO_4$), filtered and concentrated in vacuo. The residue was purified by silica gel chromatography, eluting with a gradient of EtOAc:hexanes—0:100 to 100:0, to afford the title compound. MS: m/z 399 (M+1).

Step G. (±)-cis-3-({[tert-Butyl(dimethyl)silyl]oxy}methyl)-6-(3,5-difluorophenyl)-3,4,6-trimethyl-1-(prop-2-en-1-yl)piperazin-2-one A solution of (±)-cis-3-({[tert-butyl(dimethyl)silyl]oxy}methyl)-6-(3,5-difluorophenyl)-3,4,6-trimethylpiperazin-2-one from Step F (95 mg, 0.24 mmol) in DMF (1.9 mL) was cooled to 0° C., and treated with sodium hydride (60% dispersion in oil, 14 mg, 0.36 mmol). After a few minutes, allyl bromide (22 µL, 0.25 mmol) was added. The ice bath was removed and the mixture stirred at room temperature overnight. Additional sodium hydride (5 mg) and allyl bromide (6 µL) were added and the mixture stirred for another 2 h at ambient temperature. The mixture was then cooled to 0° C., quenched with saturated aqueous $NaHCO_3$, diluted with water, and extracted with EtOAc. The organic layer was dried (anhydrous $Na_2SO_4$), filtered and concentrated in vacuo. The residue was purified by silica gel chromatography, eluting with a gradient of EtOAc:hexanes—0:100 to 100:0, to afford the title compound. MS: m/z 439 (M+1).

Step H. (±)-cis-6-(3,5-Difluorophenyl)-3-(hydroxymethyl)-3,4,6-trimethyl-1-(prop-2-en-1-yl)piperazin-2-one TBAF (701 µL, 0.701 mmol) was added to a solution of (±)-cis-3-({[tert-butyl(dimethyl)silyl]oxy}methyl)-6-(3,5-difluorophenyl)-3,4,6-trimethyl-1-(prop-2-en-1-yl)piperazin-2-one from Step G (205 mg, 0.467 mmol) in THF (2.7 mL) at ambient temperature. After 4 h, additional TBAF (1.17 mL, 1.17 mmol) was added and the mixture was stirred for 18 h. The mixture was then partitioned between EtOAc and a mixture of saturated aqueous $NaHCO_3$ and brine. The layers were separated, the aqueous layer extracted once more with EtOAc, and the combined organics dried (anhydrous $Na_2SO_4$), filtered and concentrated in vacuo. The residue was purified by silica gel chromatography, eluting with a gradient of EtOAc:hexanes—70:30 to 100:0, to afford the title compound. MS: m/z 325 (M+1).

Step I. (±)-cis-6-(3,5-Difluorophenyl)-3-(fluoromethyl)-3,4,6-trimethyl-1-(prop-2-en-1-yl)piperazin-2-one A stirred solution of (±)-cis-6-(3,5-difluorophenyl)-3-(hydroxymethyl)-3,4,6-trimethyl-1-(prop-2-en-1-yl)piperazin-2-one from Step H (16 mg, 0.05 mmol) in anhydrous $CH_2Cl_2$ (0.6 mL) was cooled to −78° C. under nitrogen. DAST (8 µL, 0.06 mmol) was added and the mixture then allowed to warm to ambient temperature and stirring was continued for 18 h. The mixture was cooled to 0° C. and quenched by dropwise addition of saturated aqueous $NaHCO_3$. The mixture was extracted twice with $CH_2Cl_2$ and the combined organic extracts were dried over $Na_2SO_4$, filtered and concentrated in vacuo. The residue was purified by silica gel chromatography, eluting with a gradient of EtOAc:hexanes—0:100 to 50:50, to afford the title compound. MS: m/z 327 (M+1).

Intermediate 19

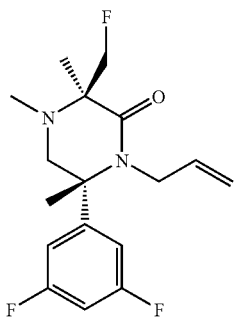 [SMILES: C=CCN1C(=O)[C@](C)(CF)N(C)C[C@@]1(C)c1cc(F)cc(F)c1]

(±)-trans-6-(3,5-Difluorophenyl)-3-(fluoromethyl)-3,4,6-trimethyl-1-(prop-2-en-1-yl)piperazin-2-one Essentially following the procedures described for Intermediate 18, but using (±)-trans-6-(3,5-difluorophenyl)-3-(hydroxymethyl)-3,4,6-trimethylpiperazin-2-one in place of (±)-cis-6-(3,5-difluorophenyl)-3-(hydroxymethyl)-3,4,6-trimethylpiperazin-2-one in Step F, the title compound was obtained. MS: m/z 327 (M+1).

Intermediate 20

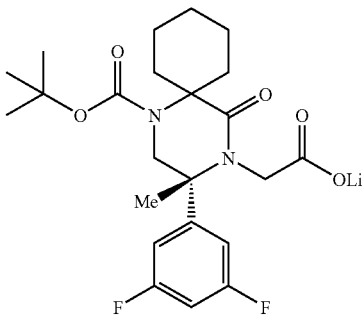

Lithium [(3R)-1-(tert-butoxycarbonyl)-3-(3,5-difluorophenyl)-3-methyl-5-oxo-1,4-diazaspiro[5.5]undec-4-yl]acetate

Step A. Di-tert-butyl[1-(3,5-difluorophenyl)ethyl]imidodicarbonate

To a solution of [1-(3,5-difluorophenyl)ethyl]amine (10.0 g, 63.6 mmol) in $CH_2Cl_2$ (200 mL) at 0° C. was added di-tert-butyl dicarbonate (13.9 g, 63.6 mmol) and the resulting mixture was stirred at ambient temperature for 18 h. The solvent was removed under reduced pressure. To the residue was added di-tert-butyl dicarbonate (20.8 g, 95.4 mmol) and DMAP (7.78 g, 63.6 mmol) and the reaction mixture was heated at 80° C. for 2 h. The mixture was allowed to cool and additional di-tert-butyl dicarbonate (69.4 g, 318 mmol) was added. The reaction mixture was heated at 80° C. for 2 h, allowed to cool, and concentrated in vacuo. The crude product was purified by silica gel chromatography, eluting with a gradient of hexane:EtOAc—98:2 to 90:10, to give the title compound. MS: m/z=421 (M+Na+CH$_3$CN).

Step B. tert-Butyl 2-[(tert-butoxycarbonyl)amino]-2-(3,5-difluorophenyl)propanoate To a stirred suspension of potassium tert-butoxide in THF (300 mL) at −78° C. was added a solution of di-tert-butyl[1-(3,5-difluorophenyl)ethyl]imidodicarbonate from Step A (22.0 g, 61.6 mmol) in THF (200 mL), dropwise, over 45 min. The reaction mixture was allowed to warm to ambient temperature and stirring was continued for 3 h. The reaction mixture was cooled to −78° C. and quenched with 1 N aqueous HCl (300 mL), warmed to 0° C., and poured into Et$_2$O (300 mL). The organic layer was extracted and the aqueous layer was extracted further with Et$_2$O (300 mL). The combined organic extracts were dried over Na$_2$SO$_4$, filtered, and concentrated in vacuo. The crude product was purified by silica gel chromatography, eluting with hexane:EtOAc—95:5 to 80:20, to give the title compound. MS: m/z=421 (M+Na+CH$_3$CN).

Step C. tert-Butyl[1-(3,5-difluorophenyl)-1-methyl-2-oxoethyl]carbamate

To a stirred solution of tert-butyl 2-[(tert-butoxycarbonyl)amino]-2-(3,5-difluorophenyl)propanoate from Step B (2.00 g, 5.60 mmol) in THF (20 mL) at −78° C. was added LiAlH$_4$ (5.60 mL of a 1 M solution in THF, 5.60 mmol), dropwise. The reaction mixture was stirred at −78° C. for 6 h, then quenched with EtOAc (5.6 mL), then H$_2$O (15.6 mL), then 1 N aqueous NaOH (5.6 mL), then EtOAc (17 mL). The reaction mixture was warmed to ambient temperature, stirred for 1 h, filtered, and extracted with EtOAc (2×40 mL). The organic extracts were dried over Na$_2$SO$_4$, filtered, and concentrated in vacuo to afford the title compound in sufficient purity for use in the next step. MS: m/z=186 (M−CO$_2$C$_4$H$_7$).

Step D. Methyl 1-aminocyclohexanecarboxylate hydrochloride

Essentially following the procedures described in Intermediate 1 for methyl 1-aminocyclopentanecarboxylate hydrochloride, but using 1-aminocyclohexanecarboxylic acid in place of 1-aminocyclopentanecarboxylic acid, the title compound was obtained. MS: m/z=158 (M+1).

Step E. Methyl 1-{[2-[(tert-butoxycarbonyl)amino]-2-(3,5-difluorophenyl)propyl]amino}cyclohexanecarboxylate A mixture of tert-butyl[1-(3,5-difluorophenyl)-1-methyl-2-oxoethyl]carbamate from Step C (500 mg, 1.75 mmol), methyl 1-aminocyclohexanecarboxylate hydrochloride from Step D (1.38 g, 8.76 mmol), and AcOH (0.301 mL, 5.26 mmol) in MeOH (15 mL) was stirred at ambient temperature for 30 min. NaCNBH$_3$ (165 mg, 2.63 mmol) was added and the pH of the mixture was checked and adjusted to pH ~5 as necessary by addition of AcOH. The reaction mixture was stirred at ambient temperature for 1 h, then quenched with saturated aqueous NaHCO$_3$ (10 mL) and extracted with CH$_2$Cl$_2$ (2×50 mL). The combined organic extracts were dried over Na$_2$SO$_4$, filtered, and concentrated in vacuo. The crude product was purified by silica gel chromatography, eluting with hexane:EtOAc—100:0 to 80:20, to give the title compound. MS: m/z=427 (M+1).

Step F. Methyl 1-{[2-amino-2-(3,5-difluorophenyl)propyl]amino}cyclohexanecarboxylate A solution of methyl 1-{[2-[(tert-butoxycarbonyl)amino]-2-(3,5-difluorophenyl)propyl]amino}cyclohexanecarboxylate from Step E (280 mg, 0.657 mmol) in EtOAc (5 mL) at 0° C. was saturated with HCl (g). The reaction mixture was aged at 0° C. for 30 min, then poured carefully into saturated aqueous NaHCO$_3$ (10 mL). The resulting mixture was extracted with EtOAc (2×15 mL). The combined organic extracts were dried over Na$_2$SO$_4$, filtered, and concentrated in vacuo to give the title compound. MS: m/z=327 (M+1).

Step G. (3R)-3-(3,5-Difluorophenyl)-3-methyl-1,4-diazaspiro[5.5]undecan-5-one A solution of methyl 1-{[2-amino-2-(3,5-difluorophenyl)propyl]amino}cyclohexanecarboxylate from Step F (205 mg, 0.628 mmol), and AcOH (0.36 mL, 6.28 mmol) in xylenes (5 mL) was heated at 80° C. for 3 h, allowed to cool, then poured into saturated aqueous NaHCO$_3$ (5 mL). The resulting mixture was extracted with EtOAc (2×10 mL). The combined organic extracts were dried over Na$_2$SO$_4$, filtered, and concentrated under reduced pressure. The crude product was purified by silica gel chromatography, eluting with a gradient of EtOAc:MeOH—100:0 to 92:8, to give the racemic product. The enantiomers were separated by HPLC, using a ChiralPak AD column and eluting with hexane:EtOH:Et$_2$NH—40:60:0.1. The first major peak to elute was (3R)-3-(3,5-difluorophenyl)-3-methyl-1,4-diazaspiro[5.5]undecan-5-one, the title compound, and the second major peak to elute was (3S)-3-(3,5-difluorophenyl)-3-methyl-1,4-diazaspiro[5.5]undecan-5-one. MS: m/z=295 (M+1).

Step H. tert-Butyl (3R)-3-(3,5-difluorophenyl)-3-methyl-5-oxo-1,4-diazaspiro[5.5]undecane-1-carboxylate A solution of (3R)-3-(3,5-difluorophenyl)-3-methyl-1,4-diazaspiro[5.5]undecan-5-one from Step G (90 mg, 0.306 mmol), N,N-diisopropylethylamine (0.027 mL, 0.153 mmol), and di-tert-butyl dicarbonate (667 mg, 3.06 mmol) in acetonitrile (2 mL) was stirred at 60° C. for 8 h, then cooled and concentrated under reduced pressure. The crude product was purified by silica gel chromatography, eluting with a gradient of hexane:EtOAc—95:5 to 50:50, to give the title compound. MS: m/z=339 (M−C$_4$H$_7$).

Step I. tert-Butyl (3R)-3-(3,5-difluorophenyl)-4-(2-ethoxy-2-oxoethyl)-3-methyl-5-oxo-1,4-diazaspiro[5.5]undecane-1-carboxylate To a stirred solution of tert-butyl (3R)-3-(3,5-difluorophenyl)-3-methyl-5-oxo-1,4-diazaspiro[5.5]undecane-1-carboxylate from Step H (60 mg, 0.152 mmol) in THF (0.5 mL) at 0° C. was added NaH (12 mg of a 60% dispersion in oil, 0.30 mmol). After 5 min, ethyl bromoacetate (437 mg, 2.62 mmol) was added and the mixture was allowed to warm to ambient temperature and stirring was continued for 1 h. Saturated aqueous NaHCO$_3$ (2 mL) was added and the mixture was extracted with EtOAc (2×5 mL). The combined organic layers were dried over Na$_2$SO$_4$, filtered, and concentrated in vacuo. The crude product was purified by silica gel chromatography, eluting with a gradient of hexane:EtOAc—95:5 to 60:40, to give the title compound. MS: m/z=425 (M−C$_4$H$_7$).

Step J. Lithium [(3R)-1-(tert-butoxycarbonyl)-3-(3,5-difluorophenyl)-3-methyl-5-oxo-1,4-diazaspiro[5.5]undec-4-yl]acetate To a solution of tert-butyl (3R)-3-(3,5-difluorophenyl)-4-(2-ethoxy-2-oxoethyl)-3-methyl-5-oxo-1,4-diazaspiro[5.5]undecane-1-carboxylate from Step I (65 mg, 0.135 mmol) in THF (1.5 mL) and H$_2$O (0.5 mL) was added 1 N aqueous LiOH (0.14 mL, 0.14 mmol) and the resulting mixture was stirred at ambient temperature for 1 h. The mixture was adjusted to pH 7 by addition of 1 N HCl and concentrated to dryness in vacuo to give the title compound. MS: m/z=397 (M−C$_4$H$_7$).

Intermediate 21

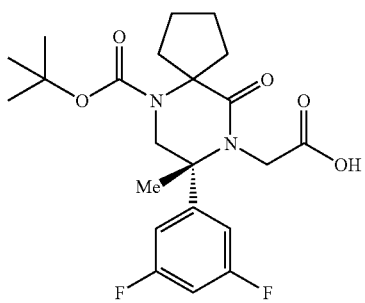 [SMILES: CC(C)(C)OC(=O)N1C[C@@](C)(c2cc(F)cc(F)c2)N(CC(=O)O)C(=O)C12CCCC2]

[(8R)-6-(tert-Butoxycarbonyl)-8-(3,5-difluorophenyl)-8-methyl-10-oxo-6,9-diazaspiro[4.5]dec-9-yl]acetic acid Essentially following the procedures described for Intermediate 20, but using methyl 1-aminocyclopentanecarboxylate hydrochloride in place of methyl 1-aminocyclohexanecarboxylate hydrochloride, the title compound was obtained. MS: m/z=383 (M−C$_4$H$_7$).

Intermediate 22

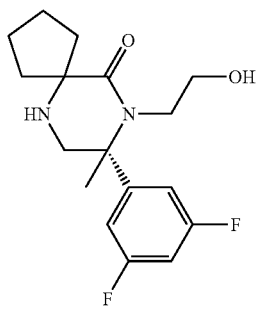 [SMILES: C[C@@]1(c2cc(F)cc(F)c2)CNC2(CCCC2)C(=O)N1CCO]

(8R)-8-(3,5-Difluorophenyl)-9-(2-hydroxyethyl)-8-methyl-6,9-diazaspiro[4.5]decan-10-one Step A. Methyl [(8R)-8-(3,5-difluorophenyl)-8-methyl-10-oxo-6,9-diazaspiro[4.5]dec-9-yl]acetate A mixture of [(8R)-6-(tert-butoxycarbonyl)-8-(3,5-difluorophenyl)-8-methyl-10-oxo-6,9-diazaspiro[4.5]dec-9-yl]acetic acid (4.41 g, 10.1 mmol, described in Intermediate 21) and conc. H$_2$SO$_4$ (3.0 mL) in MeOH (100 mL) was heated at reflux for 24 h. The reaction mixture was concentrated in vacuo to a volume of about 30 mL, poured into saturated aqueous NaHCO$_3$ (150 mL), and extracted with EtOAc (2×200 mL). The combined organic extracts were dried over Na$_2$SO$_4$, filtered, and concentrated in vacuo to afford the title compound. MS: m/z=353 (M+1).

Step B. (8R)-8-(3,5-Difluorophenyl)-9-(2-hydroxyethyl)-8-methyl-6,9-diazaspiro[4.5]decan-10-one To a stirred solution of methyl[(8R)-8-(3,5-difluorophenyl)-8-methyl-10-oxo-6,9-diazaspiro[4.5]dec-9-yl]acetate from Step A (998 mg, 2.83 mmol) in THF (14 mL) cooled to 0° C. via an ice/water bath was added LiAlH$_4$ (1 M in THF, 4.20 mL, 4.20 mmol). After 40 min, the reaction was quenched with water (40 mL), and the resulting mixture was filtered through Celite, washing with saturated NaHCO$_3$ solution (50 mL) and EtOAc (80 mL). The filtrate was separated and the aqueous layer was extracted an additional time with EtOAc (80 mL). The combined organic layers were dried over Na$_2$SO$_4$, filtered and concentrated in vacuo. The crude product was purified by silica gel chromatography, eluting with a gradient of EtOAc:Hexanes—0:100 to 100:0. The clean fractions were concentrated in vacuo to yield the title compound. MS: m/z=325 (M+1).

Intermediate 23

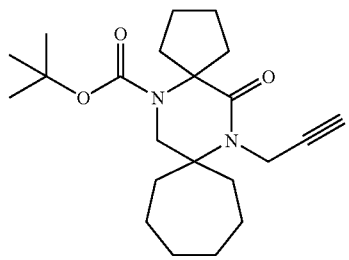 [SMILES: C#CCN1C(=O)C2(CCCC2)N(C(=O)OC(C)(C)C)CC12CCCCCC2]

tert-Butyl 16-oxo-15-prop-2-yn-1-yl-6,15-diazadispiro[4.2.6.2]hexadecane-6-carboxylate Step A. tert-Butyl 16-oxo-6,15-diazadispiro[4.2.6.2]hexadecane-6-carboxylate Essentially following the procedures described for Intermediate 1, but using methyl 1-[(tert-butoxycarbonyl)amino]cycloheptanecarboxylate in place of tert-butyl 2-[(tert-butoxycarbonyl)amino]-2-(3,5-difluorophenyl)propanoate, the title compound was obtained. MS: m/z=337 (M+1).

Step B. tert-Butyl 16-oxo-15-prop-2-yn-1-yl-6,15-diazadispiro[4.2.6.2]hexadecane-6-carboxylate Sodium hydride (23 mg, 0.575 mmol, 60% dispersion in mineral oil) was added to a stirred solution of tert-butyl 16-oxo-6,15-diazadispiro[4.2.6.2]hexadecane-6-carboxylate from Step A (92 mg, 0.273 mmol) in DMF (1 mL). When the gas evolution had ceased, propargyl bromide (70 mg, 0.471 mmol, 80 wt % in toluene) was added to the solution at ambient temperature. After 1 h, the reaction was quenched with water (30 mL) and extracted with EtOAc (30 mL). The organic layer was dried over Na₂SO₄, filtered and concentrated in vacuo to yield the title compound. MS: m/z=397 (M+Na).

Intermediate 24

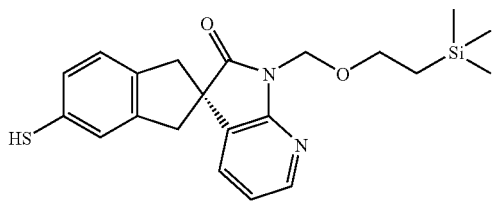 [SMILES: C[Si](C)(C)CCOCN1C(=O)[C@@]2(Cc3ccc(S)cc3C2)c2cccnc21]

(2R)-5-Sulfanyl-1'-{[2-(trimethylsilyl)ethoxy]methyl}-1,3-dihydrospiro[indene-2,3'-pyrrolo[2,3-b]pyridin]-2'(1'H)-one Step A. O-Ethyl S-[(2R)-2'-oxo-1,1',2',3-tetrahydrospiro[indene-2,3'-pyrrolo[2,3-b]pyridin]-5-yl]carbonodithioate To a stirred suspension of (2R)-5-amino-1,3-dihydrospiro[indene-2,3'-pyrrolo[2,3-b]pyridin]-2'(1'H)-one (940 mg, 3.74 mmol, described in Intermediate 6) in MeOH (10 mL) and THF (5 mL) was added conc. HCl (1 mL). The resulting solution was cooled to 0° C. and a solution of NaNO₂ (405 mg, 5.87 mmol) in H₂O (4 mL) was added dropwise over 1-2 min. The reaction mixture was aged at 0° C. for 15 min and added to a solution of potassium ethyl xanthate (2.015 g, 12.57 mmol) in H₂O (5 mL). The resulting mixture was heated at 65° C. for 1 h, then cooled and partitioned between water (150 mL) and EtOAc (150 mL). The organic layer was dried over Na₂SO₄, filtered and concentrated in vacuo. The crude product was purified on silica gel, eluting with a gradient of hexane:EtOAc—100:0 to 0:100, to yield the title compound. MS: m/z=357 (M+1).

Step B. O-Ethyl S-[(2R)-2'-oxo-1'-{[2-(trimethylsilyl)ethoxy]methyl}-1,1',2',3-tetrahydrospiro[indene-2,3'-pyrrolo[2,3-b]pyridin]-5-yl]carbonodithioate Sodium hydride (60% dispersion in mineral oil; 88 mg, 2.20 mmol) was added to a stirred solution of O-ethyl S-[(2R)-2'-oxo-1,1',2',3-tetrahydrospiro[indene-2,3'-pyrrolo[2,3-b]pyridin]-5-yl]carbonodithioate from Step A (653 mg, 1.83 mmol) in DMF (15 mL) and the mixture was aged for 15 min. 2-(Trimethylsilyl)ethoxymethyl chloride (0.408 mL, 2.30 mmol) was added to the reaction mixture and stirring was continued for 90 min. The reaction was quenched with H₂O (40 mL) and the mixture was extracted with EtOAc (50 mL). The organic layer was washed with brine (30 mL), dried over Na₂SO₄, filtered, and concentrated in vacuo. The crude product was purified on silica gel, eluting with a gradient of hexane:EtOAc—100:0 to 0:100, to yield the title compound. MS: m/z=487 (M+1).

Step C. (2R)-5-Sulfanyl-1'-{[2-(trimethylsilyl)ethoxy]methyl}-1,3-dihydrospiro[indene-2,3'-pyrrolo[2,3-b]pyridin]-2'(1'H)-one To a stirred solution of O-ethyl S-[(2R)-2'-oxo-1'-{[2-(trimethylsilyl)ethoxy]methyl}-1,1',2',3-tetrahydrospiro[indene-2,3'-pyrrolo[2,3-b]pyridin]-5-yl]carbonodithioate from Step B (740 mg, 1.52 mmol) in EtOH (4 mL) was added 1 N NaOH (3.0 mL, 3.0 mmol). The resulting suspension was heated at 60° C. for 90 min, then cooled and poured into H₂O (50 mL). The mixture was extracted with EtOAc (2×70 mL), and the combined organic layers were washed with brine (30 mL), dried over Na₂SO₄, filtered, and concentrated in vacuo to yield the title compound. MS: m/z=462 (M+Na+CH₃CN).

Intermediate 25

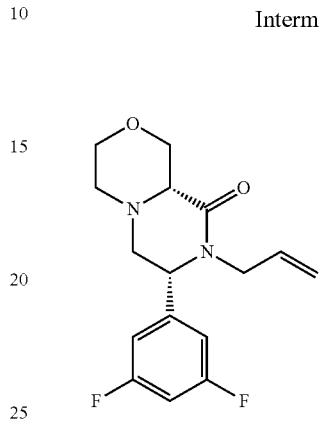

(7R,9aR)-8-Allyl-7-(3,5-difluorophenyl)hexahydropyrazino[2,1-c][1,4]oxazin-9(6H)-one Step A. Methyl (3R)-morpholine-3-carboxylate To a solution of (R)-morpholine-3,4-dicarboxylic acid-4-tert-butyl ester (5.00 g, 21.6 mmol) in MeOH (54 mL) was added thionyl chloride (3.16 mL, 43.2 mmol) dropwise, and the resulting mixture was heated at reflux for 16 h. The solution was cooled to ambient temperature and concentrated in vacuo. The residue was made basic with saturated aqueous NaHCO₃ and extracted with CH₂Cl₂ (3×). The combined organic extracts were dried over Na₂SO₄, filtered, and concentrated in vacuo to yield the title compound.

Step B. Methyl (3R)-4-[2-(3,5-difluorophenyl)-2-oxoethyl]morpholine-3-carboxylate To a mixture of methyl (3R)-morpholine-3-carboxylate from Step A (556 mg, 3.83 mmol) and 3,5-difluorophenacyl bromide (450 mg, 1.92 mmol) in CH₂Cl₂ (2 mL) was added DIPEA (0.669 mL, 3.83 mmol). The reaction mixture was stirred at ambient temperature for 1 h, then concentrated in vacuo. The crude product was purified on silica gel, eluting with hexane:EtOAc—75:25, to yield the title compound. MS: m/z=300 (M+1).

Step C. (7R,9aR)-8-Allyl-7-(3,5-difluorophenyl)hexahydropyrazino[2,1-c][1,4]oxazin-9(6H)-one To a stirred mixture of methyl (3R)-4-[2-(3,5-difluorophenyl)-2-oxoethyl]morpholine-3-carboxylate from Step B (365 mg, 1.22 mmol) and allylamine (0.101 mL, 1.34 mmol) in MeOH (5 mL) was added acetic acid (0.349 mL, 6.10 mmol). After 30 min NaCNBH₃ (100 mg, 1.59 mmol) was added and the solution was heated at 45° C. for 48 h. The mixture was cooled and concentrated in vacuo. The residue was diluted with EtOAc and washed with saturated aqueous NaHCO₃. The organic layer was dried over Na₂SO₄, filtered, concentrated in vacuo, and purified by HPLC using a reversed phase C18 column and eluting with a gradient of H₂O:CH₃CN:CF₃CO₂H—90:10:0.1 to 5:95:0.1, to give (7S,9aR)-8-allyl-7-(3,5-difluorophenyl)hexahydropyrazino[2,1-c][1,4]oxazin-9(6H)-one, which eluted first, and (7R,9aR)-8-allyl-7-(3,5-difluorophenyl)hexahydropyrazino[2,1-c][1,4]oxazin-9(6H)-one, the title compound, which eluted second. MS: m/z=309 (M+1).

Intermediate 26

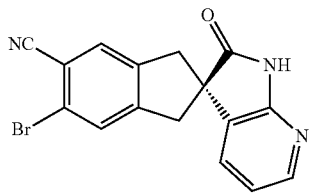 [SMILES: N#Cc1cc2c(cc1Br)C[C@@]1(C2)C(=O)Nc2ncccc21]

(2R)-6-Bromo-2'-oxo-1,1',2',3-tetrahydrospiro[indene-2,3'-pyrrolo[2,3-b]pyridine]-5-carbonitrile Step A. (2S)-5-Amino-6-iodo-1,3-dihydrospiro[indene-2,3'-pyrrolo[2,3-b]pyridin]-2'(1'H)-one To a solution of (2R)-5-amino-1,3-dihydrospiro[indene-2,3'-pyrrolo[2,3-b]pyridin]-2'(1'H)-one (4.00 g, 15.9 mmol, described in Intermediate 6) in THF (64 mL) at ambient temperature was added N-iodosuccinimide (3.58 g, 15.92 mmol). The reaction mixture was stirred for 18 h, then purified by silica gel chromatography, eluting with EtOAc:hexanes—70:30, to give the title compound. MS: m/z=378 (M+1).

Step B. (2R)-6-Amino-2'-oxo-1,1',2',3-tetrahydrospiro[indene-2,3'-pyrrolo[2,3-b]pyridine]-5-carbonitrile To a suspension of (2S)-5-amino-6-iodo-1,3-dihydrospiro[indene-2,3'-pyrrolo[2,3-b]pyridin]-2'(1'H)-one from Step A (750 mg, 1.99 mmol), zinc dust (15.6 mg, 0.24 mmol) and zinc cyanide (467 mg, 3.98 mmol) in DMF (3.4 mL) at ambient temperature was added bis(tri-t-butylphosphine)palladium (102 mg, 0.199 mmol). The reaction mixture was heated at 80° C. for 2 h, diluted with H₂O, and extracted with EtOAc (3×). The combined organic layers were filtered through a plug of Celite, dried over MgSO₄, filtered, and concentrated in vacuo. The oily residue was purified by silica gel chromatography, eluting with EtOAc:hexanes—80:20, to afford the title compound. MS: m/z=277 (M+1).

Step C. (2R)-6-Bromo-2'-oxo-1,1',2',3-tetrahydrospiro[indene-2,3'-pyrrolo[2,3-b]pyridine]-5-carbonitrile To a suspension of (2R)-6-amino-2'-oxo-1,1',2',3-tetrahydrospiro[indene-2,3'-pyrrolo[2,3-b]pyridine]-5-carbonitrile (200 mg, 0.72 mmol) in 25% HBr at 0° C. was added a solution of sodium nitrite (61.4 mg, 0.89 mmol) in H₂O (0.3 mL) dropwise. The cooled mixture was then added to a cooled solution of copper(I)bromide (107 mg, 0.746 mmol) in 48% HBr (0.557 mL, 4.92 mmol). The reaction mixture was stirred at 0° C. for 1 h then warmed to ambient temperature. H₂O (5 mL) was added and the mixture was made basic by addition of concentrated NH₄OH. The resulting precipitate was collected by filtration and washed with H₂O to provide the title compound in sufficient purity for the next step. MS: m/z=341 (M+1).

Intermediate 27

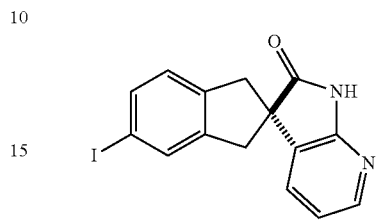

(R)-5-Iodo-1,3-dihydrospiro[indene-2,3'-pyrrolo[2,3-b]pyridin]-2'(1'H)-one

To a cooled 0° C. solution of (R)-5-amino-1,3-dihydrospiro[indene-2,3'-pyrrolo[2,3-b]pyridin]-2'(1'H)-one (1.05 g, 4.2 mmol, described in Intermediate 6) in H₂O (8 mL), THF (2 mL), and conc. HCl (1 mL) was added slowly over 1 min a solution of NaNO₂ (300 mg, 4.3 mmol) in H₂O (1 mL). After 30 min, a solution of KI (4.1 g, 21 mmol) in H₂O (3 mL) was added and the reaction mixture was stirred for an additional 30 min. The reaction was then diluted with saturated aqueous NaHCO₃ (150 mL) and extracted with CH₂Cl₂ (3×100 mL). The aqueous layer was filtered and further extracted with CH₂Cl₂ (2×100 mL). The combined organic extracts were dried over Na₂SO₄, filtered, and concentrated in vacuo to give a residue. This residue was purified by silica gel chromatography, eluting with a gradient of CH₂Cl₂:MeOH—100:0 to 92:8, to give the title compound. MS: m/z=363 (M+1).

Intermediate 28

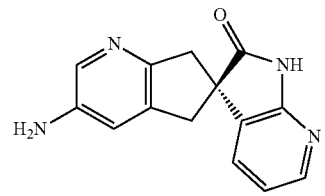 [SMILES: Nc1cnc2c(c1)C[C@@]1(C2)C(=O)Nc2ncccc21]

(6S)-3-Amino-5,7-dihydrospiro[cyclopenta[b]pyridine-6,3'-pyrrolo[2,3-b]pyridin]-2'(1'H)-one The racemic Intermediate 9 was resolved by HPLC, utilizing a ChiralPak AD column and eluting with EtOH. The first major peak to elute was (6S)-3-amino-5,7-dihydrospiro[cyclopenta[b]pyridine-6,3'-pyrrolo[2,3-b]pyridin]-2'(1'H)-one, the title compound, and the second major peak to elute was (6R)-3-amino-5,7-dihydrospiro[cyclopenta[b]pyridine-6,3'-pyrrolo[2,3-b]pyridin]-2'(1'H)-one. MS: m/z=253 (M+1).

Intermediate 29

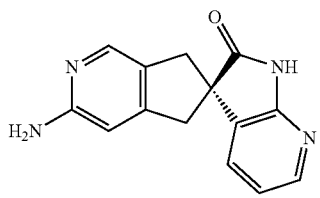 [SMILES: Nc1cc2c(cn1)C[C@]1(C2)C(=O)Nc2ncccc21]

(6S)-3-Amino-5,7-dihydrospiro[cyclopenta[c]pyridine-6,3'-pyrrolo[2,3-b]pyridin]-2'(1'H)-one The racemic Intermediate 10 was resolved by HPLC, utilizing a ChiralPak AD column and eluting with MeOH. The first major peak to elute was (6S)-3-amino-5,7-dihydrospiro[cyclopenta[c]pyridine-6,3'-pyrrolo[2,3-b]pyridin]-2'(1'H)-one, the title compound, and the second major peak to elute was (6R)-3-amino-5,7-dihydrospiro[cyclopenta[c]pyridine-6,3'-pyrrolo[2,3-b]pyridin]-2'(1'H)-one. MS: m/z=253 (M+1).

Intermediate 30

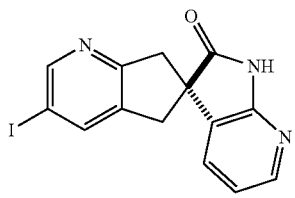

(6S)-3-Iodo-5,7-dihydrospiro[cyclopenta[b]pyridine-6,3'-pyrrolo[2,3-b]pyridin]-2'(1'H)-one To a cooled 0° C. solution of (6S)-3-amino-5,7-dihydrospiro[cyclopenta[b]pyridine-6,3'-pyrrolo[2,3-b]pyridin]-2'(1'H)-one (5.0 g, 20 mmol, described in Intermediate 28) in H$_2$O (24 mL), THF (6 mL), and conc. HCl (5 mL) was added slowly over 15 min a solution of NaNO$_2$ (1.4 g, 21 mmol) in H$_2$O (5 mL). After 30 min, a solution of KI (20 g, 120 mmol) in H$_2$O (30 mL) was added and the reaction mixture was stirred for an additional 30 min. The reaction mixture was diluted with 1 N NaOH (~70 mL) until most solid dissolved and the solution was basic and the resulting mixture was filtered. To the aqueous filtrate was added 1 N HCl to adjust the mixture to pH=6-6.5, at which time solid began to precipitate. The mixture was aged for 16 h, and the resulting solid was filtered, washed with H$_2$O, and dried to give the title compound. MS: m/z=364 (M+1).

Intermediate 31

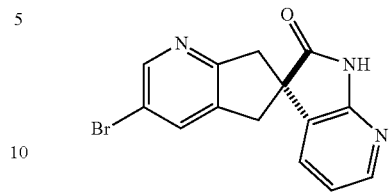

(6S)-3-Bromo-5,7-dihydrospiro[cyclopenta[b]pyridine-6,3'-pyrrolo[2,3-b]pyridin]-2'(1'H)-one Essentially following the procedures described for Intermediate 12, but using (6S)-3-amino-5,7-dihydrospiro[cyclopenta[b]pyridine-6,3'-pyrrolo[2,3-b]pyridin]-2'(1'H)-one in place of (R)-5-amino-1,3-dihydrospiro[indene-2,3'-pyrrolo[2,3-b]pyridin]-2'(1'H)-one, the title compound was obtained. MS: m/z=316 (M+1).

Intermediate 32

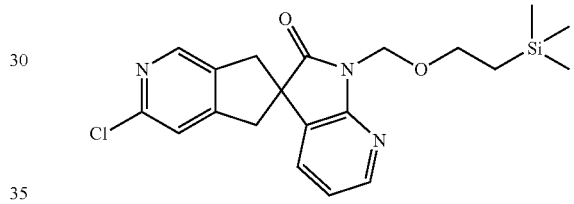

(±)-3-Chloro-1'-{[2-(trimethylsilyl)ethoxy]methyl}-5,7-dihydrospiro[cyclopenta[c]pyridine-6,3'-pyrrolo[2,3-b]pyridin]-2'(1'H)-one Step A. Dimethylpyridine-3,4-dicarboxylate 1-oxide To a stirred mixture of dimethylpyridine-3,4-dicarboxylate (10.13 g, 51.9 mmol) and urea hydrogen peroxide (9.80 g, 104 mmol) in CH$_3$CN (100 mL) at 0° C. was added dropwise trifluoroacetic anhydride (22.31 g, 106 mmol). The reaction mixture was stirred at 0° C. for 2 h, and then saturated aqueous sodium bisulfate (80 mL) was added slowly and the quenched mixture was diluted with 0.5 N HCl (300 mL) and extracted with CH$_2$Cl$_2$ (3×400 mL). The combined organic extracts were dried over Na$_2$SO$_4$, filtered, and concentrated in vacuo to give the title compound. MS: m/z=212 (M+1).

Step B. Dimethyl 6-chloropyridine-3,4-dicarboxylate

A mixture of dimethylpyridine-3,4-dicarboxylate 1-oxide from Step A (3.46 g, 16.37 mmol) and POCl$_3$ (25.1 g, 164 mmol) in CHCl$_3$ (15 mL) was heated at 85° C. for 18 h. The reaction mixture was allowed to cool and was poured onto ice. Saturated aqueous NaHCO$_3$ (800 mL) was added and the mixture was extracted with EtOAc (2×500 mL). The combined organic layers were dried over Na$_2$SO$_4$, filtered, and concentrated in vacuo. The residue was purified by silica gel chromatography, eluting with a gradient of EtOAc:hexanes—0:100 to 60:40, to afford the title compound. MS: m/z=230 (M+1).

Step C. (6-Chloropyridine-3,4-diyl)dimethanol

To a solution of dimethyl 6-chloropyridine-3,4-dicarboxylate from Step B (1.26 g, 5.50 mmol) in THF (10 mL) at 0° C. was added sodium borohydride (1.07 g, 28.2 mmol) carefully. To the resulting mixture was added MeOH (5 mL), dropwise, over 20 min. The reaction mixture was stirred at 0° C. for 1 h, then H$_2$O (5 mL) and 1 N HCl (5 mL) were added and the mixture was concentrated to dryness in vacuo. The residue was purified by silica gel chromatography, eluting with a gradient of CH$_2$Cl$_2$:MeOH:NH$_4$OH—100:0:0 to 80:20:0.2, to give the title compound. MS: m/z=174 (M+1).

Step D. 4,5-Bis(bromomethyl)-2-chloropyridine

A mixture of (6-chloropyridine-3,4-diyl)dimethanol from Step C (550 mg, 3.17 mmol) and SOBr$_2$ (6.7 g, 32 mmol) in CHCl$_3$ (10 mL) was heated at reflux for 18 h. The reaction mixture was allowed to cool, saturated aqueous NaHCO$_3$ (40 mL) was added carefully, and the mixture was extracted with EtOAc (2×80 mL). The combined organic layers were dried over Na$_2$SO$_4$, filtered, and concentrated in vacuo. The residue was purified by silica gel chromatography, eluting with a gradient of EtOAc:hexanes—0:100 to 100:0, to afford the title compound. MS: m/z=299.9 (M+1).

Step E. (±)-3-Chloro-1'-{[2-(trimethylsilyl)ethoxy]methyl}-5,7-dihydrospiro[cyclopenta[c]pyridine-6,3'-pyrrolo[2,3-b]pyridin]-2'(1'H)-one To a solution of 4,5-bis(bromomethyl)-2-chloropyridine from Step D (254 mg, 0.85 mmol) and 1-{[2-(trimethylsilyl)ethoxy]methyl}-1,3-dihydro-2H-pyrrolo[2,3-b]pyridin-2-one (226 mg, 0.86 mmol, described in Intermediate 4) in DMF (8 mL) was added cesium carbonate (455 mg, 1.40 mmol). After 21 h, the reaction mixture was poured into H$_2$O (60 mL) and extracted with EtOAc (2×60 mL). The organic layer was washed with brine (40 mL), then dried over Na$_2$SO$_4$, filtered, and concentrated in vacuo. The crude product was purified by silica gel chromatography, eluting with a gradient of hexanes:EtOAc—100:0 to 0:100, to give the title compound. MS: m/z=402 (M+1).

TABLE 1

Essentially following the procedures outlined for the Intermediates above, the Intermediates shown in Table 1 were prepared. Requisite starting materials were commercially available, known in the literature, described herein, or readily synthesized by one skilled in the art of organic synthesis.

| Intermediate | Structure | MS: m/z (M + 1) |
|---|---|---|
| 33 | 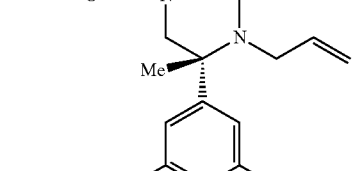 | 321 |
| 34 | 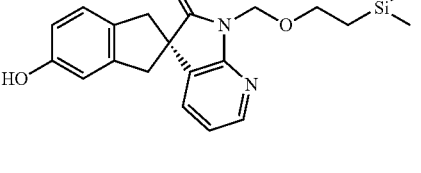 | 395 |
| 35 | 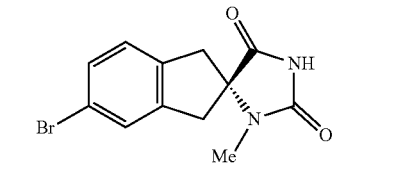 [SMILES: CN1C(=O)NC(=O)[C@@]12Cc1ccc(Br)cc1C2] | 383 |
| 36 | 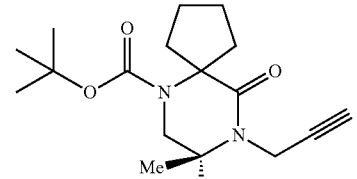 | 295 |
| 37 | 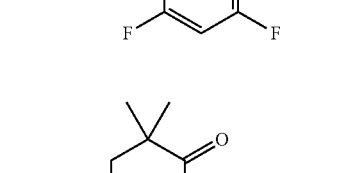 | 363 (M − C$_4$H$_7$) |
| 38 | 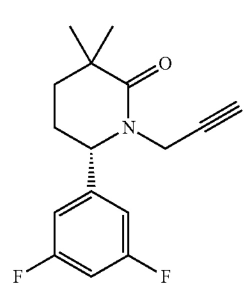 [SMILES: C#CCN1C(=O)C(C)(C)CC[C@H]1c1cc(F)cc(F)c1] | 278 |

TABLE 1-continued
Essentially following the procedures outlined for the Intermediates above, the Intermediates shown in Table 1 were prepared. Requisite starting materials were commercially available, known in the literature, described herein, or readily synthesized by one skilled in the art of organic synthesis.
| Intermediate | Structure | MS: m/z (M + 1) |
|---|---|---|
| 39 | 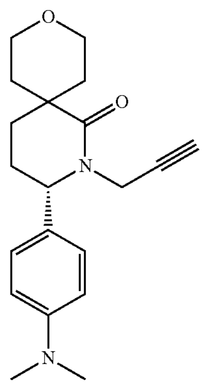 [SMILES: C#CCN1C(=O)C2(CCOCC2)CC[C@H]1c1ccc(N(C)C)cc1] | 327 |
| 40 | 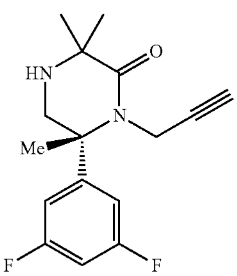 [SMILES: C#CCN1C(=O)C(C)(C)NC[C@@]1(C)c1cc(F)cc(F)c1] | 293 |
| 41 | 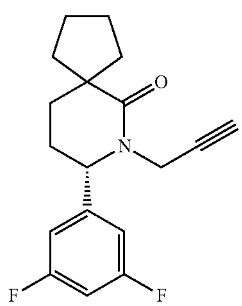 [SMILES: C#CCN1C(=O)C2(CCCC2)CC[C@H]1c1cc(F)cc(F)c1] | 304 |
| 42 | 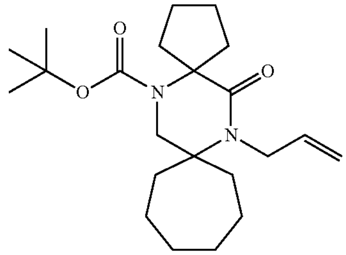 [SMILES: C=CCN1C(=O)C2(CCCC2)N(C(=O)OC(C)(C)C)CC12CCCCCC2] | 377 |
| 43 | | 307 |
| 44 | | 335 |
| 45 | | 355 |
Example 1
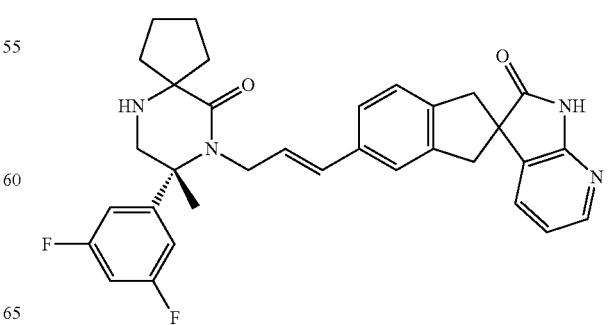

5-{(1E)-3-[(8R)-8-(3,5-difluorophenyl)-8-methyl-10-oxo-6,9-diazaspiro[4.5]dec-9-yl]prop-1-en-1-yl}-1,3-dihydrospiro[indene-2,3'-pyrrolo[2,3-]pyridin]-2'(1'H)-one Step A. tert-Butyl (8R)-8-(3,5-difluorophenyl)-8-methyl-10-oxo-9-[(2E)-3-(2'-oxo-1'-{[2-(trimethylsilyl)ethoxy]methyl}-1,1',2',3-tetrahydrospiro[indene-2,3'-pyrrolo[2,3-b]pyridin]-5-yl)prop-2-en-1-yl]-6,9-diazaspiro[4.5]decane-6-carboxylate A suspension of tert-butyl (8R)-9-allyl-8-(3,5-difluorophenyl)-8-methyl-10-oxo-6,9-diazaspiro[4.5]decane-6-carboxylate described in Intermediate 3 (0.292 g, 0.694 mmol) and 5-bromo-1'-{[2-(trimethylsilyl)ethoxy]methyl}-1,3-dihydrospiro[indene-2,3'-pyrrolo[2,3-b]pyridin]-2'(1'H)-one described in Intermediate 13 (309 mg, 0.694 mmol Palladium(II) acetate (46.8 mg, 0.208 mmol), sodium acetate (0.57 mg, 0.694 mmol), and tris-2 methoxy phenyl phosphine (122 mg, 0.347 mmol), in DMF (3 ml) was microwaved at 130° C. for 1 hour. The mixture was filtered through a plug of celite, washing with water and ethyl acetate. The layers were separated, then the aqueous layer was washed with 3×30 mL EtOAc. The combine organic layers were washed with brine, then dried over sodium sulfate, filtered and concentrated in vacuo. The oily residue was purified on a 40 g redisep column, eluting with ethyl acetate:hexanes, 0:100 to 50:50. The desired fractions were concentrated in vacuo to yield the title compound. MS: m/z=785 (M+1).

Step B. 5-{(1E)-3-[(8R)-8-(3,5-difluorophenyl)-8-methyl-10-oxo-6,9-diazaspiro[4.5]dec-9-yl]prop-1-en-1-yl}-1,3-dihydrospiro[indene-2,3'-pyrrolo[2,3-b]pyridin]-2'(1'H)-one tert-Butyl (8R)-8-(3,5-difluorophenyl)-8-methyl-10-oxo-9-[(2E)-3-(2'-oxo-1'-{[2-(trimethylsilyl)ethoxy]methyl}-1,1',2',3-tetrahydrospiro[indene-2,3'-pyrrolo[2,3-b]pyridin]-5-yl)prop-2-en-1-yl]-6,9-diazaspiro[4.5]decane-6-carboxylate from Step A above (0.2276 g, 0.290 mmol) was dissolved in DCM (5 mL). To this solution was added 1 mL of TFA. The reaction was stirred for 24 hours, then concentrated in vacuo. The residue was dissolved in MeOH (5 mL) and to this solution was added 1N NaOH (2.90 ml, 2.90 mmol), and ethylenediamine (0.078 ml, 1.160 mmol). The reaction was stirred for ½ hour at RT, then concentrated in vacuo. The residue was partitioned between ethyl acetate and water. The layers were separated, then the aqueous layer was washed 3×20 mL with ethyl acetate. The combined organic layers were washed with brine. Dried over Magnesium sulfate, filtered and concentrated in vacuo to yield the title compound. Diastereomer separation was accomplished using a Chiralcel OJ column, eluting with $CO_2$:MeOH—70:30. Two peaks were isolated. Peak 1 MS: m/z=555 (M+1) HRMS: m/z=555.2569 (M+1); calculated m/z=555.2566 (M+1) for $C_{33}H_{32}F_2N_4O_2$, and Peak 2 MS: m/z=555 (M+1)HRMS: m/z=555.2569 (M+1); calculated m/z=555.2566 (M+1) for $C_{33}H_{33}F_2N_4O_2$.

Example 2

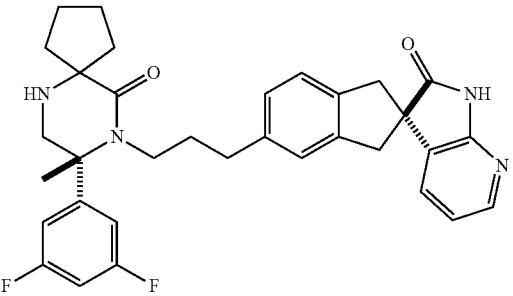

(2R)-5-{3-[(8R)-8-(3,5-difluorophenyl)-8-methyl-10-oxo-6,9-diazaspiro[4.5]dec-9-yl]propyl}-1,3-dihydrospiro[indene-2,3'-pyrrolo[2,3-b]pyridin]-2'(1'H)-one 5-{(1E)-3-[(8R)-8-(3,5-difluorophenyl)-8-methyl-10-oxo-6,9-diazaspiro[4.5]dec-9-yl]prop-1-en-1-yl}-1,3-dihydrospiro[indene-2,3'-pyrrolo[2,3-b]pyridin]-2'(1'H)-one (the first eluting peak of Example 1) (32 mg, 0.058 mmol) was dissolved in 1 mL of methanol and hydrogenated using an H-Cube apparatus and 10% Palladium on carbon cartridge while eluting with 10% acetic acid in methanol. The reaction was concentrated in vacuo and partitioned between ethyl acetate and 10% sodium bicarbonate. The layers were separated. The organic layer was washed with brine, dried over sodium sulfate, filtered and conc in vacuo to yield the title compound MS: m/z=557 (M+1), HRMS: m/z=557.2713 (M+1); calculated m/z=557.2723 (M+1) for $C_{33}H_{35}F_2N_4O_2$.

Example 3

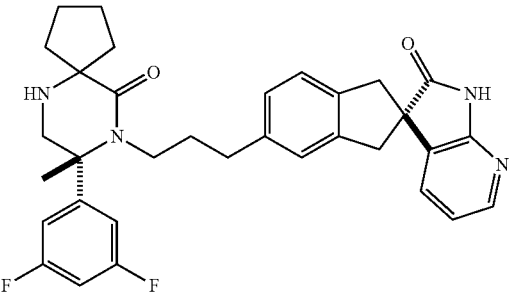

(2S)-5-{3-[(8R)-8-(3,5-difluorophenyl)-8-methyl-10-oxo-6,9-diazaspiro[4.5]dec-9-yl]propyl}-1,3-dihydrospiro[indene-2,3'-pyrrolo[2,3-b]pyridin]-2'(1'H)-one Hydrogenation of Peak 2 from Example 1 yields (2R)-5-{3-[(8S)-8-(3,5-difluorophenyl)-8-methyl-10-oxo-6,9-diazaspiro[4.5]dec-9-yl]propyl}-1,3-dihydrospiro[indene-2,3'-pyrrolo[2,3-b]pyridin]-2'(1'H)-one. MS: m/z=557 (M+1). HRMS: m/z=557.2722 (M+1); calculated m/z=557.2723 (M+1) for $C_{33}H_{35}F_2N_4O_2$.

Example 4

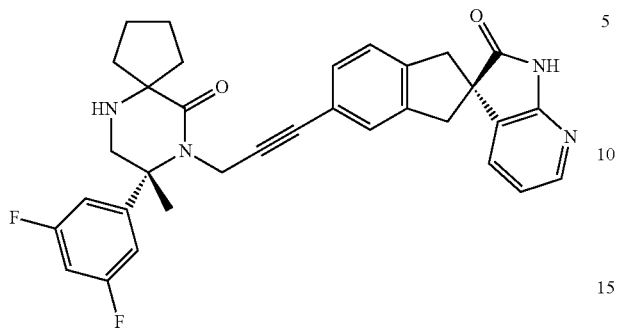

(2R)-5-{3-[(8R)-8-(3,5-Difluorophenyl)-8-methyl-10-oxo-6,9-diazaspiro[4.5]dec-9-yl]prop-1-yn-1-yl}-1,3-dihydrospiro[indene-2,3'-pyrrolo[2,3-b]pyridin]-2'(1'H)-one Step A. (8R)-8-(3,5-Difluorophenyl)-8-methyl-9-prop-2-yn-1-yl-6,9-diazaspiro[4.5]decan-10-one Sodium hydride (86.0 mg, 2.15 mmol, 60% dispersion in mineral oil) was added to a solution of (8R)-8-(3,5-difluorophenyl)-8-methyl-6,9-diazaspiro[4.5]decan-10-one (502 mg, 1.791 mmol, described in Intermediate 1) in 5 ml of DMF. When the gas evolution had ceased, propargyl bromide (320 mg, 2.15 mmol, 80 wt % in toluene) was added to the solution at ambient temperature. After 16 hours, the reaction was quenched with water (20 mL) and extracted with $CH_2Cl_2$ (3×20 ml). The combined organic layers were dried over $Na_2SO_4$, filtered and concentrated in vacuo. The crude product was purified on silica gel, eluting with a gradient of $CH_2Cl_2$:ethyl acetate—98:2 to 50:50. The clean fractions were concentrated in vacuo to yield the title compound. MS: m/z=319 (M+1).

Step B. (2R)-5-{3-[(8R)-8-(3,5-Difluorophenyl)-8-methyl-10-oxo-6,9-diazaspiro[4.5]dec-9-yl]prop-1-yn-1-yl}-1,3-dihydrospiro[indene-2,3'-pyrrolo[2,3-b]pyridin]-2'(1'H)-one A suspension of (8R)-8-(3,5-difluorophenyl)-8-methyl-9-prop-2-yn-1-yl-6,9-diazaspiro[4.5]decan-10-one from Step A (25 mg, 0.079 mmol), (R)-5-bromo-1,3-dihydrospiro[indene-2,3'-pyrrolo[2,3-b]pyridin]-2'(1'H)-one (25 mg, 0.079 mmol described in intermediate 12 tetrakis(triphenylphosphine)palladium(0) (4.5 mg, 0.0039 mmol), copper(I)iodide (3.0 mg, 0.016 mmol), and triethylamine (0.022 mL, 0.16 mmol) in degassed DMF (0.5 ml) was heated at 80° C. for 16 hour. The mixture was filtered and purified directly by HPLC using a reversed phase C18 column and eluting with a gradient of $H_2O:CH_3CN:CF_3CO_2H$—90:10:0.1 to 5:95:0.1. The desired fractions were concentrated in vacuo to yield the title compound. MS: m/z=553 (M+1). HRMS: m/z=553.2400; calculated m/z=553.2410 for $C_{33}H_{31}F_2N_4O_2$.

Example 18

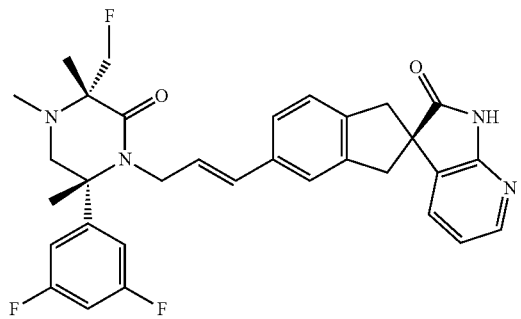 [SMILES: CN1C[C@@](C)(c2cc(F)cc(F)c2)N(C/C=C/c2ccc3c(c2)C[C@@]2(C3)C(=O)Nc3ncccc32)C(=O)[C@@]1(C)CF]

(2R)-5-{(1E)-3-[2-(3,5-Difluorophenyl)-5-(fluoromethyl)-2,4,5-trimethyl-6-oxopiperazin-1-yl]prop-1-en-1-yl}-1,3-dihydrospiro[indene-2,3'-pyrrolo[2,3-b]pyridin]-2'(1'H)-one A mixture of (2R)-5-bromo-1,3-dihydrospiro[indene-2,3'-indol]-2'(1'H)-one (8.8 mg), (±)-cis-6-(3,5-difluorophenyl)-3-(fluoromethyl)-3,4,6-trimethyl-1-(prop-2-en-1-yl)piperazin-2-one (10 mg, 0.03 mmol, described in Intermediate 18) and N,N-dicyclohexylmethylamine (7 µL, 0.03 mmol) in anhydrous degassed DMA (300 µL) in a microwave vessel was further degassed for 15 min by purging with argon. Bis(tri-t-butylphosphine)palladium(0) (19 mg, 0.04 mmol) was added and the sides of the vessel rinsed with additional anhydrous degassed DMA (100 µL). The vessel was then sealed and heated in a microwave reactor at 150° C. for 20 min. The mixture was then diluted with EtOAc and filtered. The filtrate was concentrated and the residue was purified by silica gel chromatography, eluting with a gradient of EtOAc: hexanes—0:100 to 100:0. The desired fractions were combined and concentrated in vacuo and this residue was further purified by HPLC using a reversed phase C18 column and eluting with a gradient of $H_2O:CH_3CN:CF_3CO_2H$—95:5:0.1 to 5:95:0.1. The desired fractions were concentrated in vacuo to yield the title compound. The desired fraction was concentrated in vacuo to give the trifluoroacetate salt of the title compound. MS: m/z=553 (M+1). HRMS: m/z=561.2480; calculated m/z=561.2472 for $C_{32}H_{32}F_3N_4O_2$.

Example 19

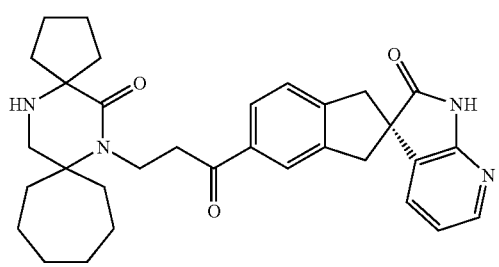 [SMILES: O=C(CCN1C(=O)C2(CCCC2)NCC12CCCCCC2)c1ccc2c(c1)C[C@@]1(C2)C(=O)Nc2ncccc21]

87

(2R)-5-[3-(16-oxo-6,15-diazadispiro[4.2.6.2]hexa-dec-15-yl)propanoyl]-1,3-dihydrospiro[indene-2,3'-pyrrolo[2,3-b]pyridin]-2'(1'H)-one Step A. tert-Butyl 16-oxo-15-{3-[(2R)-2'-oxo-1,1',2',3-tetrahydrospiro[indene-2,3'-pyrrolo[2,3-b]pyridin]-5-yl]prop-2-yn-1-yl}-6,15-diazadispiro[4.2.6.2]hexa-decane-6-carboxylate A stirred suspension of tert-butyl 16-oxo-15-prop-2-yn-1-yl-6,15-diazadispiro[4.2.6.2]hexadecane-6-carboxylate (110 mg, 0.294 mmol, described in Intermediate 23), (2R)-5-iodo-1,3-dihydrospiro[indene-2,3'-pyrrolo[2,3-b]pyridin]-2'(1'H)-one (106 mg, 0.294 mmol, described in Intermediate 27), tetrakis(triphenylphosphine)palladium(0) (34 mg, 0.029 mmol), copper(I)iodide (23 mg, 0.121 mmol), and triethylamine (0.082 mL, 0.588 mmol) in degassed DMF (1.5 mL) was heated at 50° C. for 30 min. The reaction was quenched with water (30 mL), partitioned with saturated $NaHCO_3$ solution (30 mL) and extracted with EtOAc (2×60 mL). The combined organic layers were dried over $Na_2SO_4$, filtered and concentrated in vacuo. The crude product was purified on silica gel, eluting with a gradient of $CH_2Cl_2$:MeOH—100:0 to 90:10, to yield the title compound. MS: m/z=609 (M+1).

Step B. (2R)-5-[3-(16-oxo-6,15-diazadispiro[4.2.6]hexadec-15-yl)propanoyl]-1,3-dihydrospiro[indene-2,3'-pyrrolo[2,3-b]pyridin]-2'(1'H)-one To a stirred solution of tert-butyl 16-oxo-15-{3-[(2R)-2'-oxo-1,1',2',3-tetrahydrospiro[indene-2,3'-pyrrolo[2,3-b]pyridin]-5-yl]prop-2-yn-1-yl}-6,15-diazadispiro[4.2.6.2]hexadecane-6-carboxylate from Step A (137 mg, 0.225 mmol) in EtOAc (15 mL) was bubbled HCl (g) for 1-2 min. The reaction mixture was stirred at ambient temperature for 16 h, then concentrated in vacuo and purified by HPLC using a reversed phase C18 column and eluting with a gradient of $H_2O$:$CH_3CN$:$CF_3CO_2H$—95:5:0.1 to 50:50:0.1. The desired fractions were combined, poured into saturated aqueous $NaHCO_3$ (30 mL), and extracted with EtOAc (60 mL). The combined organic extracts were dried over $Na_2SO_4$, filtered and concentrated in vacuo to yield the title compound. MS: m/z=527 (M+1).

Example 20

88

(2R)-5-({2-[(8R)-8-(3,5-Difluorophenyl)-8-methyl-10-oxo-6,9-diazaspiro[4.5]dec-9-yl]ethyl}sulfanyl)-1,3-dihydrospiro[indene-2,3'-pyrrolo[2,3-b]pyridin]-2'(1'H)-one Step A. (2R)-5-({2-[(8R)-8-(3,5-Difluorophenyl)-8-methyl-10-oxo-6,9-diazaspiro[4.5]dec-9-yl]ethyl}sulfanyl)-1'-{[2-(trimethylsilyl)ethoxy]methyl}-1,3-dihydrospiro[indene-2,3'-pyrrolo[2,3-b]pyridin]-2'(1'H)-one To a stirred solution of (8R)-8-(3,5-difluorophenyl)-9-(2-hydroxyethyl)-8-methyl-6,9-diazaspiro[4.5]decan-10-one (95 mg, 0.293 mmol, described in Intermediate 22) and (2R)-5-1'-{[2-(trimethylsilyl)ethoxy]methyl}-1,3-dihydrospiro[indene-2,3'-pyrrolo[2,3-b]pyridin]-2'(1'H)-one (108.7 mg, 0.273 mmol, described in Intermediate 24) in THF (5 mL) at 0° C. was added a mixture of di-tert-butyl azodicarboxylate (131 mg, 0.569 mmol) and tri-n-butylphosphine (0.135 mL, 0.547 mmol) in THF (2 mL). The reaction mixture was stirred for 2 h at ambient temperature, then partitioned between saturated aqueous $NaHCO_3$ (100 mL) and EtOAc (100 mL). The organic layer was dried over $Na_2SO_4$, filtered, and concentrated in vacuo. The crude product was purified on silica gel, eluting with a gradient of $CH_2Cl_2$:$CH_3OH$:$NH_4OH$—100:0:0 to 90:10:0.1, to provide the title compound. MS: m/z=705 (M+1).

Step B. (2R)-5-({2-[(8R)-8-(3,5-Difluorophenyl)-8-methyl-10-oxo-6,9-diazaspiro[4.5]dec-9-yl]ethyl}sulfanyl)-1,3-dihydrospiro[indene-2,3'-pyrrolo[2,3-b]pyridin]-2'(1'H)-one A solution of (2R)-5-({2-[(8R)-8-(3,5-difluorophenyl)-8-methyl-10-oxo-6,9-diazaspiro[4.5]dec-9-yl]ethyl}sulfanyl)-1'-{[2-(trimethylsilyl)ethoxy]methyl}-1,3-dihydrospiro[indene-2,3'-pyrrolo[2,3-b]pyridin]-2'(1'H)-one from Step A (69 mg, 0.098 mmol) in MeOH (10 mL) was saturated with HCl (g). After 1 h the mixture was resaturated with HCl (g), aged for 2 h, and then concentrated in vacuo. The residue was dissolved in MeOH (5 mL) and treated with ethylenediamine (0.033 mL, 0.489 mmol) to adjust the mixture to pH 10. After 2 h, the reaction mixture was concentrated in vacuo, and the crude product was purified on silica gel, eluting with a gradient of $CH_2Cl_2$:$CH_3OH$:$NH_4OH$—100:0:0 to 90:10:0.1, to yield the title compound. MS: m/z=575 (M+1). HRMS: m/z=575.2281; calculated m/z=575.2287 for $C_{32}H_{33}F_2N_4O_2S$.

Example 21

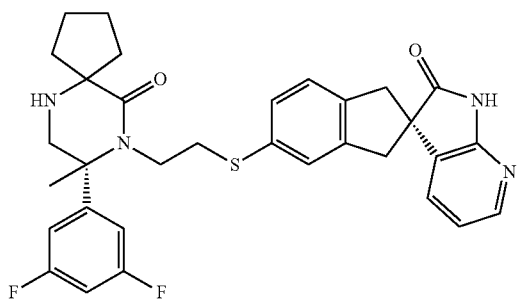 [SMILES: C[C@@]1(c2cc(F)cc(F)c2)CNC2(CCCC2)C(=O)N1CCSc1ccc2c(c1)C[C@@]1(C2)C(=O)Nc2ncccc21]

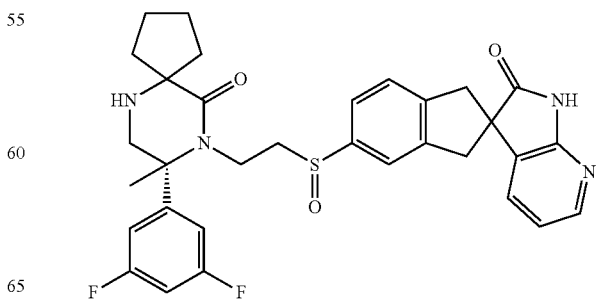

(2R)-5-({2-[(8R)-8-(3,5-Difluorophenyl)-8-methyl-10-oxo-6,9-diazaspiro[4.5]dec-9-yl]ethyl}sulfinyl)-1,3-dihydrospiro[indene-2,3'-pyrrolo[2,3-b]pyridin]-2'(1'H)-one To a stirred solution of (2R)-5-({2-[(8R)-8-(3,5-difluorophenyl)-8-methyl-10-oxo-6,9-diazaspiro[4.5] dec-9-yl]ethyl}sulfanyl)-1,3-dihydrospiro[indene-2,3'-pyrrolo[2,3-b]pyridin]-2'(1'H)-one (20.7 mg, 0.036 mmol, described in Example 20) in AcOH (0.50 mL) was added $H_2O_2$ (35% in $H_2O$, 0.018 mL, 0.206 mmol). After 3 h, the reaction was quenched with saturated $NaHCO_3$ solution (30 mL) and extracted with EtOAc (30 mL). The organic layer was dried over $Na_2SO_4$, filtered, and concentrated in vacuo. The crude product was purified on silica gel, eluting with a gradient of $CH_2Cl_2$:$CH_3OH$:$NH_4OH$—100:0:0 to 90:10:0.1, to afford the title compound. MS: m/z=591 (M+1). HRMS: m/z=591.2243; calculated m/z=591.2236 for $C_{32}H_{33}F_2N_4O_3S$.

Example 22

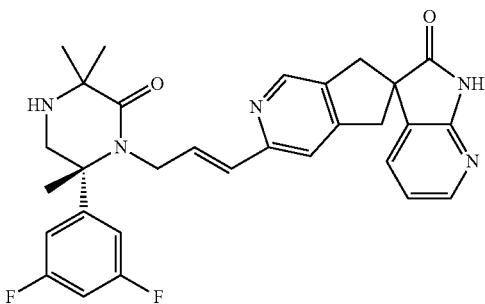 [SMILES: CC1(C)NC[C@@](C)(c2cc(F)cc(F)c2)N(C/C=C/c2cc3c(cn2)CC2(C3)C(=O)Nc3ncccc32)C1=O]

3-{(1E)-3-[(2R)-2-(3,5-Difluorophenyl)-2,5,5-trimethyl-6-oxopiperazin-1-yl]prop-1-en-1-yl}-5,7-dihydrospiro[cyclopenta[c]pyridine-6,3'-pyrrolo[2,3-b]pyridin]-2'(1'H)-one To a mixture of (±)-3-chloro-1'-{[2-(trimethylsilyl) ethoxy]methyl}-5,7-dihydrospiro[cyclopenta[c]pyridine-6,3'-pyrrolo[2,3-b]pyridin]-2'(1'H)-one (0.404 g, 1.004 mmol, described in Intermediate 32) and tert-butyl (5R)-4-allyl-5-(3,5-difluorophenyl)-2,2,5-trimethyl-3-oxopiperazine-1-carboxylate (0.36 g, 0.913 mmol) in degassed DMA (5.4 mL) in a large microwave vessel was added N,N-dicyclohexylmethylamine (0.215 mL, 1.00 mmol) and the mixture was degassed for 5 min. To the resulting mixture was added bis(tri-t-butylphosphine)palladium(0) (0.154 g, 0.301 mmol) and the mixture was degassed again. The reaction mixture was heated in a microwave reactor for 20 minutes at 150° C., cooled to ambient temperature, and filtered. The filtrate was partitioned between EtOAc (100 mL) and $H_2O$ (50 mL). The organic layer was dried over $Na_2SO_4$, filtered, and concentrated in vacuo. To the crude alkene in $CH_2Cl_2$ (10 mL) was added TFA (1.05 mL, 13.6 mmol) and the resulting mixture was stirred at room temperature for 30 min. The mixture was concentrated under reduced pressure, dissolved in MeOH and 1 N sodium hydroxide (2.73 mL, 2.73 mmol) and ethylenediamine (0.323 mL, 4.79 mmol) were added. The reaction mixture was stirred for 12 h at ambient temperature, concentrated in vacuo, and purified by HPLC using a reversed phase C18 column and eluting with a gradient of $H_2O$:$CH_3CN$:$CF_3CO_2H$—90:10:0.1 to 5:95:0.1, to give the title compound. MS: m/z=530 (M+1), HRMS: m/z=530.2360 (M+1); calculated m/z=530.2362 (M+1) for $C_{30}H_{30}F_2N_5O_2$.

Example 23

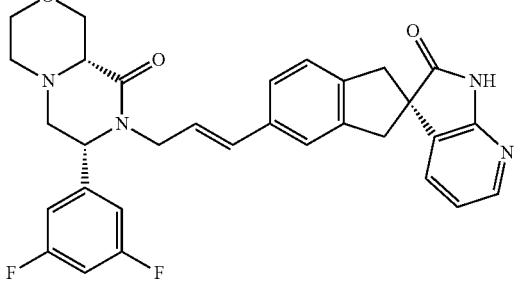

(2R)-5-{(1E)-3-[(7R,9aR)-7-(3,5-Difluorophenyl)-9-oxohexahydropyrazino[2,1-c][1,4]oxazin-8(1H)-yl] prop-1-en-1-yl}-1,3-dihydrospiro[indene-2,3'-pyrrolo[2,3-b]pyridin]-2'(1'H)-one To a mixture of (R)-5-bromo-1,3-dihydrospiro[indene-2,3'-pyrrolo[2,3-b]pyridin]-2'(1'H)-one (56 mg, 0.178 mmol, described in Intermediate 12) and (7R,9aR)-8-allyl-7-(3,5-difluorophenyl)hexahydropyrazino[2,1-c][1,4]oxazin-9 (6H)-one_(50 mg, 0.162 mmol, described in Intermediate 25) in degassed DMA (0.95 mL) in a microwave vessel was added N,N-dicyclohexylmethylamine (0.038 mL, 0.178 mmol). The mixture was degassed for 5 min, then bis(tri-t-butylphosphine)palladium(0) (27 mg, 0.054 mmol) was added and the mixture was degassed again. The reaction mixture was heated at 120° C. for 18 h, cooled to ambient temperature and partitioned between EtOAc and saturated aqueous $NaHCO_3$. The organic layer was dried over $Na_2SO_4$, filtered, concentrated in vacuo, and purified by HPLC using a reversed phase C18 column and eluting with a gradient of $H_2O$:$CH_3CN$:$CF_3CO_2H$—90:10:0.1 to 5:95:0.1, to give the title compound. MS: m/z=543 (M+1), HRMS: m/z=543.2207 (M+1); calculated m/z=543.2202 (M+1) for $C_{31}H_{28}F_2N_4O_3$.

Example 24

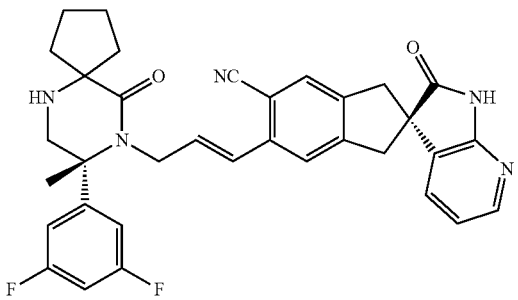 [SMILES: C[C@@]1(c2cc(F)cc(F)c2)CNC2(CCCC2)C(=O)N1C/C=C/c1cc2c(cc1C#N)C[C@]1(C2)C(=O)Nc2ncccc21]

(2S)-6-{(1E)-3-[(8R)-8-(3,5-Difluorophenyl)-8-methyl-10-oxo-6,9-diazaspiro[4.5]dec-9-yl]prop-1-en-1-yl}-2'-oxo-1,1',2',3-tetrahydrospiro[indene-2,3'-pyrrolo[2,3-b]pyridine]-5-carbonitrile To a mixture of (8R)-9-allyl-8-(3,5-difluorophenyl)-8-methyl-6,9-diazaspiro[4.5]decan-10-one (84 mg, 0.262 mmol), (2R)-6-bromo-2'-oxo-1,1',2',3-tetrahydrospiro[indene-2,3'-pyrrolo[2,3-b]pyridin]-5-carbonitrile (98 mg, 0.288 mmol, described in Intermediate 26) and N,N-dicyclohexylmethylamine (0.0612 mL, 0.288 mmol) in degassed DMA (1.7 mL) at ambient temperature was added bis(tri-t-butylphosphine) palladium (44.2 mg, 0.087 mmol). The reaction mixture was heated at 120° C. for 18 h, cooled, and filtered through a plug of Celite, washing with EtOAc. The filtrate was concentrated in vacuo and the residue was first purified by HPLC using reverse phase C18 column, eluting with a gradient of $H_2O$:$CH_3CN$:$CF_3CO_2H$—65:35:0.1 to 45:55:0.1, then with preparative thin layer chromatography, eluting with a gradient of EtOAc:hexanes—50:50 to 70:30, to give the title compound. MS: m/z=580 (M+1). HRMS: m/z=580.2542 (M+1); calculated m/z=580.2519 (M+1) for $C_{34}H_{31}F_2N_5O_2$.

Example 25

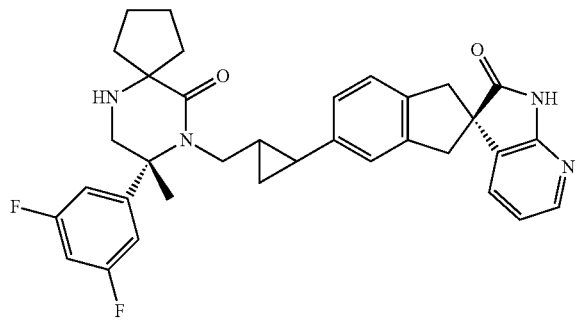 [SMILES: C[C@@]1(c2cc(F)cc(F)c2)CNC2(CCCC2)C(=O)N1CC1CC1c1ccc2c(c1)C[C@@]1(C2)C(=O)Nc2ncccc21]

(2R)-5-(2-{[(8R)-8-(3,5-Difluorophenyl)-8-methyl-10-oxo-6,9-diazaspiro[4.5]dec-9-yl]methyl}cyclopropyl)-1,3-dihydrospiro[indene-2,3'-pyrrolo[2,3-b]pyridin]-2'(1'H)-one To a solution of N-methyl-N'-nitro-N-nitrosoguanidine (47 mg, 0.32 mmol) in $Et_2O$ (1 mL) in a plastic vial was added 50% KOH until bubbling ceased. The solution was cooled to −78° C. for 15 min, and the top ether layer was decanted and added to a solution of ten-butyl (8R)-8-(3,5-difluorophenyl)-8-methyl-10-oxo-9-[(2E)-3-(2'-oxo-1'-{[2-(trimethylsilyl)ethoxy]methyl}-1,1',2',3-tetrahydrospiro[indene-2,3'-pyrrolo[2,3-b]pyridin]-5-yl)prop-2-en-1-yl]-6,9-diazaspiro[4.5]decane-6-carboxylate (25 mg, 0.032 mmol, described in Example 1) and palladium acetate (3.2 mg, 0.014 mmol) in $CH_2Cl_2$ (1 mL). The reaction mixture was stirred for 18 h at ambient temperature, then TFA (2 mL) was added and stirring was continued for 30 min. The mixture was concentrated in vacuo and the residue was dissolved in MeOH (1 mL) and treated with ethylenediamine (4.3 μL, 0.064 mmol) and 10 N NaOH (22 μL, 0.22 mmol) to adjust the mixture to pH 10. After 30 min, the mixture was filtered, diluted with DMSO (2 mL) and purified directly by HPLC using a reversed phase C18 column and eluting with a gradient of $H_2O$:$CH_3CN$:$CF_3CO_2H$—90:10:0.1 to 5:95:0.1. The desired fractions were concentrated in vacuo to yield the title compound as the trifluoroacetate salt. MS: m/z=569 (M+1). HRMS: m/z=569.2706 (M+1); calculated m/z=569.2723 (M+1) for $C_{34}H_{36}F_2N_4O_2$.

Example 26

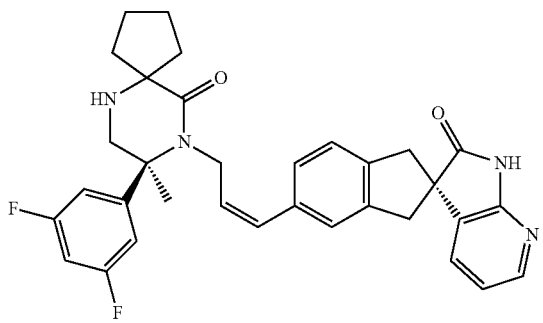 [SMILES: C[C@]1(c2cc(F)cc(F)c2)CNC2(CCCC2)C(=O)N1C/C=C\c1ccc2c(c1)C[C@@]1(C2)C(=O)Nc2ncccc21]

(2R)-5-{(1Z)-3-[(8S)-8-(3,5-Difluorophenyl)-8-methyl-10-oxo-6,9-diazaspiro[4.5]dec-9-yl]prop-1-en-1-yl}-1,3-dihydrospiro[indene-2,3'-pyrrolo[2,3-b]pyridin]-2'(1'H)-one A degassed solution of (2R)-5-{3-[(8R)-8-(3,5-difluorophenyl)-8-methyl-10-oxo-6,9-diazaspiro[4.5]dec-9-yl]prop-1-yn-1-yl}-1,3-dihydrospiro[indene-2,3'-b]pyridin]-2'(1'H)-one (18 mg, 0.033 mmol, described in Example 4) and Lindlar catalyst (14 mg) in MeOH (1 mL) was stirred under an atmosphere of hydrogen (ca. 1 atm) for 24 h. The reaction mixture was filtered through a Celite pad, diluted with DMSO (1 mL) and purified directly by HPLC using a reversed phase C18 column and eluting with a gradient of $H_2O$:$CH_3CN$:$CF_3CO_2H$—90:10:0.1 to 5:95:0.1. The desired fractions were concentrated in vacuo to yield the title compound as the trifluoroacetate salt. MS: m/z=555 (M+1). HRMS: m/z=555.2557 (M+1); calculated m/z=555.2566 (M+1) for $C_{33}H_{34}F_2N_4O_2$.

Example 27

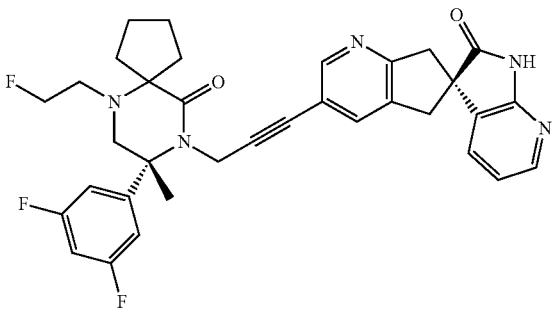 [SMILES: C[C@@]1(c2cc(F)cc(F)c2)CN(CCF)C2(CCCC2)C(=O)N1CC#Cc1cnc2c(c1)C[C@@]1(C2)C(=O)Nc2ncccc21]

(6S)-3-{3-[(8R)-8-(3,5-Difluorophenyl)-6-(2-fluoroethyl)-8-methyl-10-oxo-6,9-diazaspiro[4.5]dec-9-yl]prop-1-yn-1-yl}-5,7-dihydrospiro[cyclopenta[b]pyridine-6,3'-pyrrolo[2,3-b]pyridin]-2'(1'H)-one Step A. (6S)-3-{3-[(8R)-6-(2-Chloroethyl)-8-(3,5-difluorophenyl)-8-methyl-10-oxo-6,9-diazaspiro[4.5]dec-9-yl]prop-1-yn-1-yl}-5,7-dihydrospiro[cyclopenta[b]pyridine-6,3'-pyrrolo[2,3-b]pyridin]-2'(1'H)-one A solution of (6S)-3-{3-[(8R)-8-(3,5-difluorophenyl)-8-methyl-10-oxo-6,9-diazaspiro[4.5]dec-9-yl]prop-1-yn-1- yl}-5,7-dihydrospiro[cyclopenta[b]pyridine-6,3'-pyrrolo[2,3-b]pyridin]-2'(1'H)-one (100 mg, 0.18 mmol, described in Example 39), acetic acid (0.041 mL, 0.72 mmol), and chloroacetaldehyde (0.47 mL, 3.6 mmol, 50 wt % in H₂O) in MeOH (5 mL) was stirred for 5 min. Sodium cyanoborohydride (34 mg, 0.54 mmol) was added and stirring was continued for 42 h. Additional chloroacetaldehyde (0.47 mL, 3.6 mmol, 50 wt % in H₂O) and sodium cyanoborohydride (34 mg, 0.54 mmol) was added at 24 h. The reaction was quenched with saturated aqueous NaHCO₃ (10 mL) and extracted with CH₂Cl₂ (3×10 mL). The combined organic layers were dried over Na₂SO₄, filtered and concentrated in vacuo. The crude product was purified on silica gel, eluting with a gradient of CH₂Cl₂:MeOH:NH₄OH—100:0:0 to 90:10:1, to yield the title compound. MS: m/z=616 (M+1).

Step B. (6S)-3-{3-[(8R)-8-(3,5-Difluorophenyl)-6-(2-fluoroethyl)-8-methyl-10-oxo-6,9-diazaspiro[4.5]dec-9-yl]prop-1-yn-1-yl}-5,7-dihydrospiro[cyclopenta[b]pyridine-6,3'-pyrrolo[2,3-b]pyridin]-2'(1'H)-one A solution of (6S)-3-{3-[(8R)-6-(2-chloroethyl)-8-(3,5-difluorophenyl)-8-methyl-10-oxo-6,9-diazaspiro[4.5] dec-9-yl]prop-1-yn-1-yl}-5,7-dihydrospiro[cyclopenta[b]pyridine-6,3'-pyrrolo[2,3-b]pyridin]-2'(1'H)-one from Step A (67 mg, 0.11 mmol) and silver(I)fluoride (140 mg, 1.1 mmol) in acetonitrile (3 ml) was heated at 100° C. for 90 min The mixture was diluted with TFA (0.5 mL), filtered, and purified directly by HPLC using a reversed phase C18 column and eluting with a gradient of H₂O:CH₃CN:CF₃CO₂H—90:10:0.1 to 5:95:0.1. The desired fractions were poured onto saturated NaHCO₃ (10 mL) and extracted with CH₂Cl₂ (3×10 ml). The combined organic layers were dried over Na₂SO₄, filtered and concentrated in vacuo to yield the title compound. MS: m/z=600 (M+1). HRMS: m/z=600.2604 (M+1); calculated m/z=600.2581 (M+1) for C₃₄H₃₄F₃N₅O₂.

Example 28

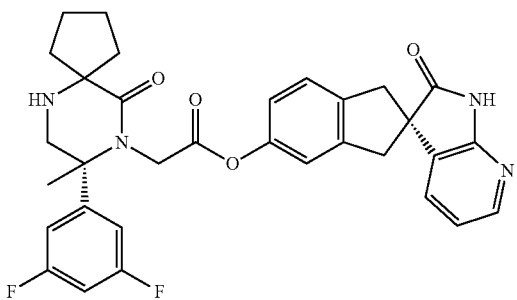 [SMILES: C[C@@]1(c2cc(F)cc(F)c2)CNC2(CCCC2)C(=O)N1CC(=O)Oc1ccc2c(c1)C[C@@]1(C2)C(=O)Nc2ncccc21]

(2R)-2'-Oxo-1,1',2',3-tetrahydrospiro[indene-2,3'-pyrrolo[2,3-b]pyridin]-5-yl[(8R)-8-(3,5-difluorophenyl)-8-methyl-10-oxo-6,9-diazaspiro[4.5]dec-9-yl]acetate Step A. tert-Butyl (8R)-8-(3,5-difluorophenyl)-8-methyl-10-oxo-9-[2-oxo-2-(pentafluorophenoxy)ethyl]-6,9-diazaspiro[4.5]decane-6-carboxylate To a stirred solution of [(8R)-6-(tert-butoxycarbonyl)-8-(3,5-difluorophenyl)-8-methyl-10-oxo-6,9-diazaspiro[4.5]dec-9-yl]acetic acid (254 mg, 0.579 mmol, described in Intermediate 21) in DMF (2 mL) was added pentafluorophenyl trifluoroacetate (0.7 mL, 4.07 mmol). The reaction mixture was stirred for 4 h at ambient temperature, then partitioned between saturated aqueous NaHCO₃ (30 mL) and EtOAc (50 mL). The organic layer was dried over Na₂SO₄, filtered, and concentrated in vacuo. The crude product was purified on silica gel, eluting with a gradient of hexanes:EtOAc—100:0 to 0:100, to provide the title compound.

Step B. tert-Butyl (8R)-8-(3,5-difluorophenyl)-8-methyl-10-oxo-9-(2-oxo-2-{[(2R)-2'-oxo-1'-{[2-(trimethylsilyl)ethoxy]methyl}-1,1',2',3-tetrahydrospiro[indene-2,3'-pyrrolo[2,3-b]pyridin]-5-yl]oxy}ethyl)-6,9-diazaspiro[4.5]decane-6-carboxylate A mixture of tert-butyl (8R)-8-(3,5-difluorophenyl)-8-methyl-10-oxo-9-[2-oxo-2-(pentafluorophenoxy)ethyl]-6,9-diazaspiro[4.5]decane-6-carboxylate from Step A (119 mg, 0.197 mmol), (2R)-5-hydroxy-1'-{[2-(trimethylsilyl)ethoxy]methyl}-1,3-dihydrospiro[indene-2,3'-pyrrolo[2,3-b]pyridin]-2'(1'H)-one (77 mg, 0.201 mmol, described in Intermediate 35), and N,N-diisopropylethylamine (0.17 mL, 0.98 mmol) in DMF (0.5 mL) was heated at 150° C. in a microwave reactor for 30 min. The reaction mixture was cooled and partitioned between saturated aqueous NaHCO₃ (20 mL) and EtOAc (30 mL). The organic layer was dried over Na₂SO₄, filtered, and concentrated in vacuo. The crude product was purified on silica gel, eluting with a gradient of hexanes:EtOAc—100:0 to 0:100, to provide the title compound. MS: m/z=803.7 (M+1).

Step C. (2R)-2'-Oxo-1,1',2',3-tetrahydrospiro[indene-2,3'-pyrrolo[2,3-b]pyridin]-5-yl[(8R)-8-[3,5-difluorophenyl)-8-methyl-10-oxo-6,9-diazaspiro[4.5]dec-9-yl]acetate To a solution of tert-butyl (8R)-8-(3,5-difluorophenyl)-8-methyl-10-oxo-9-(2-oxo-2-{[(2R)-2'-oxo-1'-{[2-(trimethylsilyl)ethoxy]methyl}-1,1',2',3-tetrahydrospiro[indene-2,3'-pyrrolo[2,3-b]pyridin]-5-yl]oxy}ethyl)-6,9-diazaspiro[4.5]decane-6-carboxylate from Step B (69 mg, 0.086 mmol), in CH₂Cl₂ (10 mL) was added TFA (1 mL). After 3 h, the reaction mixture was concentrated in vacuo and the residue was partitioned between saturated aqueous NaHCO₃ (20 mL) and EtOAc (30 mL) containing 1,2-ethylenediamine (0.2 mL). The organic layer was dried over Na₂SO₄, filtered, and concentrated in vacuo. The crude product was purified on silica gel, eluting with a gradient of CH₂Cl₂:MeOH—100:0 to 90:10, followed by HPLC using a reversed phase C18 column and eluting with a gradient of H₂O:CH₃CN:CF₃CO₂H—90:10:0.1 to 5:95:0.1, to afford the title compound. MS: m/z=573 (M+1). HRMS: m/z=573.2317 (M+1); calculated m/z=573.2308 (M+1) for C₃₁H₃₁F₂N₄O₄.

TABLE 2

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---|---|---|
| 5 | 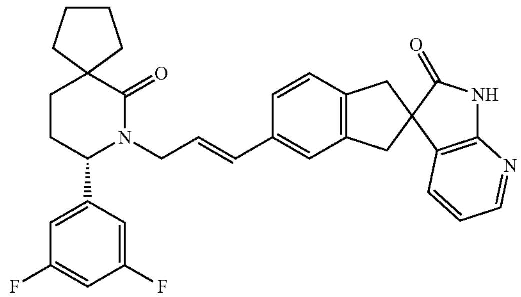 [SMILES: O=C1N(C/C=C/c2ccc3c(c2)CC2(C3)C(=O)Nc3ncccc32)[C@H](c2cc(F)cc(F)c2)CCC12CCCC2] | 540 |
| 6 | 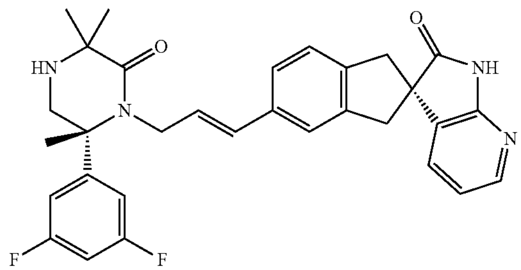 | 529 |
| 8 | 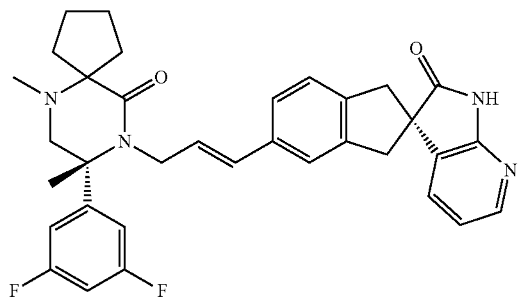 | 569 |
| 9 | 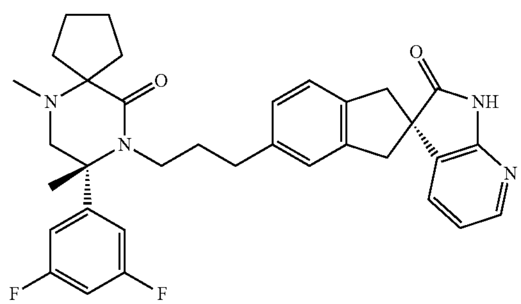 | 571 |
| 13 | 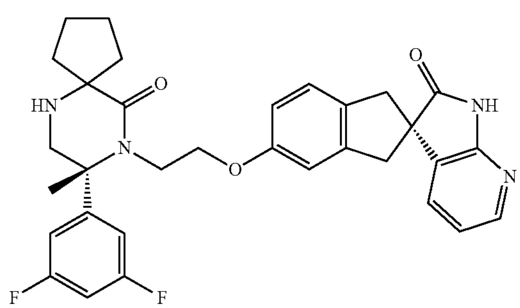 | 559 |

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---|---|---|
| 15 | 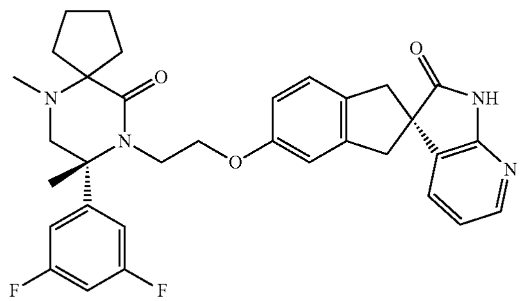 | 573 |
| 29 | 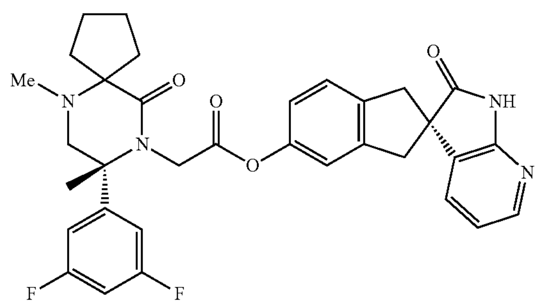 [SMILES: CN1C[C@@](C)(c2cc(F)cc(F)c2)N(CC(=O)Oc2ccc3c(c2)C[C@@]2(C3)C(=O)Nc3ncccc32)C(=O)C12CCCC2] | 587 |
| 30 | 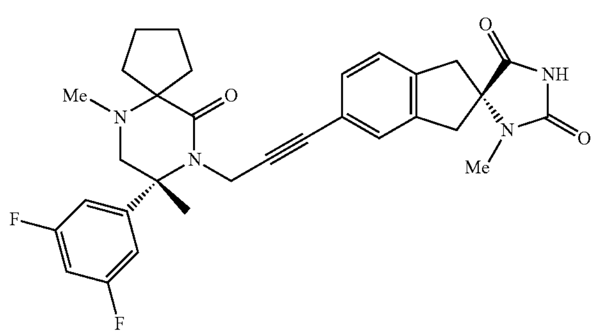 [SMILES: CN1C[C@@](C)(c2cc(F)cc(F)c2)N(CC#Cc2ccc3c(c2)C[C@@]2(C3)C(=O)NC(=O)N2C)C(=O)C12CCCC2] | 547 |
| 31 | 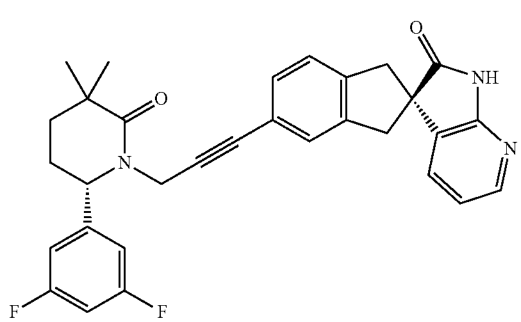 [SMILES: CC1(C)CC[C@@H](c2cc(F)cc(F)c2)N(CC#Cc2ccc3c(c2)C[C@@]2(C3)C(=O)Nc3ncccc32)C1=O] | 512 |

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---|---|---|
| 32 | 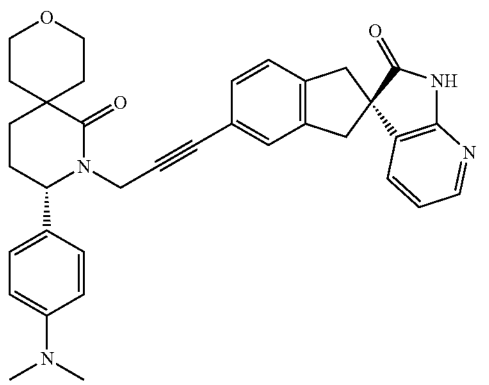 [SMILES: CN(C)c1ccc([C@@H]2CCC3(CCOCC3)C(=O)N2CC#Cc2ccc3c(c2)C[C@@]2(C3)C(=O)Nc3ncccc32)cc1] | 561 |
| 33 | | 527 |
| 33 | | 541 |
| 34 | 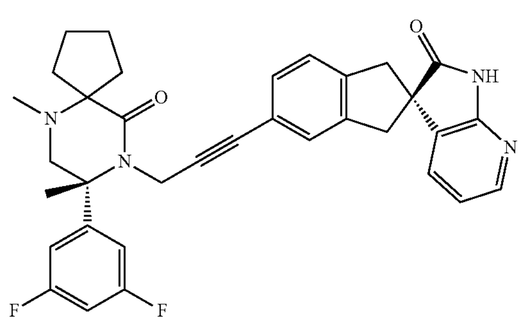 [SMILES: CN1C[C@@](C)(c2cc(F)cc(F)c2)N(CC#Cc2ccc3c(c2)C[C@@]2(C3)C(=O)Nc3ncccc32)C(=O)C12CCCC2] | 567 |

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---------|-----------|-----------------|
| 35 | 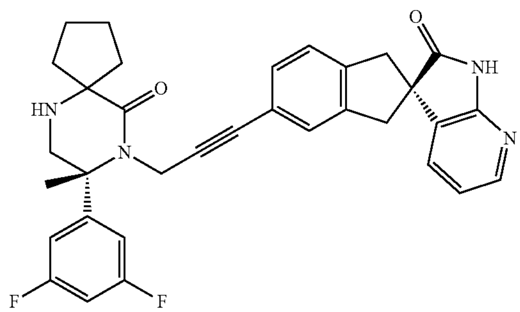 [SMILES: C[C@@]1(c2cc(F)cc(F)c2)CNC2(CCCC2)C(=O)N1CC#Cc1ccc2c(c1)C[C@@]1(C2)C(=O)Nc2ncccc21] | 553 |
| 36 | 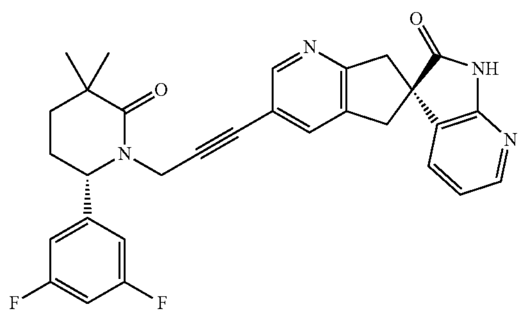 [SMILES: CC1(C)CC[C@@H](c2cc(F)cc(F)c2)N(CC#Cc2cnc3c(c2)C[C@@]2(C3)C(=O)Nc3ncccc32)C1=O] | 513 |
| 37 | 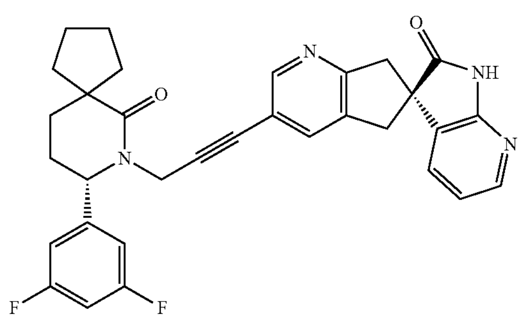 [SMILES: O=C1N(CC#Cc2cnc3c(c2)C[C@@]2(C3)C(=O)Nc3ncccc32)[C@H](c2cc(F)cc(F)c2)CCC12CCCC2] | 539 |
| 38 | 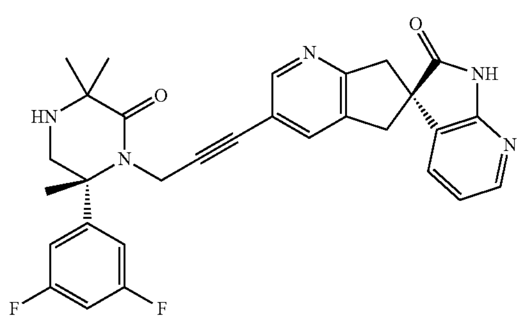 [SMILES: CC1(C)NC[C@@](C)(c2cc(F)cc(F)c2)N(CC#Cc2cnc3c(c2)C[C@@]2(C3)C(=O)Nc3ncccc32)C1=O] | 528 |

103

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---|---|---|
| 39 | 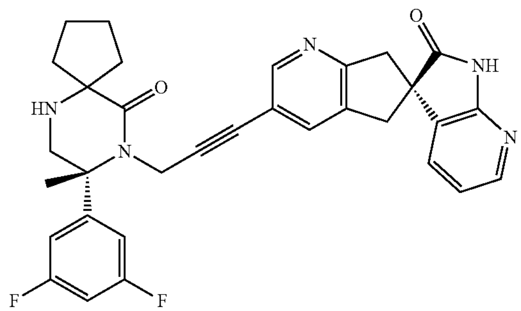 [SMILES: C[C@@]1(c2cc(F)cc(F)c2)CNC2(CCCC2)C(=O)N1CC#Cc1cnc2c(c1)C[C@@]1(C2)C(=O)Nc2ncccc21] | 554 |
| 40 | 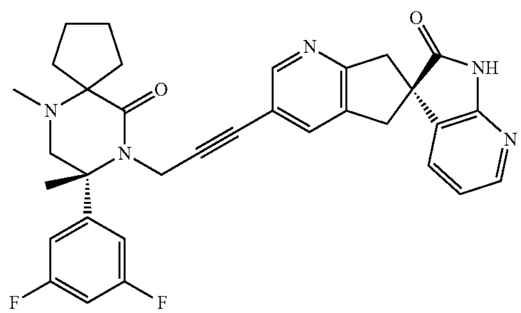 | 568 |
| 41 | 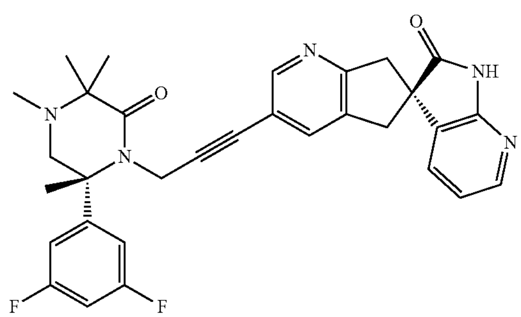 [SMILES: CN1C[C@@](C)(c2cc(F)cc(F)c2)N(CC#Cc2cnc3c(c2)C[C@@]2(C3)C(=O)Nc3ncccc32)C(=O)C1(C)C] | 542 |
| 42 | 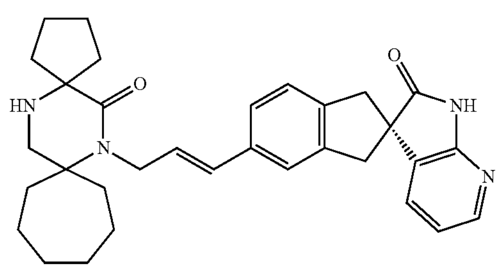 [SMILES: O=C1N(C/C=C/c2ccc3c(c2)C[C@@]2(C3)C(=O)Nc3ncccc32)C2(CCCCCC2)CNC12CCCC2] | 511 |
| 43 | 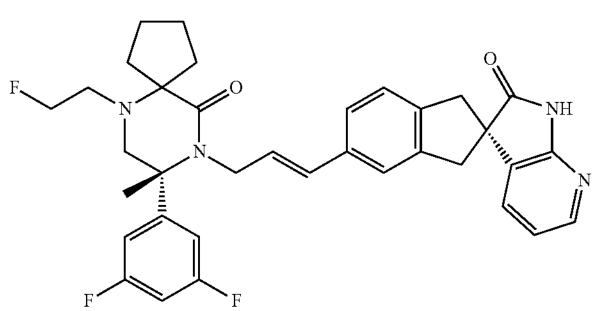 [SMILES: C[C@@]1(c2cc(F)cc(F)c2)CN(CCF)C2(CCCC2)C(=O)N1C/C=C/c1ccc2c(c1)C[C@@]1(C2)C(=O)Nc2ncccc21] | 601 |

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
| --- | --- | --- |
| 44 | 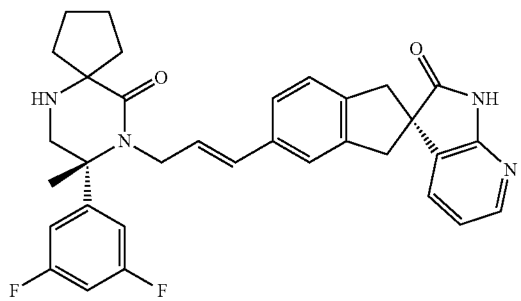 [SMILES: C[C@@]1(c2cc(F)cc(F)c2)CNC2(CCCC2)C(=O)N1C/C=C/c1ccc2c(c1)C[C@@]1(C2)C(=O)Nc2ncccc21] | 555 |
| 45 | 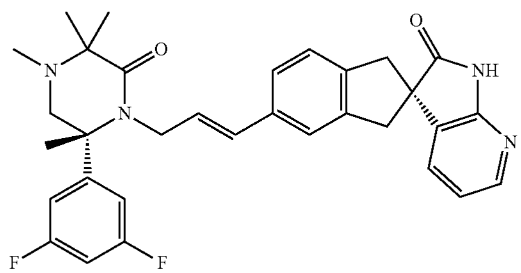 [SMILES: CN1C[C@@](C)(c2cc(F)cc(F)c2)N(C/C=C/c2ccc3c(c2)C[C@@]2(C3)C(=O)Nc3ncccc32)C(=O)C1(C)C] | 543 |
| 46 | 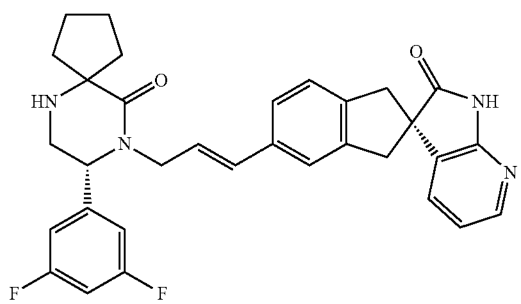 | 541 |
| 47 | 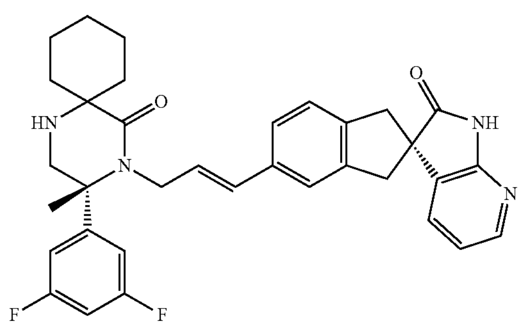 [SMILES: C[C@@]1(c2cc(F)cc(F)c2)CNC2(CCCCC2)C(=O)N1C/C=C/c1ccc2c(c1)C[C@@]1(C2)C(=O)Nc2ncccc21] | 569 |
| 48 | 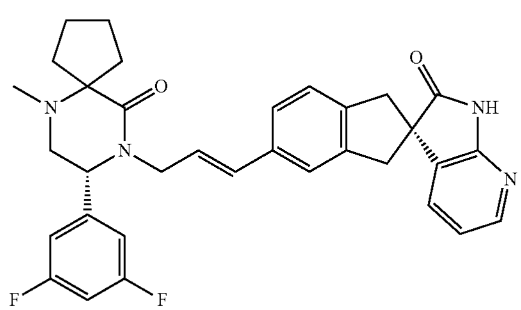 [SMILES: CN1C[C@@H](c2cc(F)cc(F)c2)N(C/C=C/c2ccc3c(c2)C[C@@]2(C3)C(=O)Nc3ncccc32)C(=O)C12CCCC2] | 555 |

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---|---|---|
| 49 | 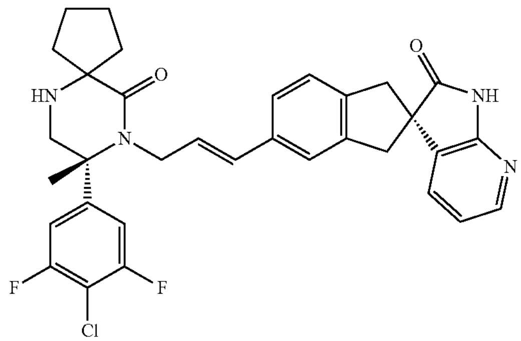 [SMILES: C[C@@]1(c2cc(F)c(Cl)c(F)c2)CNC2(CCCC2)C(=O)N1C/C=C/c1ccc2c(c1)C[C@@]1(C2)C(=O)Nc2ncccc21] | 589 |
| 50 | 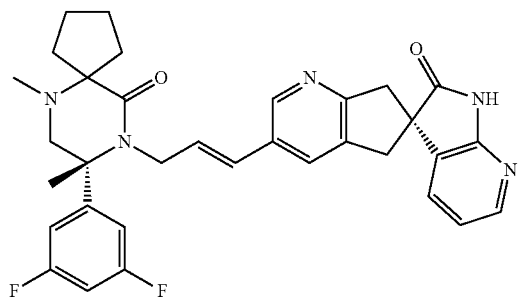 [SMILES: CN1C[C@@](C)(c2cc(F)cc(F)c2)N(C/C=C/c2cnc3c(c2)C[C@@]2(C3)C(=O)Nc3ncccc32)C(=O)C12CCCC2] | 570 |
| 51 | 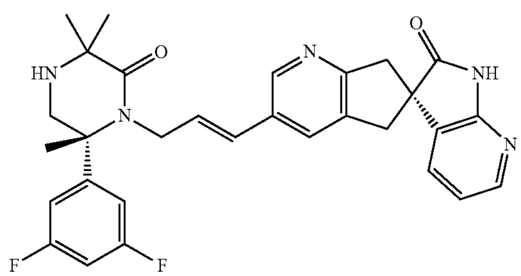 [SMILES: CC1(C)NC[C@@](C)(c2cc(F)cc(F)c2)N(C/C=C/c2cnc3c(c2)C[C@@]2(C3)C(=O)Nc3ncccc32)C1=O] | 530 |
| 52 | 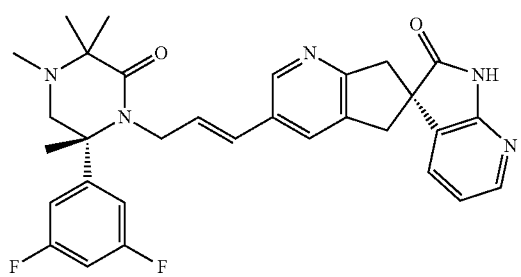 [SMILES: CN1C[C@@](C)(c2cc(F)cc(F)c2)N(C/C=C/c2cnc3c(c2)C[C@@]2(C3)C(=O)Nc3ncccc32)C(=O)C1(C)C] | 544 |
| 53 | 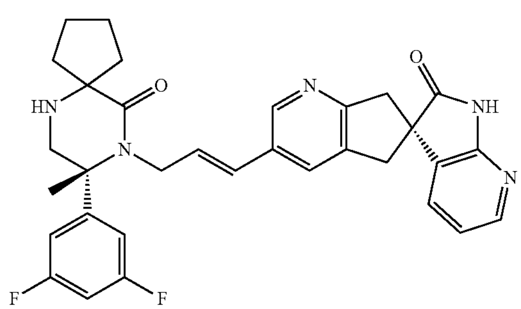 [SMILES: C[C@@]1(c2cc(F)cc(F)c2)CNC2(CCCC2)C(=O)N1C/C=C/c1cnc2c(c1)C[C@@]1(C2)C(=O)Nc2ncccc21] | 556 |

TABLE 2-continued

Essentially following the procedures outlined for the Examples above, the Examples shown in Table 2 were prepared. Requisite starting materials were commercially available, known in the literature, described herein, or readily synthesized by one skilled in the art of organic synthesis.

| Example | Structure | MS: m/z (M + 1) |
|---|---|---|
| 54 | 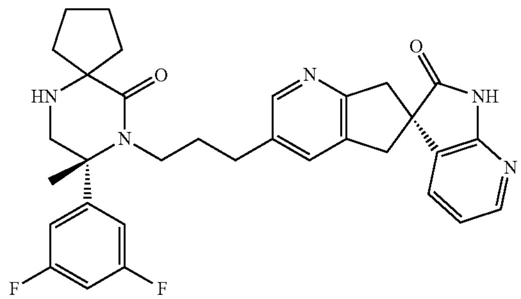 [SMILES: C[C@@]1(c2cc(F)cc(F)c2)CNC2(CCCC2)C(=O)N1CCCc1cnc2c(c1)C[C@@]1(C2)C(=O)Nc2ncccc21] | 558 |
| 55 | 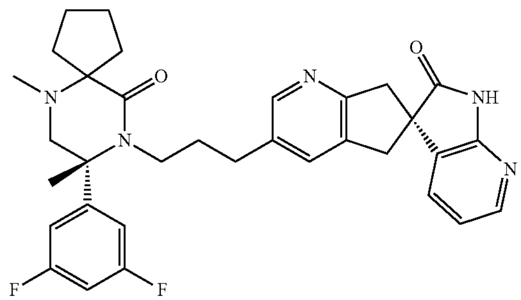 [SMILES: CN1C[C@@](C)(c2cc(F)cc(F)c2)N(CCCc2cnc3c(c2)C[C@@]2(C3)C(=O)Nc3ncccc32)C(=O)C12CCCC2] | 572 |

TABLE 3

Essentially following the procedures outlined for the Examples above, the Examples shown in Table 3 are prepared. Requisite starting materials are commercially available, known in the literature, described herein, or readily synthesized by one skilled in the art of organic synthesis.

| Example | Structure |
|---|---|
| 7 | 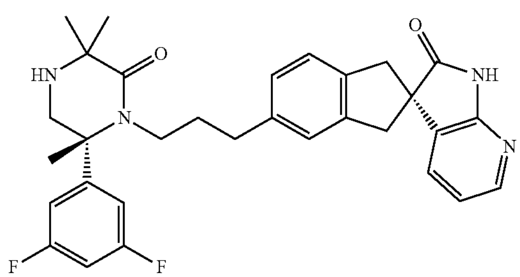 [SMILES: CC1(C)NC[C@@](C)(c2cc(F)cc(F)c2)N(CCCc2ccc3c(c2)C[C@@]2(C3)C(=O)Nc3ncccc32)C1=O] |
| 10 | 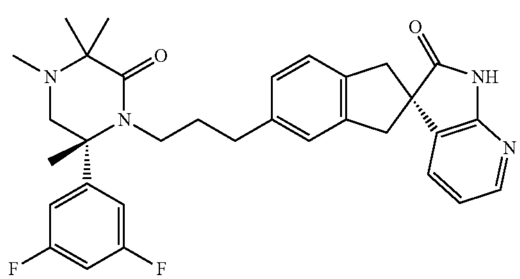 [SMILES: CN1C[C@@](C)(c2cc(F)cc(F)c2)N(CCCc2ccc3c(c2)C[C@@]2(C3)C(=O)Nc3ncccc32)C(=O)C1(C)C] |
| 11 | |
| 12 | |

TABLE 3-continued

Essentially following the procedures outlined for the Examples above, the Examples shown in Table 3 are prepared. Requisite starting materials are commercially available, known in the literature, described herein, or readily synthesized by one skilled in the art of organic synthesis.

| Example | Structure |
|---|---|
| 14 | 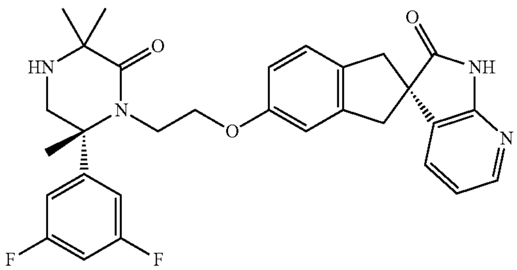 |
| 16 | 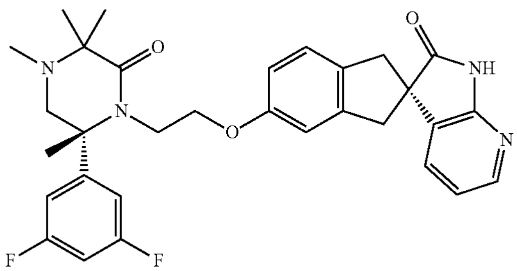 [SMILES: CN1C[C@@](C)(c2cc(F)cc(F)c2)N(CCOc2ccc3c(c2)C[C@@]2(C3)C(=O)Nc3ncccc32)C(=O)C1(C)C] |
| 17 | 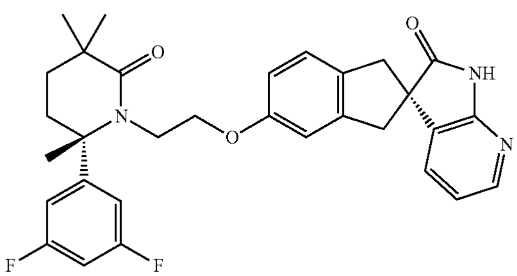 [SMILES: CC1(C)CC[C@@](C)(c2cc(F)cc(F)c2)N(CCOc2ccc3c(c2)C[C@@]2(C3)C(=O)Nc3ncccc32)C1=O] |

Although specific enantiomers and diastereomers appear in the above Examples and Intermediates, it is well understood by those skilled in the art that modifications to reaction conditions and reagents (for example, but not limited to: using the opposite chirality for starting materials; different catalysts; using the opposite chirality for reagents; choosing to use a different enantiomer or diastereomer subsequent to a chiral resolution) will provide alternative enantiomers and diastereomers, all of which are included in the spirit and scope of the invention. It is intended that all of the possible optical isomers and diastereomers in mixtures and as pure or partially purified compounds are included within the ambit of this invention. The present invention is meant to comprehend all such isomeric forms of these compounds.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound having the formula Id:

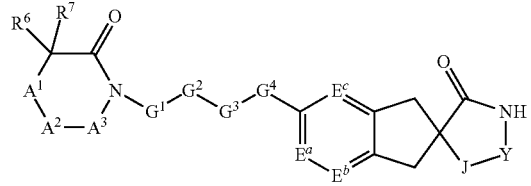

Id wherein $A^1$ is:
  (1) —$CR^6R^7$—, or
  (2) —$N(R^8)$—,
$A^2$ is:
  (1) —$CR^6R^7$—,
  (2) —$CR^{10}R^{11}$—, or
  (3) —(C=O)—;
$A^3$ is:
  (1) —$CR^6R^7$—,
  (2) —$N(R^8)$—,
  (3) —$CR^{10}R^{11}$—, or
  (4) —$N(R^{11})$—;
$E^a$ is:
  (1) —$C(R^{5a})$=,
  (2) —N=, or
  (3) —($N^+$—$O^-$)=;
$E^b$ is:
  (1) —$C(R^{5b})$=,
  (2) —N=, or
  (3) —($N^+$—$O^-$)=;
$E^c$ is:
  (1) —$C(R^{5c})$=,
  (2) —N=, or
  (3) —($N^+$—$O^-$)=;
$G^1$ is:
  (1) a bond,
  (2) —$CR^eR^f$—,
  (3) —$CR^eR^f$—$CH_2$—,
  (4) —$CH_2$—$CR^eR^f$—, or
  (5) —(C=O)—;
$G^2$ is:
  (1) a bond,
  (2) —$CR^eR^f$—,
  (3) —$CR^eR^f$—$CH_2$—,
  (4) —$CH_2$—$CR^eR^f$—,
  (5) —(C=O)—,
  (6) —$N(R^8)$—,
  (7) —O—,
  (8) —$S(O)_v$—,
  (9) —$SiR^gR^h$—,
  (10) —$C(R^i)$=$C(R^j)$—, or
  (11) —C≡C—;

$G^3$ is:
(1) —$CR^eR^f$—,
(2) —$N(R^8)$—,
(3) —O—,
(4) —$S(O)_v$—,
(5) —$SiR^gR^h$—,
(6) —(C=O)—,
(7) —$C(R^i)$=$C(R^j)$—, or
(8) —C≡C—,
and $G^3$ is not —(C=O)— if $G^4$ is —$N(R^8)$—;

$G^4$ is:
(1) —$CR^eR^f$—,
(2) —$N(R^8)$—,
(3) —O—,
(4) —$S(O)_v$—,
(5) —$SiR^gR^h$—,
(6) —(C=O)—,
(7) —$C(R^i)$=$C(R^j)$—, or
(8) —C≡C—;

$R^{5a}$, $R^{5b}$ and $R^{5c}$ are each independently selected from the group consisting of:
(1) hydrogen,
(2) —$C_{1-6}$alkyl, which is unsubstituted or substituted with 1-6 halo,
(3) halo,
(4) —$OR^a$, and
(5) —CN;

$R^6$ and $R^7$ are each independently selected from the group consisting of:
(1) hydrogen,
(2) —$C_{1-6}$alkyl, which is unsubstituted or substituted with 1-5 substituents each independently selected from the group consisting of:
 (a) halo,
 (b) —$OR^a$,
 (c) —$C_{3-6}$cycloalkyl,
 (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl, indolyl, indazolyl, benzimidazolyl, and oxazolyl, which phenyl or heterocycle is unsubstituted or substituted with 1-5 substituents each independently selected from the group consisting of:
  (i) halo,
  (ii) —$C_{1-6}$alkyl, which is unsubstituted or substituted with 1-5 halo,
  (iii) —$OR^a$,
  (iv) —$NR^bR^c$,
  (v) —CN, and
  (vi) oxo;
 (e) —$CO_2R^a$,
 (f) —C(=O)$NR^bR^c$,
 (g) —$S(O)_vR^d$,
 (h) —CN,
 (i) —$NR^bR^c$,
 (j) —N(Rb)C(=O)$R^a$,
 (k) —N(Rb)$SO_2R^d$,
 (l) —$CF_3$,
 (m) —O—$CO_2R^d$,
 (n) —O—(C=O)—$NR^bR^c$,
 (o) —$NR^b$—(C=O)—$NR^bR^c$, and
 (p) —C(=O)$R^a$,
(3) —$C_{3-8}$cycloalkyl, which is unsubstituted or substituted with 1-5 substituents each independently selected from the group consisting of:
 (a) halo,
 (b) —CN,
 (c) —$C_{1-4}$alkyl, which is unsubstituted or substituted with 1-3 halo, and
 (d) —$OR^a$,
(4) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from the group consisting of:
 (a) halo,
 (b) —$OR^a$,
 (c) —$C_{3-6}$ cycloalkyl,
 (d) phenyl, which is unsubstituted or substituted with 1-5 substituents each independently selected from the group consisting of:
  (i) halo,
  (ii) —$C_{1-6}$alkyl, which is unsubstituted or substituted with 1-6 halo, and
  (iii) —$OR^a$,
 (e) —$CO_2R^a$,
 (f) —C(=O)$NR^bR^c$,
 (g) —$S(O)_vR^d$,
 (h) —CN,
 (i) —$NR^bR^c$,
 (j) —N(Rb)C(=O)$R^a$,
 (k) —N($R^b$)$SO_2R^d$,
 (l) —O—$CO_2R^d$,
 (m) —O—(C=O) —$NR^bR^c$,
 (n) —$NR^b$—(C=O) —$NR^bR^c$,
 (o) —C(=O)$R^a$,
 (p) —$C_{1-6}$alkyl, which is unsubstituted or substituted with 1-6 halo, and
 (q) oxo;
(5) halo,
(6) —$OR^a$,
(7) —CN,
(8) —$CO_2R^a$,
(9) —N($R^b$)C(=O)$R^a$,
(10) —$NR^bR^c$,
(11) —C(=O)$NR^bR^c$, and
(12) —O(C=O)$R^a$;

or $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclononyl, cyclobutenyl, cyclopentenyl, cyclohexenyl, cycloheptenyl, cyclooctenyl, dioxolanyl, dioxanyl, aziridinyl, azetidinyl, pyrrolidinyl, piperidinyl, piperazinyl, morpholinyl, tetrahydrofuranyl, tetrahydropyranyl, tetrahydrothiapyranyl, oxetanyl, thietanyl and tetrahydrothienyl, wherein the sulfur is optionally oxidized to the sulfone or sulfoxide, which ring is unsubstituted or substituted with 1-5 substituents each independently selected from the group consisting of:
(a) —$C_{1-6}$alkyl, which is unsubstituted or substituted with 1-3 substituents each independently selected from the group consisting of:
 (i) halo,
 (ii) —$OR^a$,
 (iii) —$C_{3-6}$cycloalkyl,
 (iv) —$CO_2R^a$,
 (v) —$NR^bR^c$,
 (vi) —$S(O)_vR^d$,
 (vii) —C(=O)$NR^bR^c$, and
 (viii) phenyl, (b) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from the group consisting of:
  (i) halo,
  (ii) —$OR^a$,
  (iii) —$C_{3-6}$cycloalkyl,
  (iv) —$CO_2R^a$,
  (v) —$NR^bR^c$,
  (vi) —$S(O)_vR^d$,
  (vii) —$C(=O)NR^bR^c$, and
  (viii) phenyl,
(c) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, imidazolyl, furanyl, tetrahydrofuranyl, thiazolyl and oxazolyl, wherein the phenyl or heterocycle is optionally fused to the ring, and which phenyl or heterocycle is unsubstituted or substituted with 1-5 substituents each independently selected from the group consisting of:
  (i) halo,
  (ii) —$C_{1-6}$alkyl, which is unsubstituted or substituted with 1-5 halo,
  (iii) —$OR^a$,
  (iv) —$CO_2R^a$,
  (v) —$O(C=O)R^a$,
  (vi) —CN,
  (vii) —$NR^bR^c$,
  (viii) oxo,
  (ix) —$C(=O)NR^bR^c$,
  (x) —$N(Rb)C(=O)R^a$,
  (xi) —$N(R^b)CO_2R^a$,
  (xii) —$O(C=O)NR^bR^c$, and
  (xiii) —$S(O)_vR^d$,
(d) —$OR^a$,
(e) —$CO_2R^a$,
(f) —$C(=O)NR^bR^c$,
(g) —$S(O)_vR^d$,
(h) —CN,
(i) halo,
(j) —$NR^bR^c$,
(k) —$N(R^b)C(=O)R^a$,
(l) —$N(Rb)SO_2R^d$,
(m) —$O$—$CO_2R^d$,
(n) —$O$—$(C=O)$—$NR^bR^c$,
(o) —$NR^b$—$(C=O)$—$NR^bR^c$,
(p) —$C(=O)R^a$, and
(q) oxo;

$R^8$ is selected from the group consisting of:
(1) hydrogen,
(2) —$C(=O)R^a$,
(3) —$CO_2R^a$,
(4) —$S(=O)R^d$,
(5) —$SO_2R^d$,
(6) —$C(=O)NR^bR^c$,
(7) —$C_{1-6}$alkyl, which is unsubstituted or substituted with 1-5 substituents each independently selected from the group consisting of:
  (a) halo,
  (b) —$OR^a$,
  (c) —$C_{3-6}$cycloalkyl,
  (d) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from the group consisting of:
    (i) halo,
    (ii) —$C_{1-6}$alkyl, which is unsubstituted or substituted with 1-5 halo, and
    (iii) —$OR^a$,
    (iv) —$NR^bR^c$,
    (v) —$C(=O)R^a$,
    (vi) —$CO_2R^a$, and
    (vii) oxo,
  (e) —$CO_2R^a$,
  (f) —$C(=O)NR^bR^c$,
  (g) —$S(O)_vR^d$,
  (h) —CN,
  (i) —$NR^bR^c$,
  (j) —$N(Rb)C(=O)R^a$,
  (k) —$N(Rb)SO_2R^d$,
  (l) —$CF_3$,
  (m) —$O$—$CO_2R^d$,
  (n) —$O$—$(C=O)$—$NR^bR^c$,
  (o) —$NR^b$—$(C=O)$—$NR^bR^c$, and
  (p) —$C(=O)R^a$,
(8) —$C_{3-6}$cycloalkyl, which is unsubstituted or substituted with 1-6 substituents each independently selected from the group consisting of:
  (a) halo,
  (b) —CN,
  (c) —$OR^a$, and
  (d) $C_{1-6}$alkyl, which is unsubstituted or substituted with 1-6 halo;
or $R^7$ and $R^8$ and the atoms to which they are attached join to form a 4-, 5-, 6- or 7-membered alkyl- or heteroalkyl-ring optionally containing an additional heteroatom selected from N, O, and S, wherein the sulfur is optionally oxidized to the sulfone or sulfoxide, which ring is unsubstituted or substituted with 1-4 substituents each independently selected from the group consisting of:
  (a) halo,
  (b) phenyl, which is unsubstituted or substituted with 1-3 substituents each independently selected from the group consisting of: halo, $OR^a$, CN, and —$C(=O)OR^a$,
  (c) —$OR^a$, and
  (d) —$C_{1-6}$alkyl, which is unsubstituted or substituted with 1-6 halo;

$R^{10}$ is selected from the group consisting of:
(1) hydrogen,
(2) —$C_{1-6}$alkyl, which is unsubstituted or substituted with 1-5 substituents each independently selected from the group consisting of:
  (a) halo,
  (b) —$OR^a$,
  (c) —CN,
  (d) phenyl, and
  (e) —$C_{3-6}$cycloalkyl, which is unsubstituted or substituted with 1-6 halo,
(3) —$C_{3-6}$cycloalkyl, which is unsubstituted or substituted with 1-6 halo;

$R^{11}$ is selected from the group consisting of:
phenyl, naphthyl, tetrahydronaphthyl, indanyl, biphenyl, phenanthryl, anthryl, azepinyl, azepanyl, azetidinyl, benzimidazolyl, benzisoxazolyl, benzofuranyl, benzofurazanyl, benzopyranyl, benzothiopyranyl, benzofuryl, 1,3-benzodioxolyl, benzothiazolyl, benzothienyl, benzoxazolyl, benzopyrazolyl, benzotriazolyl, chromanyl, cinnolinyl, dibenzofuranyl, dihydrobenzofuryl, dihydrobenzothienyl, dihydrobenzothiopyranyl, dihydrobenzothiopyranyl sulfone, furyl, furanyl, imidazolidinyl, imidazolinyl, imidazolyl, indolinyl, indolyl, isochromanyl, isoindolinyl, isoquinolinyl, isothiazolidinyl, isothiazolyl, morpholinyl, naphthyridinyl, oxadiazolyl, 2-oxoazepinyl, 4-oxonaphthyridinyl, 2-oxopiperazinyl, 2-oxopiperidinyl, 2-oxopyrrolidinyl, 2-oxopyridyl, 2-oxoquinolinyl, piperidyl, piperazinyl, pyrazinyl, pyrazolidinyl, pyrazolyl, pyridazinyl, pyridinyl, pyridyl, pyrimidinyl, pyrimidyl, pyrrolidinyl, pyrrolyl, quinazolinyl, quinolinyl, quinoxalinyl, tetrahydrofuranyl, tetrahydrofuryl, tetrahydroimidazopyridinyl, tetrahydroisoquinolinyl, tetrahydroquinolinyl, tetrazolyl, thiamorpholinyl, thiamorpholinyl sulfoxide, thiamorpholinyl sulfone, thiazolyl, thiazolinyl, thienofuryl, thienothienyl, thienyl, triazolyl, isoxazolyl, tetrahydrothienyl, tetrahydropyranyl, oxetanyl, tetrahydrothiapyranyl, and thietanyl, where $R^{11}$ is unsubstituted or substituted with 1-5 substituents each independently selected from $R^{12}$, $R^{13}$, $R^{14}$, $R^{15a}$ and $R^{15b}$;

$R^{12}$, $R^{13}$, $R^{14}$, $R^{15a}$ and $R^{15b}$ are each independently selected from the group consisting of:
(1) —$C_{1-6}$alkyl, which is unsubstituted or substituted with 1-5 substituents each independently selected from the group consisting of:
  (a) halo,
  (b) —$OR^a$,
  (c) —$C_{3-6}$cycloalkyl,
  (d) phenyl or heterocycle, wherein said heterocycle is selected from the group consisting of: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from the group consisting of:
    (i) halo,
    (ii) —$C_{1-6}$alkyl, which is unsubstituted or substituted with 1-5 halo, and
    (iii) —$OR^a$,
  (e) —$CO_2R^a$,
  (f) —$C(=O)NR^bR^c$,
  (g) —$S(O)_vR^d$,
  (h) —CN,
  (i) —$NR^bR^c$,
  (j) —N(Rb)C(=O)$R^a$,
  (k) —N(Rb)$SO_2R^d$,
  (l) —$CF_3$,
  (m) —O—$CO_2R^d$,
  (n) —O—(C=O)—$NR^bR^c$,
  (o) —$NR^b$—(C=O)—$NR^bR^c$, and
  (p) —C(=O)$R^a$,
(2) —$C_{3-6}$cycloalkyl, which is unsubstituted or substituted with 1-5 substituents each independently selected from the group consisting of:
  (a) halo,
  (b) —CN,
  (c) —$C_{1-6}$alkyl, which is unsubstituted or substituted with 1-5 halo,
  (d) —$OR^a$, and
  (e) phenyl, which is unsubstituted or substituted with 1-5 substituents where the substituents are each independently selected from the group consisting of:
    (i) —$OR^a$,
    (ii) halo,
    (iii) —CN, and
    (iv) —$C_{1-6}$alkyl, which is unsubstituted or substituted with 1-5 halo,
(3) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from the group consisting of:
  (a) halo,
  (b) —$OR^a$,
  (c) —$C_{3-6}$cycloalkyl,
  (d) phenyl, which is unsubstituted or substituted with 1-5 substituents each independently selected from the group consisting of:
    (i) halo,
    (ii) —$C_{1-6}$alkyl, which is unsubstituted or substituted with 1-6 halo, and
    (iii) —$OR^a$,
  (e) —$CO_2R^a$,
  (f) —C(=O)$NR^bR^c$,
  (g) —$S(O)_vR^d$,
  (h) —CN,
  (i) —$NR^bR^c$,
  (j) —N(Rb)C(=O)$R^a$,
  (k) —N(Rb)$SO_2R^d$,
  (l) —O—$CO_2R^d$,
  (m) —O—(C=O)—$NR^bR^c$,
  (n) —$NR^b$—(C=O)—$NR^bR^c$,
  (o) —C(=O)$R^a$, and
  (p) —$C_{1-6}$alkyl, which is unsubstituted or substituted with 1-6 halo,
(4) halo,
(5) oxo
(6) —$OR^a$,
(7) —CN,
(8) —$CO_2R^a$,
(9) —C(=O)$R^a$,
(10) —$NR^bR^c$,
(11) —$S(O)_vR^d$,
(12) —C(=O)$NR^bR^c$,
(13) —O—$CO_2R^d$,
(14) —N(Rb)$CO_7R^d$,
(15) —O—(C=O)—$NR^bR^c$,
(16) —$NR^b$—(C=O)—$NR^bR^c$,
(17) —$SO_2NR^bR^c$,
(18) —N(Rb)$SO_2R^d$,
or $R^{15a}$ and $R^{15b}$ and the atom(s) to which they are attached join to form a ring selected from cyclopropyl, cyclobutyl, cyclopentyl, cyclohexyl, cycloheptyl, aziridinyl, azetidinyl, pyrrolidinyl, piperidinyl, piperazinyl, morpholinyl, thietanyl and tetrahydrothienyl, wherein the sulfur is optionally oxidized to the sulfone or sulfoxide, which ring is unsubstituted or substituted with 1-5 substituents each independently selected from the group consisting of:
  (a) —$C_{1-6}$alkyl, which is unsubstituted or substituted with 1-3 substituents each independently selected from the group consisting of:
    (i) halo,
    (ii) —$OR^a$,
    (iii) —$C_{3-6}$cycloalkyl,
    (iv) —$CO_2R^a$,
    (v) —$NR^bR^c$, (vi) —S(O)$_v$R$^d$,
(vii) —C(=O)NR$^b$R$^c$, and
(viii) phenyl,
(b) phenyl or heterocycle, wherein said heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, which phenyl or heterocycle is unsubstituted or substituted with 1-5 substituents each independently selected from the group consisting of:
(i) halo,
(ii) —C$_{1-6}$alkyl, which is unsubstituted or substituted with 1-5 halo, and
(iii) —OR$^a$,
(c) —OR$^a$,
(d) halo,
(e) —CO$_2$R$^a$,
(f) —C(=O)NR$^b$R$^c$,
(g) —S(O)$_v$R$^d$,
(h) —CN,
(i) —NR$^b$R$^c$,
(j) —N(Rb)C(=O)R$^a$,
(k) —N(Rb)SO$_2$R$^d$,
(l) —O—CO$_2$R$^a$,
(m) —O—(C=O)—NR$^b$R$^c$,
(n) —NR$^b$—(C=O)—NR$^b$R$^c$, and
(o) —C(=O)R$^a$;
J is selected from the group consisting of:
(1) =C(R$^{16a}$)—,
(2) —CR$^{17}$R$^{18}$—,
(3) —C(=O)—, and
(4) —N(R$^b$)—;
Y is selected from the group consisting of:
(1) =C(R$^{16b}$)—,
(2) —CR$^{17}$R$^{18}$—,
(3) —C(=O)—,
(4) =N—, and
(5) —N(R$^{16b}$)—;
R$^{17}$ and R$^{18}$ are each independently selected from the group consisting of:
(1) hydrogen,
(2) halo,
(3) —OR$^a$,
(4) —C$_{1-6}$alkyl, which is unsubstituted or substituted with 1-4 substituents each independently selected from the group consisting of:
(a) halo,
(b) —OR$^a$,
(c) —CN,
(d) phenyl or heterocycle, wherein said heterocycle is selected from piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from the group consisting of:
(i) —OR$^a$,
(ii) halo,
(iii) —CN,
(iv) —C$_{1-6}$alkyl which is unsubstituted or substituted with 1-6 halo,
(5) phenyl or heterocycle wherein heterocycle is selected from pyridyl, pyrimidinyl, thienyl, pyridazinyl, piperidinyl, azetidinyl, piperazinyl, pyrrolidinyl, morpholinyl, tetrahydrofuranyl, tetrahydropyranyl and pyrazinyl, which phenyl or heterocycle is unsubstituted or substituted with 1-5 substituents each independently selected from the group consisting of:
(a) halo,
(b) —CN,
(c) —OR$^a$,
(d) nitro,
(e) —C$_{1-6}$alkyl which is unsubstituted or substituted with 1-6 halo;
or R$^{17}$ and R$^{18}$ and the atom to which they are attached join to form a 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from the group consisting of:
(a) halo,
(b) —OR$^a$,
(c) —C$_{1-6}$alkyl, which is unsubstituted or substituted with 1-6 halo, and
(d) phenyl;
R$^{16a}$ and R$^{16b}$ are each independently selected from the group consisting of:
(1) hydrogen,
(2) —C$_{1-4}$alkyl, which is unsubstituted or substituted with 1-5 substituents each independently selected from the group consisting of:
(a) halo,
(b) —OR$^a$,
(c) —C$_{3-6}$cycloalkyl,
(d) phenyl or heterocycle, wherein said heterocycle is selected from: imidazolyl, oxazolyl, pyridyl, pyrimidinyl, pyrazinyl, pyridazinyl, piperidinyl, piperazinyl, pyrrolidinyl, thiazolyl, thienyl, triazolyl, isoxazolyl and morpholinyl, which phenyl or heterocycle is unsubstituted or substituted with 1-3 substituents each independently selected from the group consisting of:
(i) halo,
(ii) —OR$^a$,
(iii) —CN, and
(iv) C$_{1-6}$alkyl, which is unsubstituted or substituted with 1-6 halo,
(3) phenyl or heterocycle, wherein heterocycle is selected from: imidazolyl, oxazolyl, pyridyl, pyrimidinyl, pyrazinyl, pyridazinyl, tetrahydrofuryl, piperidinyl, piperazinyl, pyrrolidinyl, azetidinyl, thiazolyl, thienyl, triazolyl, isoxazolyl and morpholinyl, which phenyl or heterocycle is unsubstituted or substituted with 1-3 substituents each independently selected from the group consisting of:
(a) halo,
(b) —OR$^a$,
(c) —C$_{3-6}$cycloalkyl,
(d) —C$_{1-4}$alkyl which is unsubstituted or substituted with 1-6 halo, and
(e) phenyl, which is unsubstituted or substituted with 1-5 substituents each independently selected from the group consisting of:
(i) halo,
(ii) —C$_{1-6}$alkyl, which is unsubstituted or substituted with 1-6 halo, and
(iii) —OR$^a$,
(4) halo,
(5) —OR$^a$,
(6) —CN,
(7) —CO$_2$R$^a$,
(8) —NR$^b$R$^c$, and
(9) —C(=O)NR$^b$R$^c$;

or $R^{16a}$ and $R^{16b}$ and the atom(s) to which they are attached join to form a ring selected from cyclopentenyl, cyclohexenyl, phenyl, pyridyl, pyrimidinyl, pyrazinyl, pyridazinyl, furanyl, dihydrofuranyl, dihydropyranyl, thiazolyl, isothiazolyl, oxazolyl, isoxazolyl, imidazolyl, triazolyl, thienyl, dihydrothienyl and dihydrothiopyranyl, which ring is unsubstituted or substituted with 1-5 substituents each independently selected from the group consisting of:
- (a) —$C_{1-6}$alkyl, which is unsubstituted or substituted with 1-3 substituents each independently selected from the group consisting of:
  - (i) halo,
  - (ii) —$OR^a$,
  - (iii) —$C_{3-6}$cycloalkyl,
  - (iv) phenyl or heterocycle, wherein heterocycle is selected from pyridyl, pyrimidinyl, pyrazinyl, pyridazinyl, piperidinyl, piperazinyl, pyrrolidinyl, thienyl and morpholinyl, which phenyl or heterocycle is unsubstituted or substituted with 1-5 substituents each independently selected from the group consisting of:
    - (I) —$OR^a$,
    - (II) halo,
    - (III) —CN, and
    - (IV) —$C_{1-6}$alkyl which is unsubstituted or substituted with 1-6 halo,
  - (v) —$CO_2R^a$,
  - (vi) —$NR^bR^c$,
  - (vii) —$S(O)_vR^d$,
  - (viii) —$C(=O)NR^bR^c$,
  - (ix) —$N(Rb)CO_2R^a$, and
  - (x) —$N(Rb)SO_2R^d$,
- (b) phenyl or heterocycle, wherein said heterocycle is selected from pyridyl, pyrimidinyl, pyrazinyl, pyridazinyl, piperidinyl, azetidinyl, piperazinyl, pyrrolidinyl, thienyl and morpholinyl, which phenyl or heterocycle is unsubstituted or substituted with 1-5 substituents each independently selected from the group consisting of:
  - (i) halo,
  - (ii) —$OR^a$,
  - (iii) —CN, and
  - (iv) —$C_{1-6}$alkyl which is unsubstituted or substituted with 1-6 halo
- (c) halo,
- (d) —$S(O)_vR^d$,
- (e) —$OR^a$,
- (f) —CN,
- (g) —$C(=O)R^a$,
- (h) —$NR^bR^c$,
- (i) —$C(=O)NR^bR^c$,
- (j) —$CO_2R^a$,
- (k) —$(NR^b)CO_7R^a$,
- (l) —O—(C=O) —$NR^bR^c$,
- (m) —$(NR^b)$—(C=O) —$NR^bR^c$,
- (o) oxo, and
- (p) —$(NR^b)SO_2R^d$;

$R^a$ is selected from the group consisting of:
(1) hydrogen,
(2) $C_{1-6}$alkyl, which is unsubstituted or substituted with 1-7 substituents each independently selected from the group consisting of:
  - (a) halo,
  - (b) —O—$C_{1-6}$alkyl, which is unsubstituted or substituted with 1-6 halo,
  - (c) hydroxyl,
  - (d) —CN, and
  - (e) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
    - (i) halo,
    - (ii) —O—$C_{1-6}$alkyl, which is unsubstituted or substituted with 1-6 halo,
    - (iii) —CN,
    - (iv) nitro,
    - (v) hydroxyl, and
    - (vi) —$C_{1-6}$alkyl, which is unsubstituted or substituted with 1-6 halo,
(3) phenyl or heterocycle wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
  - (a) halo,
  - (b) —CN,
  - (c) —O—$C_{1-6}$alkyl, which is unsubstituted or substituted with 1-6 halo,
  - (d) nitro,
  - (e) hydroxyl, and
  - (f) —$C_{1-6}$alkyl, which is unsubstituted or substituted with 1-6 halo, and
(4) —$C_{3-6}$cycloalkyl, which is unsubstituted or substituted with 1-6 halo;

$R^b$ and $R^c$ are each independently selected from the group consisting of:
(1) hydrogen,
(2) $C_{1-6}$alkyl, which is unsubstituted or substituted with 1-7 substituents each independently selected from the group consisting of:
  - (a) halo,
  - (b) —$OR^a$,
  - (c) —CN,
  - (d) —$CO_2R^a$,
  - (e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
    - (i) halo,
    - (ii) —$OR^a$,
    - (iii) —$C_{1-6}$alkyl, which is unsubstituted or substituted with 1-6 halo, and
    - (iv) nitro,
(3) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:

(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo,
(e) —CN, and
(f) —CO$_2$R$^a$,
(4) —C$_{3-6}$cycloalkyl, which is unsubstituted or substituted with 1-6 halo;
or R$^b$ and R$^c$ and the nitrogen to which they are attached join to form a 4-, 5-, or 6-membered ring optionally containing an additional heteroatom selected from N, O, and S, wherein the sulfur is optionally oxidized to the sulfone or sulfoxide, which ring is unsubstituted or substituted with 1-4 substituents each independently selected from the group consisting of:
(a) halo,
(b) —OR$^a$, and
(c) —C$_{1-6}$alkyl, which is unsubstituted or substituted with 1-6 halo, and
(d) phenyl;
R$^d$ is selected from the group consisting of:
(1) C$_{1-6}$alkyl, which is unsubstituted or substituted with 1-4 substituents each independently selected from the group consisting of:
(a) halo,
(b) —OR$^a$,
(c) —CO$_2$R$^a$,
(d) —CN, and
(e) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(i)
(ii) —OR$^a$,
(iii) —C$_{1-6}$alkyl, which is unsubstituted or substituted with 1-6 halo, and
(iv) nitro,
(2) phenyl or heterocycle, wherein said heterocycle is selected from pyridyl, pyrimidinyl, thienyl, pyridazinyl, piperidinyl, azetidinyl, furanyl, piperazinyl, pyrrolidinyl, morpholinyl, tetrahydrofuranyl, tetrahydropyranyl and pyrazinyl, which phenyl or heterocycle is unsubstituted or substituted with 1-3 substituents each independently selected from the group consisting of:
(a) halo,
(b) —OR$^a$,
(c) —C$_{1-6}$alkyl, which is unsubstituted or substituted with 1-6 halo,
(d) —C$_{3-6}$cycloalkyl, which is unsubstituted or substituted with 1-6 halo
(e) —CN, and
(f) —CO$_2$R$^a$, and
(3) —C$_{3-6}$cycloalkyl, which is unsubstituted or substituted with 1-6 halo;
R$^e$ and R$^f$ are each independently selected from the group consisting of:
(1) hydrogen,
(2) —C$_{1-4}$alkyl, which is unsubstituted or substituted with 1-6 halo,
(3) —OR$^a$,
(4) —CN,
(5) halo,
(6) phenyl, and
(7) benzyl;
or where R$^e$ and R$^f$ and the carbon atom or atoms to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from the group consisting of:
(a) halo,
(b) —OR$^a$,
(c) —C$_{1-6}$alkyl, which is unsubstituted or substituted with 1-6 halo, and
(d) phenyl;
R$^g$ and R$^h$ are each independently selected from the group consisting of:
(1) —C$_{1-4}$alkyl, which is unsubstituted or substituted with 1-6 halo,
(2) —OR$^a$,
(3) —C$_{3-6}$cycloalkyl, which is unsubstituted or substituted with 1-6 halo,
(4) phenyl, and
(5) benzyl;
or where R$^g$ and R$^h$ and the silicon atom to which they are attached join to form a 3-, 4-, 5-, or 6-membered ring optionally containing a heteroatom selected from N, O, and S, wherein the sulfur is optionally oxidized to the sulfone or sulfoxide, which ring is unsubstituted or substituted with 1-4 substituents each independently selected from the group consisting of:
(a) halo,
(b) —OR$^a$,
(c) —C$_{1-4}$alkyl, which is unsubstituted or substituted with 1-3 halo, and
(d) phenyl;
R$^i$ and R$^j$ are each independently selected from the group consisting of:
(1) hydrogen,
(2) —C$_{1-4}$alkyl, which is unsubstituted or substituted with 1-6 halo,
(3) halo,
(4) phenyl, and
(5) benzyl;
v is 0, 1, or 2;
or a pharmaceutically acceptable salts thereof and individual enantiomers and diastereomers thereof.

2. The compound of claim 1 having the formula Ih:

Ih or a pharmaceutically acceptable salts thereof and individual enantiomers and diastereomers thereof.

3. The compound of claim 1, wherein $R^6$ and $R^7$ and the carbon atom or atoms to which they are attached join to form a ring selected from cyclopropyl, cyclobutyl, cyclopentyl, cyclohexyl, cycloheptyl, cyclooctyl, cyclopentenyl, cyclohexenyl, cycloheptenyl, dioxolanyl, dioxanyl, tetrahydrofuranyl, tetrahydropyranyl, pyrrolidinyl, and piperidinyl, which ring is unsubstituted or substituted with 5 substituents each independently selected from the group consisting of:

(1) —$C_{1-6}$alkyl, which is unsubstituted or substituted with 1-3 substituents where the substitutents are each independently selected from: halo, —$OR^a$, and phenyl, (2) —$C_{3-6}$cycloalkyl, wherein the $C_{3-6}$cycloalkyl group is optionally fused to the ring, and which $C_{3-6}$cycloalkyl group is unsubstituted or substituted with 1-3 substituents each independently selected from: halo, —$OR^a$, and phenyl, (3) phenyl or heterocycle, wherein heterocycle is selected from: pyridyl, pyrimidinyl, pyrazinyl, pyridazinyl, piperidinyl, piperazinyl, pyrrolidinyl, thienyl, morpholinyl, thiazolyl and oxazolyl, wherein the phenyl or heterocycle is optionally fused to the ring, and which phenyl or heterocycle is unsubstituted or substituted with 1-3 substituents each independently selected from: halo, —$OR^a$, and —$C_{1-4}$alkyl, which is unsubstituted or substituted with 1-5 fluoro, (4) halo, (5) oxo, (6) —$CO_2R^a$, and (7) —$C(=O)R^a$ or a pharmaceutically acceptable salt thereof and individual enantiomers and diastereomers thereof.

4. A compound selected from the following group:

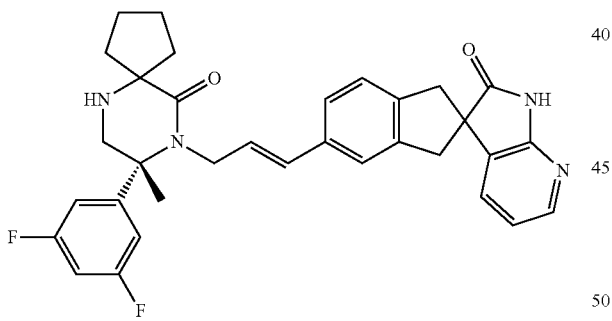

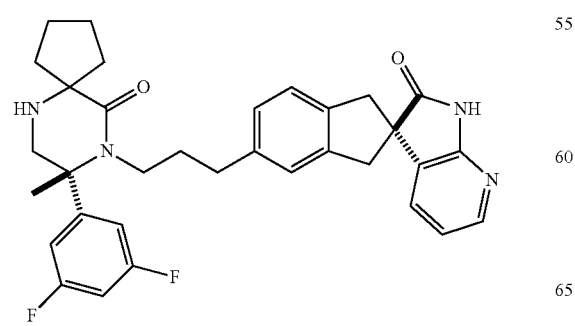

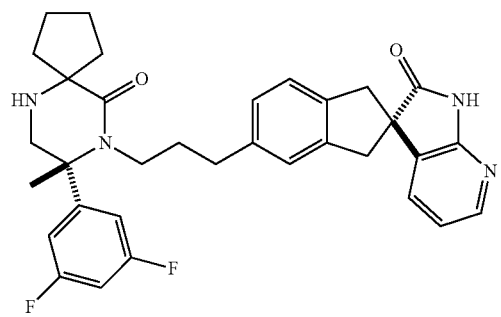

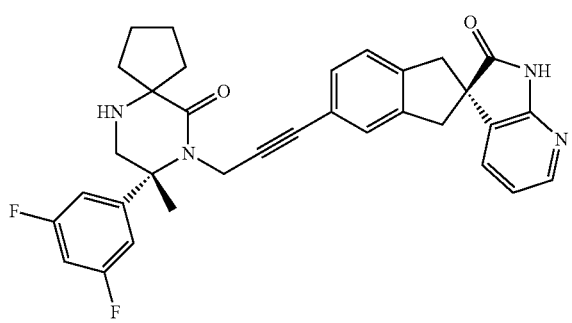

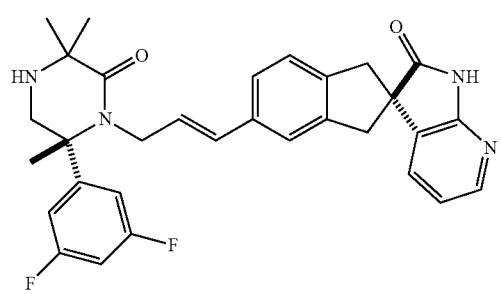

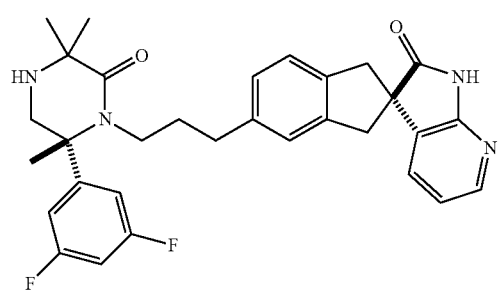

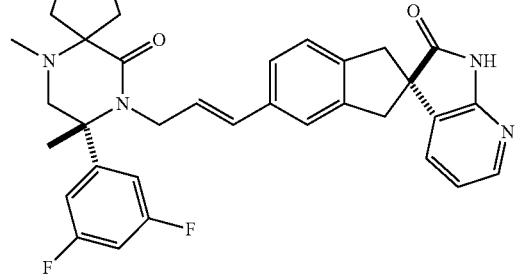

127
-continued
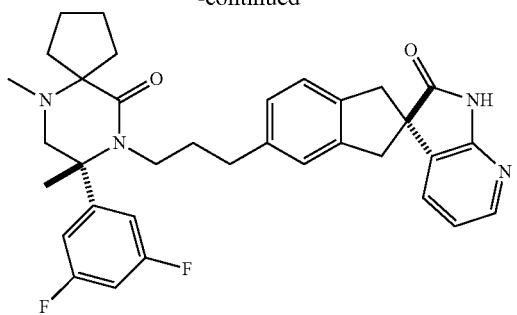
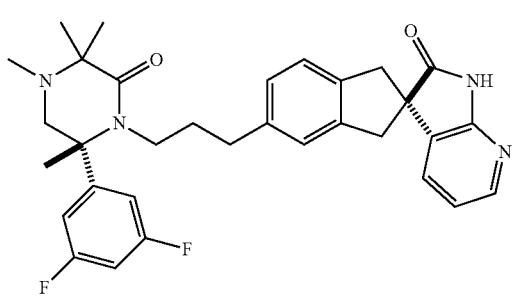
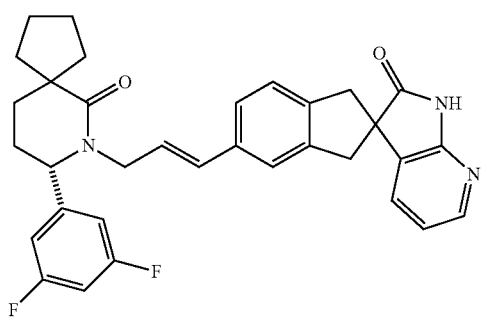
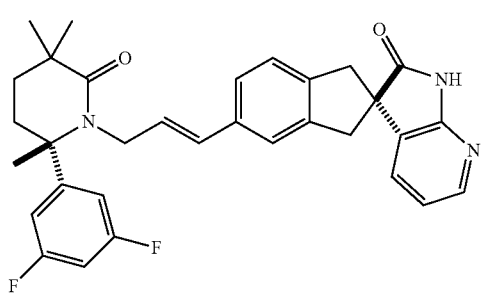
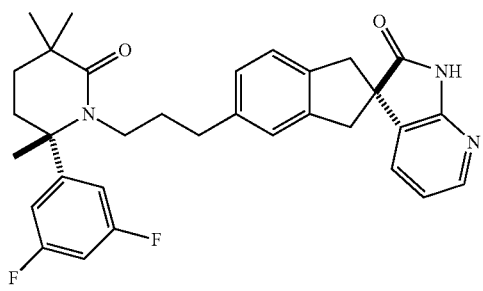
128
-continued
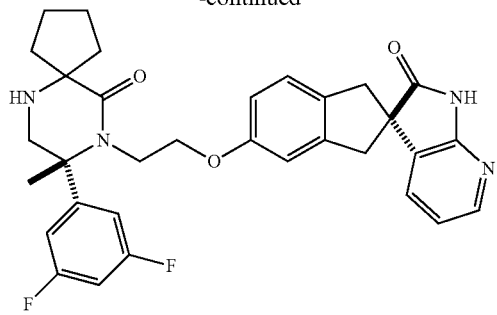
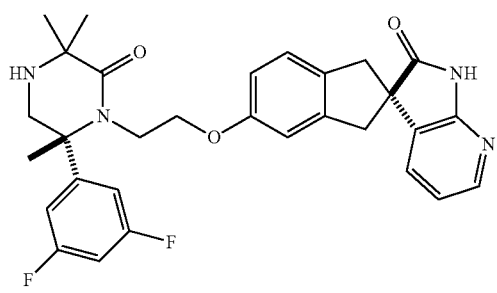
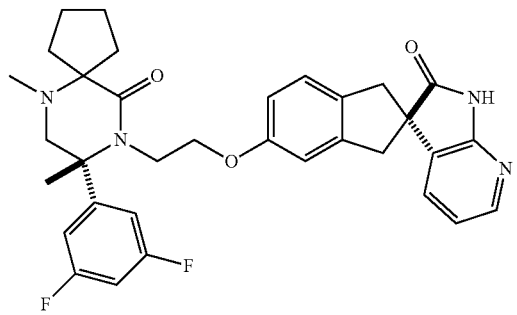
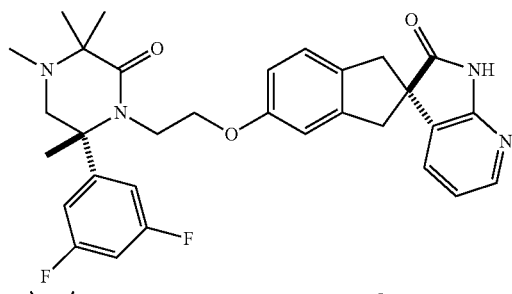
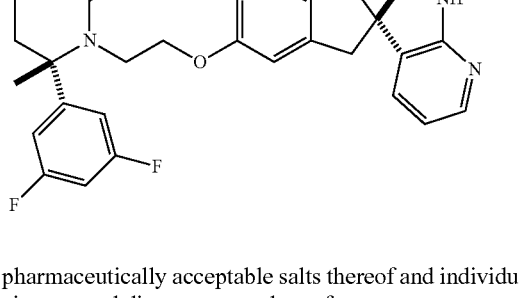
or a pharmaceutically acceptable salts thereof and individual enantiomers and diastereomers thereof.

5. The compound of claim 1 having the Formula Ii:

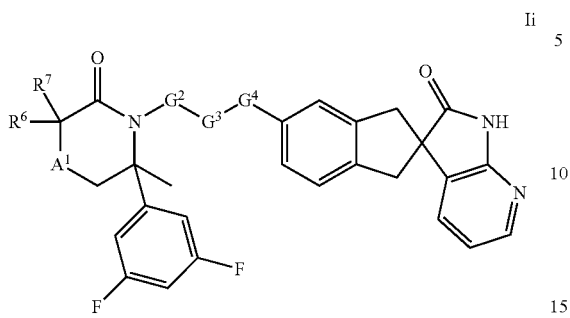

Ii wherein:
$R^6$ and $R^7$ are each methyl or $R^6$ and $R^7$ are joined together with the atom to which they are attached to form a cyclopentyl ring;
$A^1$ is:
(1) —$CH_2$—
(2) —$N(R^8)$—, wherein $R^8$ is selected from H and $C_{1-6}$alkyl; and
-$G^2$-$G^3$-$G^4$- is selected from the group consisting of:
—$CH_2$—$CH_2$—$CH_2$—,
—$CH_2$—CH=CH—,
—$CH_2$—C≡C-and
—$CH_2$—$CH_2$—O—;
or a pharmaceutically acceptable salts thereof and individual enantiomers and diastereomers thereof.

6. A pharmaceutical composition which comprises an inert carrier and the compound of claim 1 or a pharmaceutically acceptable salt thereof and individual enantiomers and diastereomers thereof.

7. The compound of claim 1, wherein $G^1$ is a bond or a pharmaceutically acceptable salt thereof and individual enantiomers and diastereomers thereof.

8. The compound of claim 1, wherein $G^2$ is a bond or a pharmaceutically acceptable salt thereof and individual enantiomers and diastereomers thereof.

9. The compound of claim 1, wherein -$G^2$-$G^3$-$G^4$- is selected from the group consisting of:
—$CH_2$—$CH_2$—$CH_2$—,
—$CH_2$—CH=CH—,
—$CH_2$—C≡C—,
—$CH_2$—$CH_2$—S—,
—$CH_2$—$CH_2$—S(=O)—,
—$CH_2$—$CH_2$—(C=O)—,
—$CH_2$—(C=O)—O—, and
—$CH_2$—$CH_2$—O— or
a pharmaceutically acceptable salt thereof and individual enantiomers and diastereomers thereof.

10. The compound of claim 1, wherein $R^{5a}$, $R^{5b}$ and $R^{5c}$ are independently selected from hydrogen, —CN and halo or a pharmaceutically acceptable salt thereof and individual enantiomers and diastereomers thereof.

11. The compound of claim 1 having the Formula Ij:

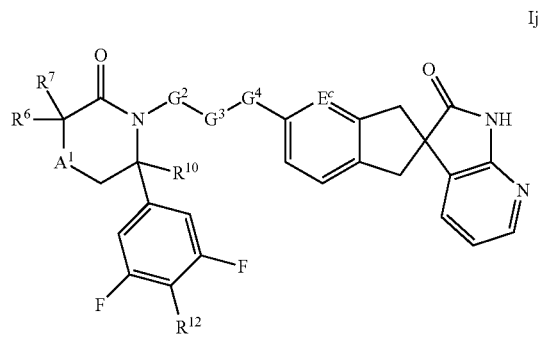

Ij wherein
$R^6$ and $R^7$ are each $C_{1-4}$alkyl, which may be unsubstituted or substituted with 1-3 fluoro, or $R^6$ and $R^7$ are joined together with the atom to which they are attached to form a ring selected from: cyclopentyl, cyclohexyl, cycloheptyl, and tetrahydropyranyl;
$R^{10}$ is selected from the group consisting of:
(1) hydrogen, and
(2) methyl;
$R^{12}$ is optionally not present or is halo;
$A^1$ is:
(1) —$CH_2$—, and
(2) —$N(R^8)$—, wherein $R^8$ is selected from H and $C_{1-6}$alkyl, which is unsubstituted or substituted with 1-3 fluoro;
$E^c$ is —CH= or —N=; and
-$G^2$-$G^3$-$G^4$- is selected from the group consisting of:
—$CH_2$—$CH_2$—$CH_2$—,
—$CH_2$—CH=CH—,
—$CH_2$—C≡C—,
—$CH_2$—$CH_2$—S—,
—$CH_2$—$CH_2$—S(=O)—,
—$CH_2$—$CH_2$—(C=O)—,
—$CH_2$—(C=O)—O—, and
—$CH_2$—$CH_2$—O—;
or a pharmaceutically acceptable salts thereof and individual enantiomers and diastereomers thereof.

12. A compound selected from the following group:

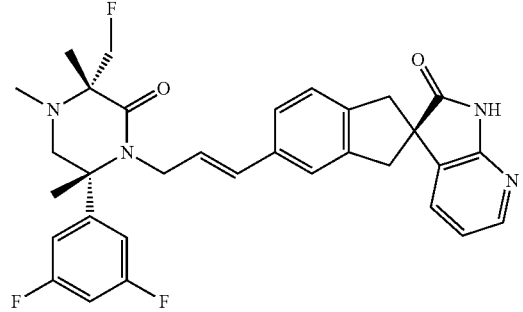

131
-continued
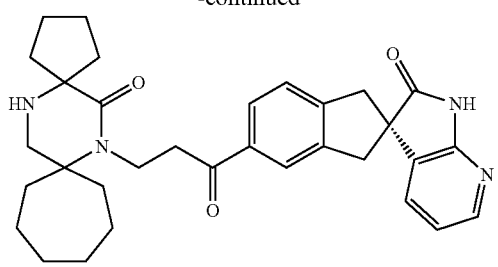
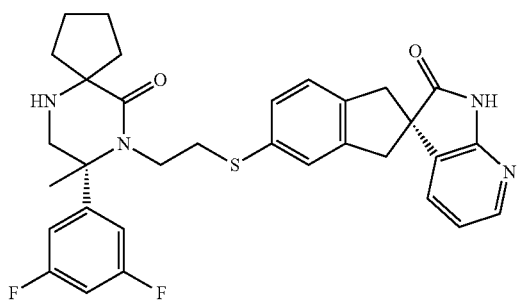
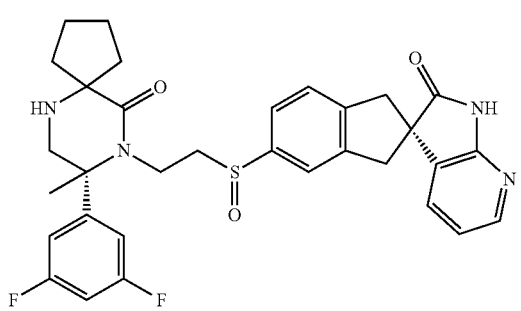
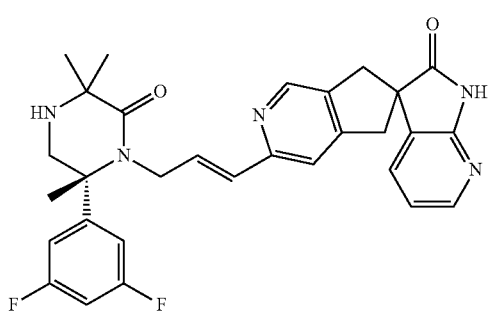
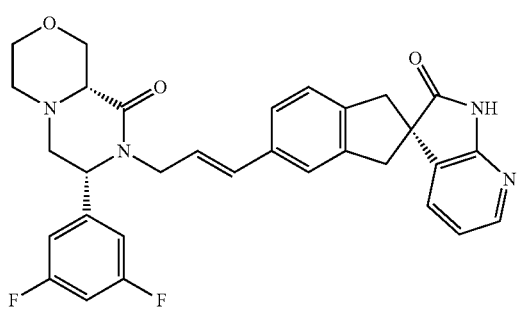
132
-continued
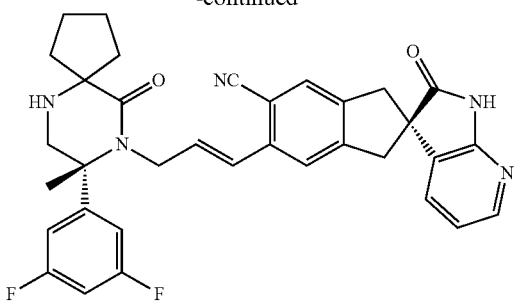
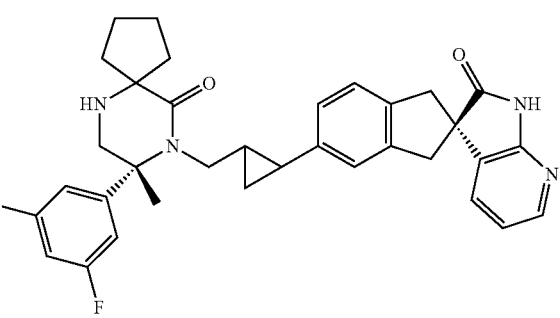
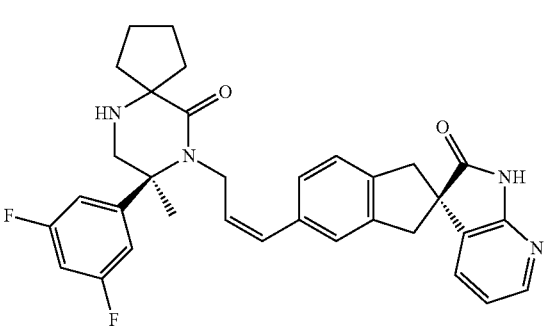
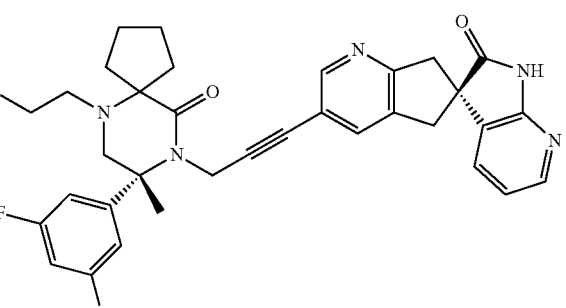
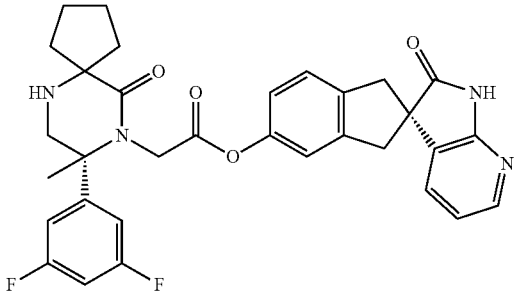

133
-continued
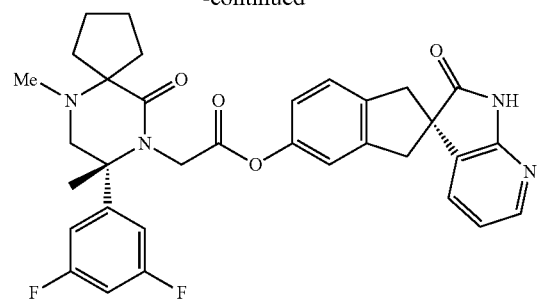
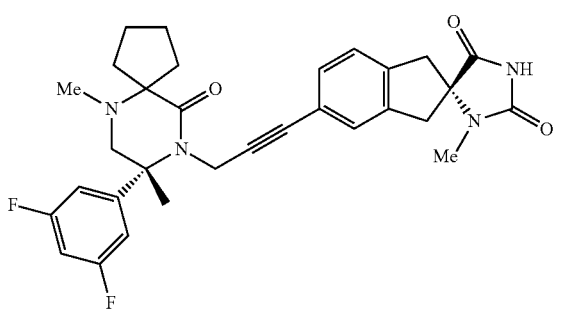
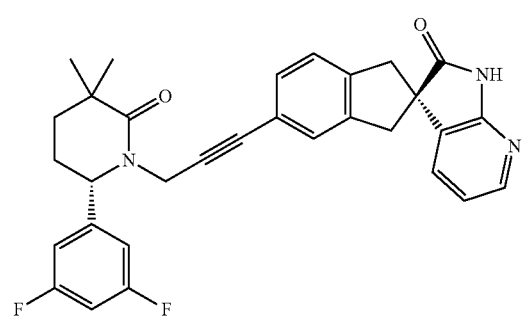
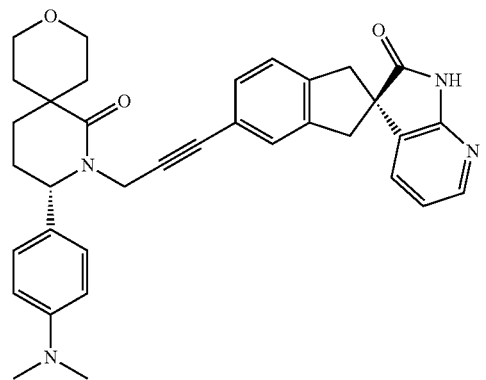
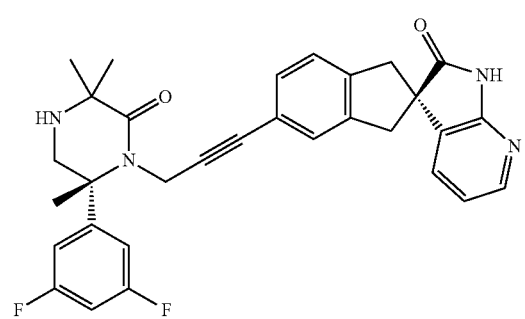
134
-continued
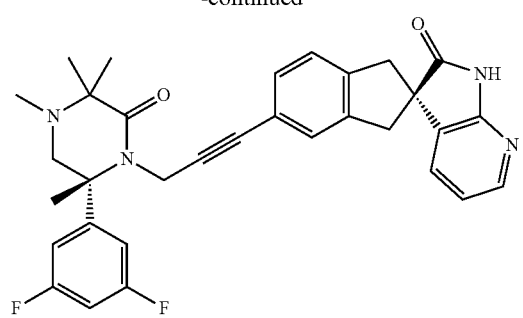
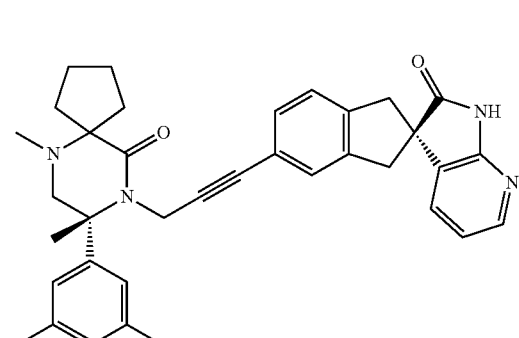
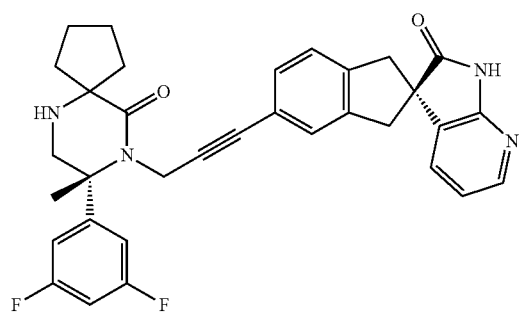
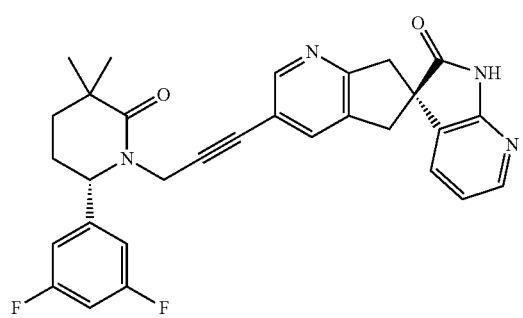
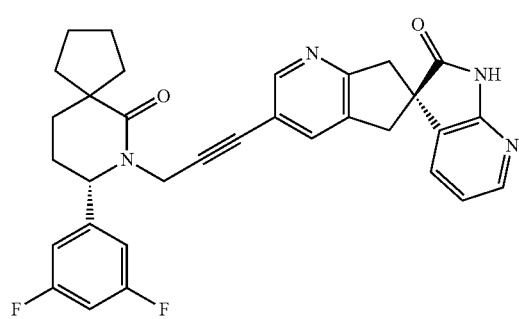

135
-continued
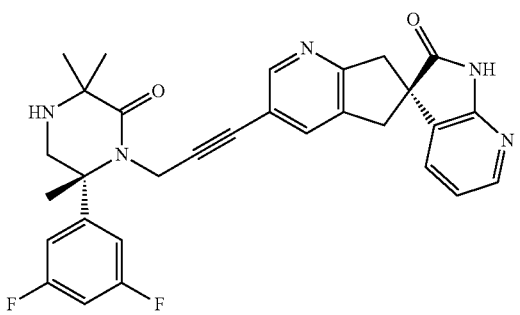
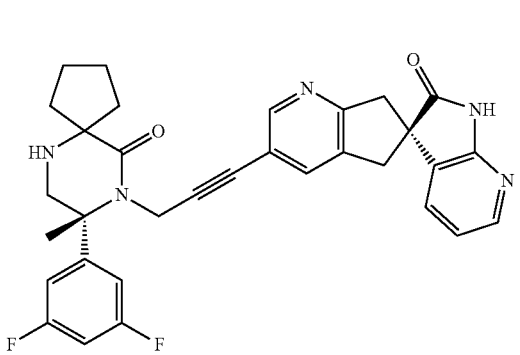
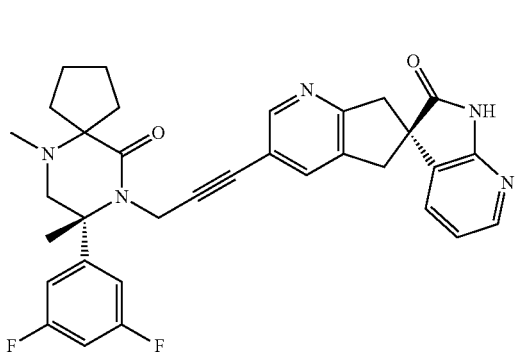
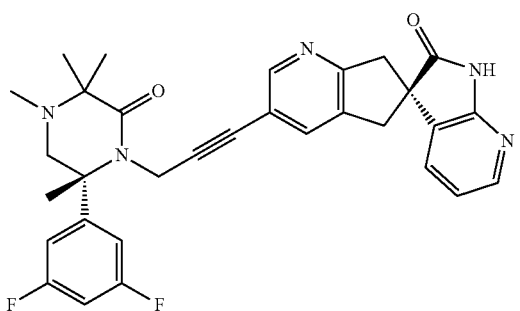
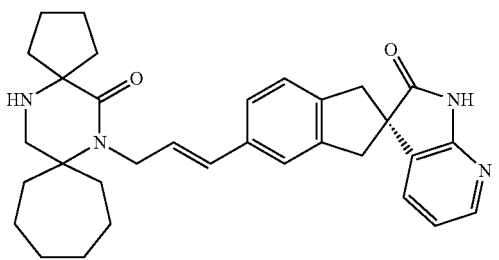
136
-continued
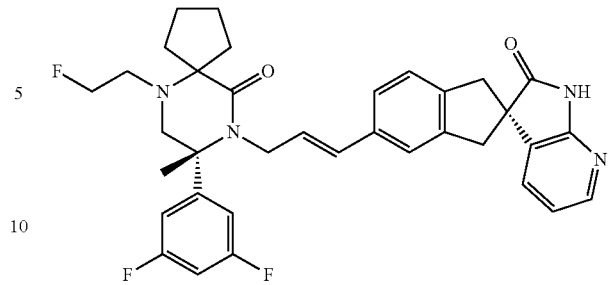
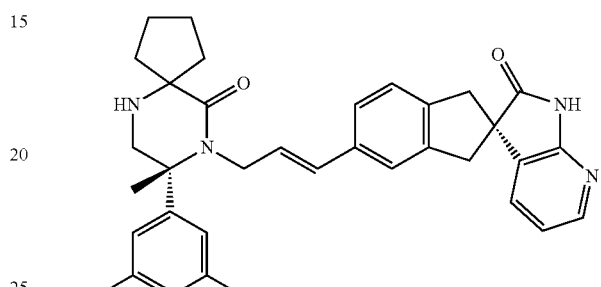
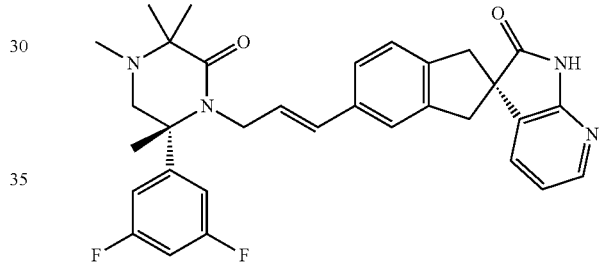
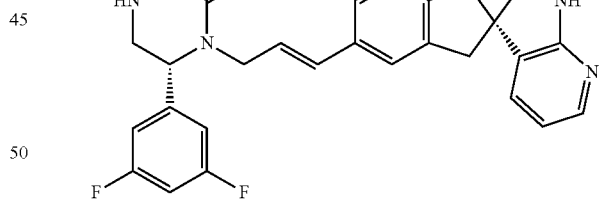
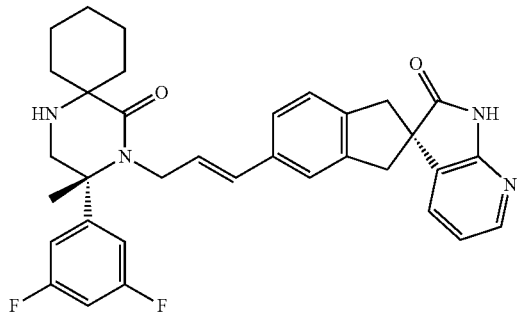

137
-continued
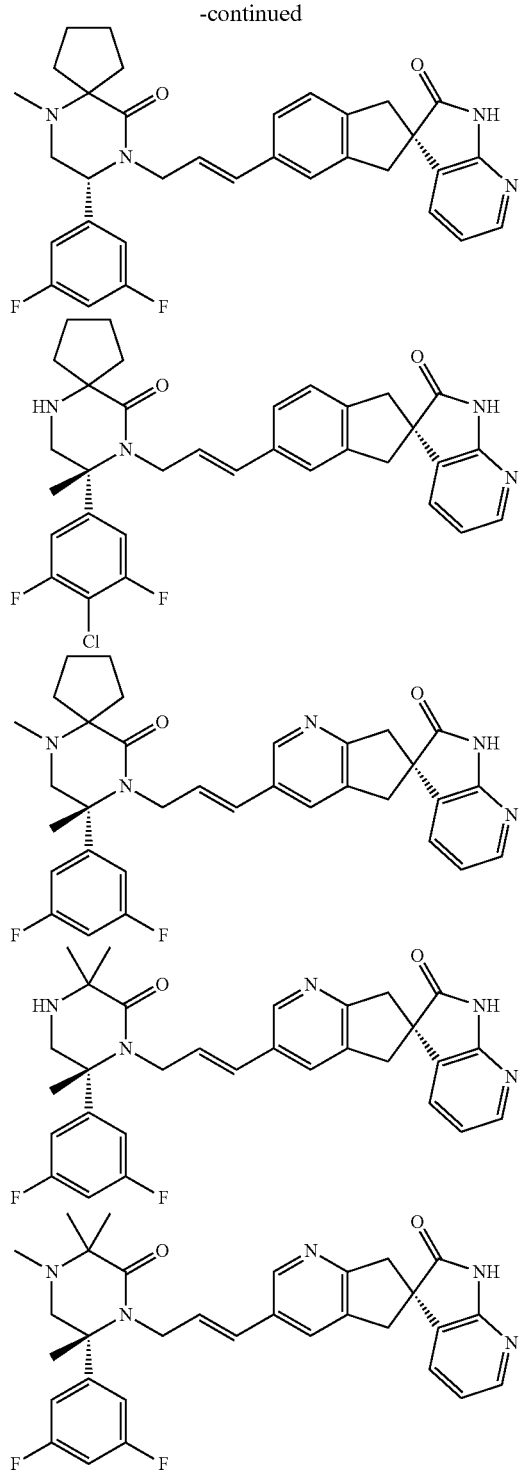
138
-continued
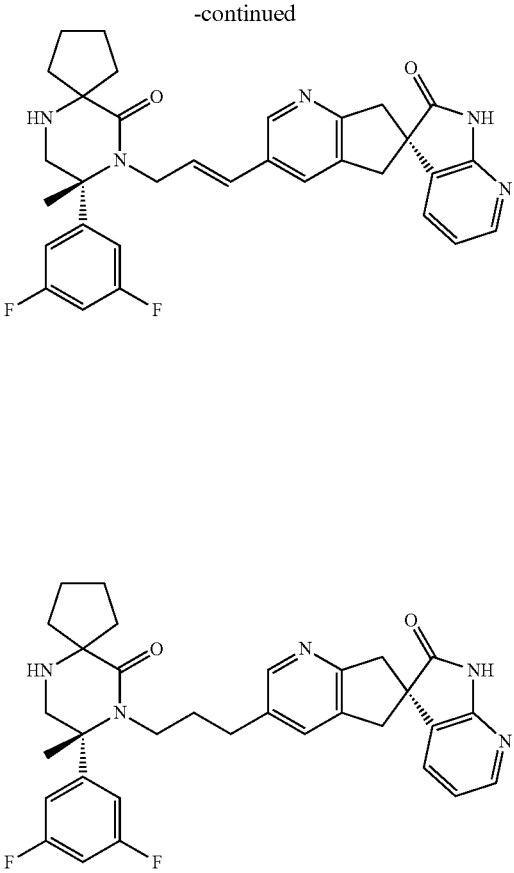
or a pharmaceutically acceptable salts thereof and individual enantiomers and diastereomers thereof.
* * * * *